United States Patent [19]

Flynn et al.

[11] Patent Number: 5,527,795
[45] Date of Patent: Jun. 18, 1996

US005527795A

[54] MERCAPTOACETYLAMIDE DERIVATIVES USEFUL AS INHIBITORS OF ENKEPHALINASE AND ACE

[75] Inventors: Gary A. Flynn; Philippe Bey; Alan M. Warshawsky; Douglas W. Beight; Shujaath Mehdi; Eugene L. Giroux, all of Cincinnati; Timothy P. Burkholder, Fairfield, all of Ohio; Edward D. Daugs, Midland, Mich.; John F. French, Cincinnati, Ohio

[73] Assignee: Merrell Pharmaceuticals Inc., Cincinnati, Ohio

[21] Appl. No.: 417,179

[22] Filed: Apr. 5, 1995

Related U.S. Application Data

[60] Division of Ser. No. 149,572, Nov. 9, 1993, Pat. No. 5,430,145, which is a continuation-in-part of Ser. No. 75,981, Jun. 11, 1993, abandoned, which is a continuation-in-part of Ser. No. 863,600, Apr. 3, 1992, abandoned, which is a continuation-in-part of Ser. No. 735,496, Jul. 25, 1991, abandoned, which is a continuation-in-part of Ser. No. 600,052, Oct. 18, 1990, abandoned.

[51] Int. Cl.$^6$ .......................... A61K 31/55; C07D 457/04
[52] U.S. Cl. ........................... 514/214; 540/521; 540/522
[58] Field of Search ................................. 514/214

[56] References Cited

U.S. PATENT DOCUMENTS 5,430,145   7/1995   Flynn et al. ............................ 514/521

Primary Examiner—Robert T. Bond
Attorney, Agent, or Firm—Charlotte L. Barney

[57] ABSTRACT

The present invention relates to certain novel mercaptoacetylamide derivatives useful as inhibitors of enkephalinase and of ACE.

13 Claims, No Drawings

MERCAPTOACETYLAMIDE DERIVATIVES USEFUL AS INHIBITORS OF ENKEPHALINASE AND ACE

This is a division of application Ser. No. 08/149,572, filed Nov. 9, 1993 U.S. Pat. No. 5,430,145, which is a CIP of 08/075,981, filed Jun. 11, 1993, now abandoned; which is a CIP of 07/863,600, filed Apr. 3, 1992, now abandoned; which is a CIP of 07/735,496, filed Jul. 25, 1991 now abandoned; which is a CIP of 07/600,052, filed Oct. 18, 1990 now abandoned.

Enkephalinase or, more specifically, endopeptidase-24.11, is a mammalian ectoenzyme which is involved in the metabolic degradation of certain circulating regulatory peptides. This enzyme, which is a $Zn^{+2}$-metallopeptidase, exerts its effect by cleaving the extracellular peptides at the amino group of hydrophobic residues and thus inactivates the peptides as regulatory messengers.

Enkephalinase is involved in the metabolic degradation of a variety of circulating regulatory peptides including endorphins, such as β-endorphin and the enkephalins, atrial natriuretic peptide (ANP), and other circulating regulatory peptides.

Endorphins are naturally-occurring polypeptides which bind to opiate receptors in various areas of the brain and thereby provide an analgesic effect by raising the pain threshold. Endorphins occur in various forms including α-endorphin, β-endorphin, γ-endorphin as well as the enkephalins. The enkephalins, i.e., Met-enkephalin and Leu-enkephalin, are pentapeptides which occur in nerve endings of brain tissue, spinal cord and the gastrointestinal tract. Like the other endorphins, the enkephalins provide an analgesic effect by binding to the opiate receptors in the brain. By inhibiting enkephalinase, the metabolic degradation of the naturally-occurring endorphins and enkephalins are inhibited, thereby providing a potent endorphin- or enkephalin-mediated analgesic effect. Inhibition of enkephalinase would therefore be useful in a patient suffering from acute or chronic pain. Inhibition of enkephalinase would also be useful in providing an antidepressant effect and in providing a reduction in severity of withdrawal symptoms associated with termination of opiate or morphine administration. In addition, inhibition of enkephalinase would also be useful in the treatment of irritable bowel syndrome.

ANP refers to a family of naturally-occurring peptides which are involved in the homeostatic regulation of blood pressure, as well as sodium and water levels. ANP have been found to vary in length from about 21 to about 126 amino acids with a common structural feature being one or more disulfide-looped sequences of 17 amino acids with various amino- and carboxy-terminal sequences attached to the cystine moiety. ANP have been found to bind to specific binding sites in various tissues including kidney, adrenal, aorta, and vascular smooth muscle with affinities ranging from about 50 pico-molar (pM) to about 500 nano-molar (nM) [Needleman, *Hypertension* 7, 469 (1985)]. In addition, it is believed that ANP binds to specific receptors in the brain and possibly serves as a neuromodulator as well as a conventional peripheral hormone.

The biological properties of ANP involve potent diuretic/ natriuretic and vasodilatory/hypotensive effects as well as an inhibitory effect on renin and aldosterone secretion [deBold, *Science* 230, 767 (1985)]. By inhibiting enkephalinase, the metabolic degradation of the naturally-occurring ANP are inhibited, thereby providing a potent ANP-mediated diuretic, natriuretic, hypotensive, hypoaldosteronemic effects. Inhibition of enkephalinase would therefore be useful in a patient suffering from disease states characterized by abnormalities in fluid, electrolyte, blood pressure, intraocular pressure, renin, or aldosterone homeostasis, such as, but not limited to, hypertension, renal diseases, hyperaldosteronemia, cardiac hypertrophy, glaucoma and congestive heart failure.

In addition, the compounds of the present invention are inhibitors of Angiotensin-Converting Enzyme (ACE). ACE is a peptidyl dipeptidase which catalyzes the conversion of angiotensin I to angiotensin II. Angiotensin II is a vasoconstrictor which also stimulates aldosterone secretion by the adrenal cortex. Inhibition of ACE would therefore be useful in a patient suffering from disease states such as hypertension and congestive heart failure [See William W. Douglas, "Polypeptides—Angiotensin, Plasma Kinins, and Others", Chapter 27, in GOODMAN AND GILLMAN'S THE PHARMACOLOGICAL BASIS OF THERAPEUTICS, 7th edition, 1985, pp. 652–3, MacMillan Publishing Co., New York, N.Y.]. In addition, it has been discovered that ACE inhibitors are useful in treating cognitive disorders [German Application No. 3901-291-A, published Aug. 3, 1989].

Bradykinin refers to a naturally-occurring peptide which is a very powerful vasodilator and causes increased capillary permeability. By inhibiting enkephalinase and ACE, the metabolic degradation of bradykinin is inhibited, thereby providing increased levels of bradykinin in the circulation.

In addition, the compounds of the present invention are useful as inhibitors of smooth cell proliferation. Smooth muscle cell proliferation in the intima of muscular arteries is a primary cause of vascular stenosis in arteriosclerosis, after vascular surgery, and after coronary angioplasty. Several animal studies have indicated the renin-angiotensin system plays an important role in this vascular response to injury. Chronic treatment with angiotensin converting enzyme (ACE) inhibitors reduced myointimal thickening following balloon injury in rat carotid artery or aorta. Powell, J. S., Muller, R. K. M. and Baumgartner, H. R.; Suppression of the vascular response to injury: The role of angiotensin-converting enzyme inhibitors. J. Am. Coll. Cardiol. 17:137B–42B, 1991. More recently, atrial natruiuretic peptide (ANP) has been found to decrease myointimal proliferation. ANP is rapidly metabolized by receptor mediated clearance and by neutral endopeptidase (NEP). Inhibition of NEP significantly reduces proliferation in the balloon-injured rabbit vasculature. Davis, H. R., McGregor, D. C., Hoos, L., Mullins, D. E. and Sybertz, E. J.: Atrial naturiuretic factor and the neutral endopeptidase inhibitor SCH42495 prevent myointimal proliferation after vascular injury. Circ. 86:I-220, 1992. These studies imply that a dual inhibitor of ACE and NEP should be therapeutically useful in the treatment of conditions which require inhibition of smooth cell proliferation. Davis and Sybertz, European Patent Application 533084-Al, Mar. 24, 1993.

SUMMARY OF THE INVENTION

The present invention provides novel compounds of the Formula (I)

(I)

wherein

- $A_1$ and $A_2$ are each independently hydrogen or —$COOR_4$ wherein $R_4$ is hydrogen; —$CH_2O$—$C(O)C(CH_3)_3$; a $C_1$–$C_4$ alkyl; an Ar—Y— group wherein Ar is aryl and Y is a $C_0$–$C_4$ alkyl; or diphenylmethyl; with the proviso that where $A_1$ is hydrogen, $A_2$ is —$COOR_4$, and where $A_1$ is —$COOR_4$, $A_2$ is hydrogen;
- $B_1$ and $B_2$ are each independently hydrogen; hydroxy; —$OR_5$ wherein $R_5$ is a $C_1$–$C_4$ alkyl or an Ar—Y— group; or, where $B_1$ and $B_2$ are attached to adjacent carbon atoms, $B_1$ and $B_2$ can be taken together with said adjacent carbons to form a benzene ring or methylenedioxy;
- $R_2$ is hydrogen, $C_1$–$C_8$ alkyl; —$CH_2OCH_2CH_2OCH_3$ or an Ar—Y— group;
- $R_3$ is hydrogen, acetyl, —$CH_2O$—$C(O)C(CH_3)_3$ or benzoyl; and
- n is an integer 0 or 1.

The present invention further provides novel compounds of the Formula (II)
wherein

- $B_1$ and $B_2$ are each independently hydrogen; hydroxy; —$OR_5$ wherein $R_5$ is a $C_1$–$C_4$ alkyl or an Ar—Y— group wherein Ar is aryl and Y is a $C_0$–$C_4$ alkyl; or, where $B_1$ and $B_2$ are attached to adjacent carbon atoms, $B_1$ (II)

and $B_2$ can be taken together with said adjacent carbons to form a benzene ring or methylenedioxy;
- $R_2$ is hydrogen, $C_1$–$C_8$ alkyl, —$CH_2OCH_2CH_2OCH_3$ or an Ar—Y— group;
- $R_3$ is hydrogen, acetyl, —$CH_2O$—$C(O)C(CH_3)_3$ or benzoyl;
- $R_4$ is hydrogen, a $C_1$–$C_4$ alkyl or an Ar—Y— group, —$CH_2O$—$C(O)C(CH_3)_3$ or diphenylmethyl; and X is —O—, —S—, $$\underset{-N-}{R_6} \quad \text{or} \quad \underset{-N-}{\overset{\displaystyle C{\overset{O}{\nearrow}}\diagdown R_7}{|}},$$

wherein $R_6$ is hydrogen, a $C_1$–$C_4$ alkyl or an Ar—Y— group and $R_7$ is —$CF_3$, $C_1$–$C_{10}$ alkyl or an Ar—Y— group.

The present invention further provides a method of inhibiting enkephalinase in a patient in need thereof comprising administering to said patient an effective enkephalinase inhibitory amount of a compound of Formula (I) or (II). The present invention also provides a method of inhibiting ACE in a patient in need thereof comprising administering to said patient an effective ACE inhibitory amount of a compound of Formula (I) or (II).

In addition, the present invention provides a composition comprising an assayable amount of a compound of Formula (I) or (II) in admixture or otherwise in association with an inert carrier. The present invention also provides a pharmaceutical composition comprising an effective inhibitory amount of a compound of Formula (I) or (II) in admixture or otherwise in association with one or more pharmaceutically acceptable carriers or excipients.

DETAILED DESCRIPTION OF THE INVENTION

As used herein, the term "$C_1$–$C_4$ alkyl" refers to a saturated straight or branched chain hydrocarbyl radical of one to four carbon atoms and includes methyl, ethyl, propyl, isopropyl, n-butyl, isobutyl, tertiary butyl and the like. The terms "$C_1$–$C_8$ alkyl" and "$C_1$–$C_{10}$ alkyl" refer to saturated straight or branched chain hydrocarbyl radicals of one to eight and one to ten carbon atoms, respectively, including methyl, ethyl, propyl, isopropyl, n-butyl, isobutyl, tertiary butyl, pentyl, isopentyl, hexyl, 2,3-dimethyl-2-butyl, heptyl, 2,2-dimethyl-3-pentyl, 2-methyl-2-hexyl, octyl, 4-methyl-3-heptyl and the like. The term "halogen", "halo", "halide" or "Hal" refers to a chlorine, bromine, or iodine atom.

As used herein, the term "Ar—Y—" refers to a radical wherein Ar is an aryl group and Y is a $C_0$–$C_4$ alkyl. The term "Ar" refers to a phenyl or naphthyl group unsubstituted or substituted with from one to three substituents selected from the group consisting of methylenedioxy, hydroxy, $C_1$–$C_4$ alkoxy, fluoro and chloro. The term "$C_0$–$C_4$ alkyl" refers to a saturated straight or branched chain hydrocarbyl radical of zero to four carbon atoms and includes a bond, methyl, ethyl, propyl, isopropyl, n-butyl, isobutyl, tertiary butyl and the like. Specifically includes within the scope of the term "Ar—Y—" are phenyl, naphthyl, phenylmethyl or benzyl, phenylethyl, p-methoxybenzyl, 3,4-methylenedioxy, p-fluorobenzyl and p-chlorobenzyl.

As used herein, the designation "⌇" refers to a bond to a chiral atom for which the stereochemistry is not designated.

The compounds of Formula (I) wherein $A_1$ is —$COOR_4$ and $A_2$ is hydrogen can be prepared by utilizing procedures and techniques well known and appreciated by one of ordinary skill in the art. A general synthetic scheme for preparing these compounds is set forth in Scheme A wherein all substituents, unless otherwise indicated, are previously defined.

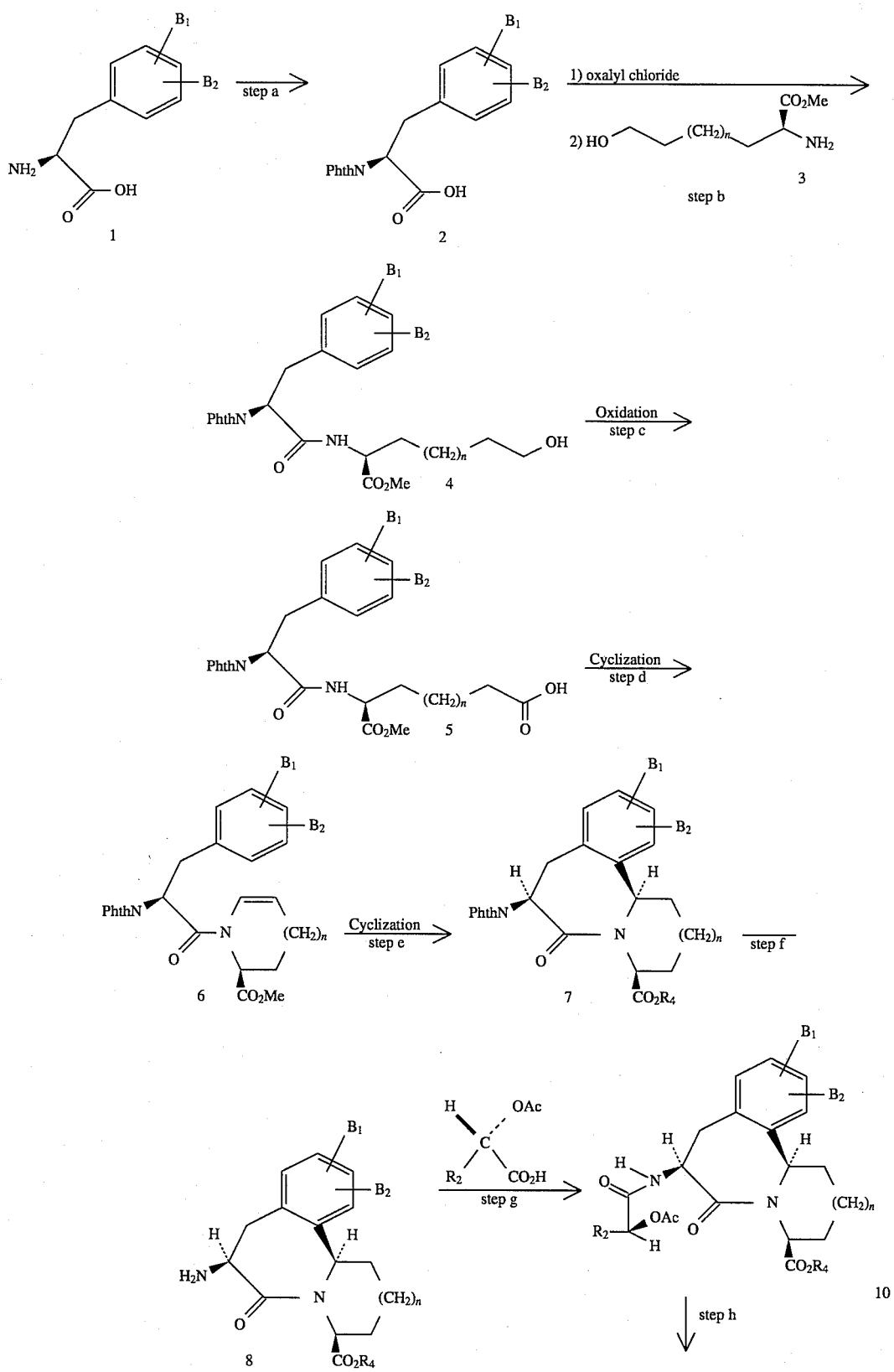

-continued
Scheme A

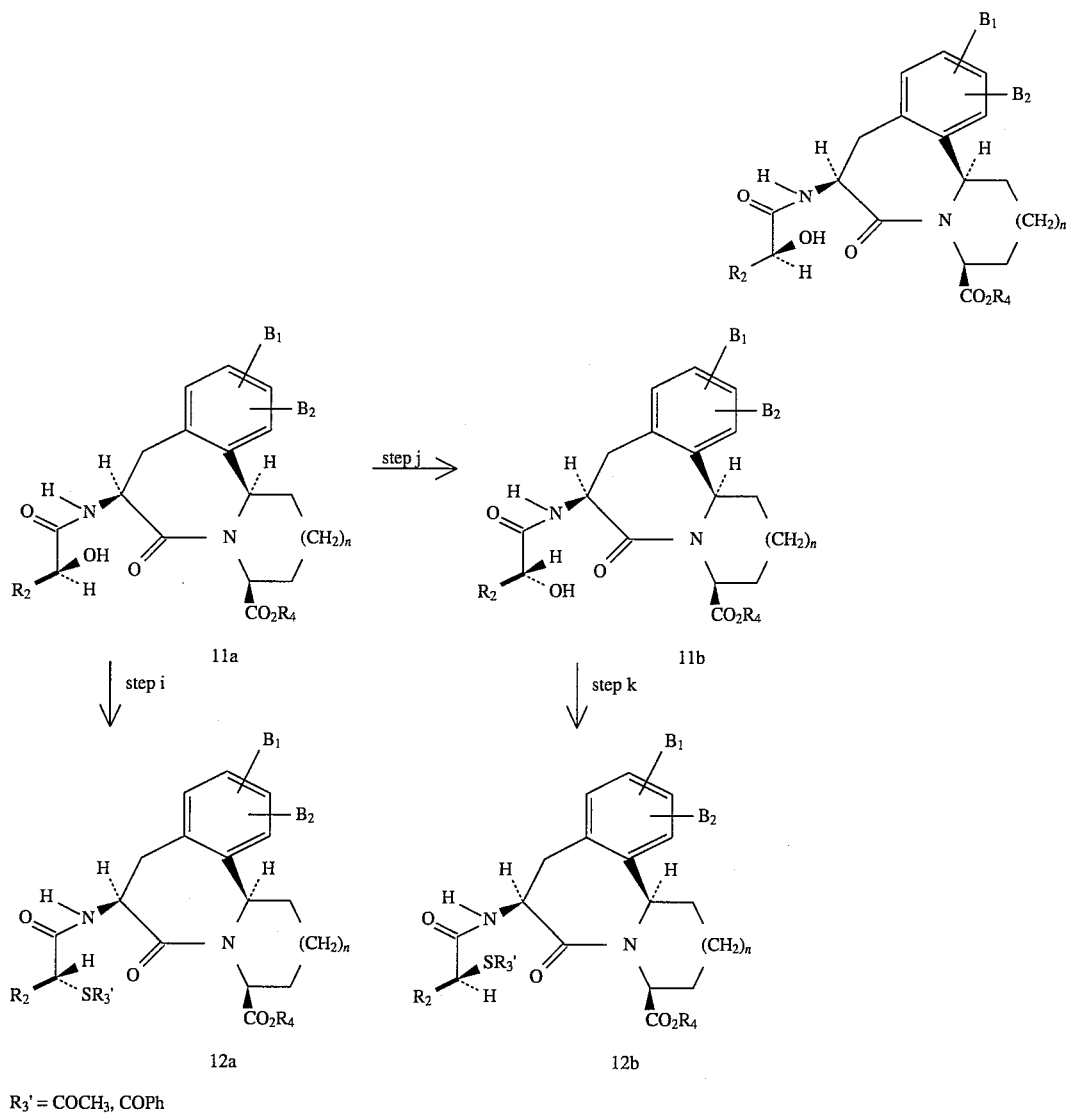

$R_3' = COCH_3, COPh$

In step a, the appropriate phthalimide blocked (S)-phenylalanine derivative of structure 2 can be prepared by reacting the appropriate (S)-phenylalanine derivative of structure 1 with phthalic anhydride in a suitable aprotic solvent, such as dimethylformamide.

In step b, the appropriate phthalimide blocked (S)-phenylalanine derivative of structure 2 can be converted to the corresponding acid chloride, then reacted with the appropriate amino acid methyl ester of structure 3 in a coupling reaction. For example, the appropriate phthalimide blocked (S)-phenylalanine derivative of structure 2 can be reacted with oxalyl chloride in a suitable aprotic solvent, such as methylene chloride. The resulting acid chloride can then be coupled with the appropriate amino acid methyl ester of structure 3 using N-methylmorpholine in a suitable aprotic solvent, such as dimethylformamide, to give the appropriate 1-oxo-3-phenylpropyl-amino acid methyl ester derivative of structure 4.

In step c, the hydroxymethylene functionality of the appropriate 1-oxo-3-phenylpropyl-amino acid methyl ester derivative of structure 4 can be oxidized to the appropriate aldehyde of structure 5 by oxidation techniques well known and appreciated in the art. For example, the hydroxymethylene functionality of the appropriate 1-oxo-3-phenylpropyl-amino acid methyl ester derivative of structure 4 can be oxidized to the appropriate aldehyde of structure 5 by means of a Swern oxidation using oxalyl chloride and dimethylsulfoxide in a suitable aprotic solvent, such as methylene chloride.

In step d, the appropriate aldehyde of structure 5 can be cyclized to the appropriate enamine of structure 6 by acid catalysis. For example, the appropriate aldehyde of structure 5 can be cyclized to the appropriate enamine of structure 6 by treatment with trifluroacetic acid in a suitable aprotic solvent, such as methylene chloride.

In step e, the appropriate enamine of structure 6 can be converted to the corresponding tricyclic compound of structure 7 by an acid catalyzed Friedel-Crafts reaction. For example, the appropriate enamine of structure 6 can be converted to the corresponding tricyclic compound of structure 7 by treatment with a mixture of trifluoromethane sulfonic acid and trifluoroacetic anhydride in a suitable aprotic solvent, such as methylene chloride.

In step f, the phthalimide protecting group of the appropriate tricyclic compound of structure 7 can be removed using techniques and procedures well known in the art. For example, the phthalimide protecting group of the appropriate tricyclic compound of structure 7 can be removed using hydrazine monohydrate in a suitable protic solvent such as methanol, to give the corresponding amino compound of structure 8.

In step g, the appropriate (S)-acetate compound of structure 10 can be prepared by reacting the appropriate amino compound of structure 8 with the appropriate S-acetate of structure 9. For example, the appropriate amino compound of structure 8 can be reacted with the appropriate (S)-acetate compound of structure 9 in the presence of a coupling reagent such as EEDQ (1-ethoxycarbonyl-2-ethoxy- 1,2-dihydroquinoline), DCC (1,3-dicyclohexylcarbodiimide), or diethylcyanophosponate in a suitable aprotic solvent, such as methylene chloride to give the appropriate (S)-acetoxy compound of structure 10.

Alternatively, the appropriate (S)-acetate compound of structure 10 can be prepared by reacting the appropriate amino compound of structure 8 with a preformed S-acetate activated ester. For example, the appropriate amino compound of structure 8 can be reacted with the appropriate preformed (S)-acetate activated ester to give the appropriate (S)-acetoxy compound of structure 10. Examples of suitable activated esters are N-hydroxysuccinimide, isobutylchloroformate, N-ethoxycarbonyl-2-ethoxy-1,3-dihydroquinoline (EEDQ), 1,1'-carbonyldiimidazole, 1-(3-dimethylaminopropyl)- 3-ethyl carbodiimide and the like.

In step h, the (S)-acetate functionality of the appropriate amide compound of structure 10 can be hydrolyzed to the corresponding (S)-alcohol of structure 11a with a base, such as lithium hydroxide in a suitable solvent mixture, such as tetrahydrofuran and ethanol.

In step i, the (S)-alcohol functionality of the appropriate amide compound of structure of 11a can be converted to the corresponding (R)-thioacetate or (R)-thiobenzoate of structure 12a. For example, the appropriate (S)-alcohol of structure 11a can be treated with thiolacetic acid in a Mitsunobu reaction using triphenylphosphine and DIAD (diisopropylazodicarboxylate) in a suitable aprotic solvent, such as tetrahydrofuran.

In step j, the (S)-alcohol functionality of the appropriate amide compound of structure 11a can be converted to the corresponding (R)-alcohol of structure 11b. For example, the appropriate (S)-alcohol of structure 11a can be treated with acetic acid in a Mitsunobu reaction using triphenylphosphine and DIAD in a suitable aprotic solvent, such as tetrahydrofuran. The resulting (R)-acetate can then be hydrolyzed with a base, such as lithium hydroxide.

In step k, the (R)-alcohol functionality of the appropriate amide compound of structure 11b can be converted to the corresponding (S)-thioacetate or (S)-thiobenzoate of structure 12b. For example, the appropriate (R)-alcohol of structure 11b can be treated with thiolacetic acid in a Mitsunobu reaction using triphenylphosphine and DIAD in a suitable aprotic solvent, such as tetrahydrofuran.

As summarized in Table 1, the $R_3$ and $R_4$ groups on the compounds of structures 12a and 12b can be manipulated using techniques and procedures well known and appreciated by one of ordinary skill in the art to give the corresponding compounds of structures 13a–18a and 13b–18b.

For example, the diphenylmethyl ester functionality of the appropriate compound of structure 12a can be removed using trifluoroacetic acid to give the appropriate carboxylic acid compound of structure 13a. Similarly, the diphenylmethyl ester functionality of the appropriate compound of structure 12b can be removed using trifluoroacetic acid to give the carboxylic acid compound of structure 13b.

The (R)-thioacetate or (R)-thiobenzoate functionality of the appropriate compound of structure 13a can be removed with lithium hydroxide in a suitable solvent mixture such as tetrahydrofuran and ethanol to give the appropriate (R)-thio compound of structure 14a. Similarly, the (S)-thioacetate or (S)-thiobenzoate functionality of the appropriate compound of structure 13b can be removed with lithium hydroxide in a suitable solvent mixture such as tetrahydrofuran and ethanol to give the appropriate (S)-thio compound of structure 14b.

Alternatively, the carboxylic acid functionality of the appropriate compound of structure 13a can be re-esterified using techniques and procedures well known and appreciated in the art. For example, a compound of structure 15a can be prepared by treating the carboxylic acid compound of structure 13a with the appropriate alkyl halide in a suitable aprotic solvent, such as dimethylformamide along with a non-nucleophilic base, such as cesium carbonate. Similarly, the carboxylic acid functionality of the appropriate compound of structure 13b can be esterified to the appropriate ester compound of structure 15b as described above for 15a.

The (R)-thioacetate or (R)-thiobenzoate functionalities of the appropriate compounds of structure 15a can be hydrolyzed to the corresponding (R)-thiol compounds of structure 16a with ammonia in a suitable protic solvent, such as methanol. Similarly, the (S)-thioacetate or (S)-thiobenzoate functionalities of the appropriate compounds of structure 15b can be hydrolyzed to the corresponding (S)-thiol compounds of structure 16b.

The thiol functionality of the appropriate compound of structure 14a can be alkylated using techniques and procedures well known and appreciated in the art. For example, a compound of structure 17a can be prepared by treating the thiol compound of structure 14a with the appropriate with chloromethyl pivalate in a suitable aprotic solvent, such as dimethylformamide along with a non-nucleophilic base, such as cesium carbonate. Similarly, the thio functionality of the appropriate compound of structure 14b can be alkylated to the appropriate pivalate compound of structure 17b as described above for 17a.

The thiol functionality of the appropriate compound of structure 16a can be alkylated using techniques and procedures well know and appreciated in the art. For example, a compound of structure 18a can be prepared by treating the thiol compound of structure 16a with the appropriate with chloromethyl pivalate as described above for the conversion of 14a to 17a. Similarly, the thiol functionality of the appropriate compound of structure 16b can be alkylated to the appropriate pivalate compound of structure 18b as described above for 18a.

TABLE 1

| | MANIPULATION OF $R_3$ AND $R_4$ | |
|---|---|---|
| Compound | $R_3$ | $R_4$ |
| 13a and 13b | COCH$_3$ or COPh | H |
| 14a and 14b | H | H |
| 15a and 15b | COCH$_3$ or COPh | C$_1$–C$_4$ alkyl, Ar—Y, |

TABLE 1-continued

MANIPULATION OF $R_3$ AND $R_4$

| Compound | $R_3$ | $R_4$ |
|---|---|---|
| 16a and 16b | H | $-CH_2OCOC(CH_3)_3$<br>$C_1-C_4$ alkyl,<br>Ar—Y,<br>diphenylmethyl,<br>$-CH_2OCOC(CH_3)_3$ |
| 17a and 17b | $-CH_2OCOC(CH_3)_3$ | H |
| 18a and 18b | $-CH_2OCOC(CH_3)_3$ | $C_1-C_4$ alkyl,<br>Ar—Y,<br>diphenylmethyl,<br>$-CH_2OCOC(CH_3)_3$ |

Although the general procedures outlined in Scheme A show the preparation of the compounds of Formula I wherein $A_1$ is (S)-COOR$_4$ and $A_2$ is hydrogen, the compounds of Formula I wherein $A_1$ is (R)-COOR$_4$ and $A_2$ is hydrogen may be prepared by analogous procedures by substituting an appropriate (R)-amino acid methyl ester for the (S)-amino acid methyl ester of structure 3 in step b.

Starting materials for use in the general synthetic procedures outlined in Scheme A are readily available to one of ordinary skill in the art. For example, certain (R)- and (S)-carboxy acetate or benzoate starting materials of structure 9 can be prepared by stereoselective reduction of the corresponding pyruvate compounds with alpine boranes as described in *J. Org. Chem.* 47, 1606 (1982), *J. Org. Chem.* 49, 1316 (1984), and *J. Am. Chem. Soc.* 106, 1531 (1984), followed by treating the resulting alcohol with acetic anhydride or benzoic anhydride to give the corresponding (R)- or (S)-carboxy acetate or benzoate compounds of structure 9.

Alternatively, certain tricyclic compounds of structure 7 may be prepared as described in European Patent Application of Flynn and Beight, Application #34533A EP (Jun. 11, 1987).

The following examples present typical syntheses as described in Scheme A. These examples are understood to be illustrative only and are not intended to limit the scope of the present invention in any way. As used herein, the following terms have the indicated meanings: "g" refers to grams; "mmol" refers to millimoles; "mL" refers to milliliters; "bp" refers to boiling point; "°C" refers to degrees Celsius; "mm Hg" refers to millimeters of mercury; "µL" refers to microliters; "µg" refers to micrograms; and "µM" refers to micromolar.

EXAMPLE 1

Preparation of [4S-[4α, 7α(R*), 12bβ]]-7-[(1-Oxo-2(R)-acetylthio-3-phenylpropyl)amino]-1,2,3,4,6,7,8,12b-octahydro-6-oxopyrido[2,1-a][2]benzazepine-4-carboxylic acid, diphenylmethyl ester Step a: N-phthaloyl-(S)-phenylalanine (2)

Mix phthalic anhydride (1.82 kgs, 12.3 mole), (S)-phenylalanine (1.84 kgs, 11.1 moles) and anhydrous dimethylformamide (2.26 L). Stir at 115°–120° C. for 2 hours under a nitrogen atmosphere. Pour into rapidly stirring water (32.6 L) and cool overnight at 0° C. Filter, wash with cold water (2×2L) and air dry. Dissolve in a mixture of 9A ethanol (8.05 L) and water (8.05 L) and heat at reflux temperature. Gravity filter, cool to ambient temperature and refrigerate overnight at about 0° C. Filter the crystallized product, wash with cold 50:50 9A ethanol/water (2×2L) and air dry to yield 2.96 kg (90.3%) of the title compound; mp 177°–179° C.

Step b: (S)-N-[2-(1,3-Dihydro-1,3-dioxo-2H-isoindol-2-yl)-1-oxo-3-phenylpropyl]-6-hydroxy-(S)-norleucine, methyl ester Mix N-phthaloyl-(S)-phenylalanine (2) (50.2 g, 0.17 mole), methylene chloride (660 mL) and dimethylformamide (0.5 mL) under a nitrogen atmosphere. Add oxalyl chloride (17.7 mL, 0.2 mole) over about 5 minutes with stirring. Stir at ambient temperature for 3 hours and evaporate the solvent in vacuo to leave N-phthaloyl-(S)-phenylalanine, acid chloride as a solid (54.3 g, 101.9%).

Mix 6-hydroxy-(S)-norleucine, methyl ester, hydrochloride salt (33.5 g, 0.1 mole) and dimethylformamide (201 mL), cool to about 0° C. and place under nitrogen atmosphere. Add by dropwise addition, N-methylmorpholine (51 mL, 0.46 mole) with cooling so that the pot temperature stays at 0°–5° C. Stir at 0°–5° C. for an additional 10 minutes, then add a solution of N-phthaloyl-(S)-phenylalanine, acid chloride (53.5 g, 0.17 mole) in methylene chloride (270 mL) over 30 minutes with cooling so that the temperature stays at 0°–5° C. Remove the cooling bath and stir at room temperature for 18 hours.

Evaporate the methylene chloride in vacuo and dilute the remaining residue with ethyl acetate (800 mL). Extract the resulting mixture with water (800 mL), separate the organic layer and extract with 1N hydrochloric acid (270 mL), followed by water (3×500 mL). Dry the organic layer (MgSO$_4$), filter and evaporate in vacuo to yield crude product (76 g, 98%). Dissolve the crude product in hot toluene (223.5 mL), cool to room temperature, than cool overnight at about 0° C. Filter the crystallized produce, wash with cold toluene and air dry to yield 56.6 g (76%) of the title compound; mp 128°–130° C.

Step c: 2-(1,3-Dihydro-1,3-dioxo-2H-isoindol-2-yl)-1-oxo-3-phenylpropyl-6-oxo-(S)-norleucine, methyl ester Mix oxalyl chloride (80 mL, 0.92 mole) and methylene chloride (2 L) and place under nitrogen atmosphere. Cool below –50° C. and add a solution of dimethyl sulfoxide (65.4 mL, 0.92 mole) in methylene chloride (425 mL). Stir for 15 minutes and add a solution of (S)-N-[2-(1,3-dihydro-1,3-dioxo-2H-isoindol-2-yl)-1-oxo-3-phenylpropyl]-6-hydroxy-(S)-norleucine, methyl ester (200 g, 0.456 mole) in methylene chloride (800 mL) over about 45 minutes, keeping the pot temperature below –50° C. for 30 minutes. Add triethylamine (420 mL, 3.01 mole) over 30 minutes. Stir while warming to 0° C. over 1.25 hours. Transfer the reaction mixture to a 12-liter flask. Stir and cool while adding a solution of OXONE (potassium peroxymonosulfate) (566 g) in water (6.74 L) at such a rate that the pot temperature stays below 15° C. Stir for 5 minutes, separate the organic layer and extract the aqueous layer with methylene chloride (1 L). Combine the organic phases, dry (MgSO$_4$) and filter to yield the title compound as a solution.

Step d: [S-(R*,R*)]-N-[2-(1,3-Dihydro-1,3-dioxo-2H-isoindol-2-yl)-1-oxo-3-phenylpropyl]-1,2,3,4-tetrahydro-2-pyridinecarboxylic acid, methyl ester Transfer the solution of 2-(1,3-dihydro-1,3-dioxo-2H-isoindol-2-yl)-1-oxo-3-phenylpropyl-6-oxo-(S)-norleucine, methyl ester in methylene chloride (volume about 4.5 L) to a 12-liter flask and place under nitrogen atmosphere. Stir and add trifluoroacetic acid (440 mL, 5.71 mole) in one portion. Stir the resulting mixture at room temperature for one hour, then rapidly cool to about 0° C. Add a solution of sodium hydroxide (240 g, 6.0 mole) in water (3.4 L) in a slow stream to the vigorously stirred mixture at such a rate that the pot temperature stays at about 0° C. Separate the organic phase and extract the aqueous phase with methylene chloride (1 L). Combine the organic phases and dry (MgSO$_4$). Filter and remove the solvent in vacuo to leave a residue (262 g, 137%).

Dissolve the above residue in diethyl ester (1 L) and wash with water (5×500 mL). Evaporate the organic phase in vacuo to leave a residue of 229 g. Dilute the residue with methylene chloride (200 mL) and purify by silica gel chromatography (methylene chloride) to yield a viscous residue of 225 g.

Dilute the above residue with diethyl ether (250 mL) and allow to stand at room temperature for 24 hours. Filter the solid, wash with diethyl ether, and air dry to yield 123.2 g; mp 140°–142.5° C. Recrystallize (methylene chloride (125 mL)/isopropanol (615 mL)) by boiling off the solvent until the pot temperature reaches 75° C. and allowing the resulting sample to stand at room temperature for 24 hours. Filter, wash with cold isopropanol and air dry to yield 101.5 g of the title compound; mp 144°–146° C.

Evaporate the filtrate from the 101.5 g in vacuo to yield 24 g. Recrystallize (isopropanol) to yield an additional 3.5 g of the title compound.

Evaporate the filtrate from the 123.2 g in vacuo to leave 62 g of oil. Purify by silica gel chromatography (25% ethyl acetate/75% hexane), collecting 21–500 mL fractions. Combine fraction 9–20 and evaporate in vacuo to yield 35 g of a viscous oil. Recrystallize three times (isopropanol/5 ml/g) to yield an additional 11.9 g of the title compound; mp 142.5°–144.5° C. Total yield of useful material: 116.9 g (61.3%).

Step e: [4S-[4α, 7α(R*), 12bβ]]-7-[(1,3-Dihydro-1,3-dioxo- 2H-isoindol-2-yl)]-1,2,3,4,6,7,8,12b-octahydro-6-oxopyrido-[2,1-a][2]benzazepine-4-carboxylic acid, diphenylmethyl ester Mix trifluoromethane sulfonic acid (500 g, 3.33 mole) and trifluoroacetic anhydride (74.8 mL, 0.53 mole) and place under nitrogen atmosphere. Stir and add a solution of [S-(R*,R*)]-N-[2-(1,3-dihydro-1,3-dioxo-2H-isoindol-2-yl)-1-oxo- 3-phenylpropyl]-1,2,3,4-tetrahydro-2-pyridinecarboxylic acid, methyl ester (200 g, 0.48 mole) in methylene chloride (1 L) with cooling at such a rate as to keep the pot temperature below 35° C. Stir at ambient temperature for 2 days. Pour into vigorously stirring ice water (5 L) and stir for 30 minutes. Extract with ethyl acetate (3×1 L), combine the organic phases and wash with water (3×500 mL). Evaporate in vacuo to a residue. Dissolve the residue in ethyl acetate (4 L) and extract with ¼ saturated potassium hydrogen carbonate (1 L), the ⅓ saturated potassium hydrogen carbonate (7×1 L). Combine the aqueous extracts and dilute with ethyl acetate (2 L). Stir the resulting mixture and cool to 5°–10° C. Adjust to pH 2 using concentrated hydrochloric acid (about 750 mL).

Separate the organic phase and extract the aqueous phase with ethyl acetate (3×1 L). Combine the ethyl acetate extracts, wash with water (3×1 L), then saturated sodium chloride (0.8 L), and dry (MgSO$_4$). Filter and wash with ethyl acetate (3×200 mL). Evaporate in vacuo to leave (1̲3̲3.3 g, 101.5%) [4S-[4α, 7α(R*), 12bβ]]-7-[(1,3-dihydro-1,3-dioxo-2H-isoindol-2-yl)]-1,2,3,4,6,7,8,12b-octahydro-6-oxopyrido[2,1-a][2]benzazepine-4-carboxylic acid as a colorless foam.

Dissolve [4S-[4α, 7α(R*), 12bβ]]-7-[(1,3-dihydro-1,3-dioxo- 2H-isoindol-2-yl)]-1,2,3,4,6,7,8,12b-octahydro-6-oxopyrido[2,1-a][2]benzazepine-4-carboxylic acid (113.9 g, 0.28 mole) in methylene chloride (1.2 L) and dry over anhydrous MgSO$_4$ (60 g). Filter and wash with methylene chloride (3×200 mL). Evaporate in vacuo to a residue. Dissolve the residue in anhydrous dimethylformamide (860 mL) and place under nitrogen atmosphere. Add cesium carbonate (98.9 g, 0.3 mole) in one portion. Stir for 45 minutes at ambient temperature. Add bromodiphenylmethane (164.8 g, 0.67 mole). Stir the resulting mixture at ambient temperature for 18 hours. Quench the reaction with ethyl acetate (2.464 L) and water (630 mL). Separate the organic phase and wash with water (7×625 mL), ¼ saturated potassium hydrogen carbonate (625 mL), water (625 mL), and saturated sodium chloride (625 mL). Dry (MgSO$_4$), filter and evaporate in vacuo to yield 214.4 g of an oil. Extract the combined aqueous washings with ethyl acetate (3×500 mL), wash with water (4×300 mL) and dry (MgSO$_4$). Filter and evaporate in vacuo to yield an additional 20.2 g of an oil.

Dissolve the crude product (234.6 g) in methylene chloride (200 mL) and plug filter through 213 g of silica gel, eluting with methylene chloride (2 L). Boil off the solvent and replace with hexane (3 L), with the pot temperature reaching a maximum of 65° C. Cool to ambient temperature, decant off the precipitated oil and crystallize (9A ethanol) to yield 96.6 g (60%) of the title compound; mp 153°–155° C.

Step f: [4S-[4α, 7α(R*), 12bβ]]-7-(Amino)- 1,2,3,4,6,7,8,12b-octahydro-6-oxopyrido[2,1-a][2]benzazepine-4-carboxylic acid, diphenylmethyl ester Mix [4S-[4α, 7α(R*), 12bβ]]-7-[(1,3-dioxo-2H-isoindol-2-yl)]-1,2,3,4,6,7,8,12b-octahydro-6-oxopyrido[2,1-a][2]benzazepine-4-carboxylic acid, diphenylmethyl ester (170.9 g, 0.3 mole), hydrazine monohydrate (34.4 g, 0.68 mole) and methanol (3.4 L) under nitrogen atmosphere. Heat at reflux for 5 hours. Cool to ambient temperature and filter to remove phthaloyl hydrazide. Evaporate the filtrate in vacuo to a residue and slurry in chloroform (600 mL). Remove insoluble phthaloyl hydrazide by filtration and wash with chloroform (4×210 mL). Wash the filtrate with water (4×429 mL), dry (MgSO$_4$), and filter. Evaporate the filtrate to a solid residue of the title compound weighing 142 g (107.7%).

Step g: [4S-[4α, 7α(R*), 12bβ]]-7-[(1-Oxo-2(S)-acetyloxy- 3-phenylpropyl)amino]-1,2,3,4,6,7,8,12b-octahydro-6-oxo-pyrido[2,1-a][2]benzazepine-4-carboxylic acid, diphenylmethyl ester Mix (S)-3-phenyllactic acid (11.17 g, 67.2 mmol) and sulfuric acid (0.3 mL of a 10% solution in acetic acid). Add acetic anhydride (6.34 mL, 67.2 mmol) over 10 minutes. Warm to 90° C. with stirring for 45 minutes. Allow to cool, pour into diethyl ether and wash with water three times. Separate the organic phase, dry (MgSO$_4$) and concentrate in vacuo to yield 13.16 g (94%) (S)-3-phenyl-2-acetyloxypropionic acid as a white oil.

Mix (S)-3-phenyl-2-acetyloxypropionic acid (3.6 g, 17 mmol) and [4S-[4α, 7α(R*), 12bβ]]-7-(amino)-1,2,3,4,6,7,8,12b-octahydro- 6-oxopyrido[2,1-a][2]benzazepine-4-carboxylic acid, diphenylmethyl ester (7.6 g, 17 mmol) in methylene chloride (50 mL). Add EEDQ (4.3 g, 17 mmol). Stir for 18 hours at ambient temperature under argon atmosphere. Extract with 2N hydrochloric acid, separate the organic phase, wash with water, then with saturated sodium hydrogen carbonate. Dry (MgSO$_4$) and concentrate in vacuo to yield an off-white foam. Purify by silica gel chromatography (30%, then 40%, then 50% ethyl acetate/hexane) to yield 8.5 g (78%) of the title compound.

Step h: [4S-[4α, 7α(R*), 12bβ]]-7-[(1-Oxo-2(S)-hydroxy- 3-phenylpropyl)amino]-1,2,3,4,6,7,8,12b-octahydro-6-oxo-pyrido[2,1-a][2]benzazepine-4-carboxylic acid, diphenylmethyl ester Dissolve [4S-[4α, 7α(R*), 12bβ]]-7-[(1-oxo-2(S)-acetyloxy- 3-phenylpropyl)amino]-1,2,3,4,6,7,8,12b-octahydro-6-oxo-pyrido[2,1-a][2]benzazepine-4-carboxylic acid, diphenylmethyl ester (11.0 g, 17.4 mmol) in ethanol (75 mL) and tetrahydrofuran (40 mL) and add lithium hydroxide (22 mL of a 1M solution, 22 mmol). Stir the reaction mixture for 2 hours. Remove the solvent in vacuo at 35° C. and partition the residue between ethyl acetate and 1N hydrochloric acid. Separate the organic phase, dry (MgSO$_4$), and concentrate in vacuo. Purify by silica gel chromatography (1:1/tetrahydrofuran:hexane) to yield 9.6 g (94%) of the title compound.

Anal. Calcd for $C_{37}H_{36}N_2O_5$: C, 75.49; H, 6.16; N, 4.76; Found: C, 75.30; H, 6.44; N, 4.54.

Step i: [4S-[4α, 7α(R*), 12bβ]]-7-[(1-Oxo-2(R)-acetylthio- 3-phenylpropyl)amino]-1,2,3,4,6,7,8,12b-octahydro-6-oxopyrido[2,1-a][2]benzazepine-4-carboxylic acid, diphenylmethyl ester Mix DIAD (3.4 g, 16.3 mmol), triphenylphosphine (4.28 g, 16.3 mmol) and anhydrous tetrahydrofuran (200 mL). Cool to 0° C. and stir for 30 minutes under nitrogen atmosphere. Add a solution of the [4S-[4α, 7α(R*), 12bβ]-7-[(1-oxo-2(S)-hydroxy- 3-phenylpropyl)amino]-1,2,3,4,6,7,8,12b-octahydro- 6-oxo-pyrido[2,1-a][2]benzazepine-4-carboxylic acid, diphenylmethyl ester (9.6 g, 16.3 mmol) and thioacetic acid (1.75 mL, 24.5 mmol) in anhydrous tetrahydrofuran (200 mL). Stir at 0° C. for 30 minutes, then allow to warm to ambient temperature. Remove the volatiles in vacuo and purify by silica gel chromatography (1 L each of 20%, 30%, 40% then 50% tetrahydrofuran/hexane) to yield 5.127 g (49%) of the title compound.

EXAMPLE 2

Preparation of [4S-[4α, 7α(R*), 12bβ]]-7-[(1-Oxo-2(R)-acetylthio-3-phenylpropyl)amino]-1,2,3,4,6,7,8,12b-octahydro-6-oxopyrido[1,2-a][2]benzazepine-4-carboxylic acid Mix [4S-[4α, 7α(R*), 12bβ]]-7-[(1-oxo-2(R)-acetylthio-3-phenylpropyl)amino]-1,2,3,4,6,7,8,12b-octahydro-6-oxo-pyrido[2,1-a][2]benzazepine-4-carboxylic acid, diphenylmethyl ester (3.125 g, 4.83 mmol), anisole (5 g) and trifluoracetic acid (30 mL). Stir for 2 hours at ambient temperature under nitrogen atmosphere. Remove the volatiles in vacuo and purify by silica gel chromatography (1400 mL 30% tetrahydrofuran/hexane with 5% acetic acid added, then 1000 mL 40% tetrahydrofuran/hexane with 5% acetic acid added) to yield a viscous foam. Dissolve the foam in a minimal amount of methylene chloride and dilute with hexane until cloudy. Allow to stand overnight at −30° C., filter the resulting white solid and dry at 56° C. under high vacuum to yield 2.079 g (89.53%) of the title compound.

EXAMPLE 3

Preparation of [4S-[4α, 7α(R*), 12bβ]]-7-[(1Oxo-2(R)-thio-3-phenylpropyl)amino]-1,2,3,4,6,7,8,12b-octahydro-6-oxo-pyrido[2,1-a][2]benzazepine-4-carboxylic acid Dissolve [4S-[4α, 7α(R*), 12bβ]]-7-[(1-oxo-2(R)-acetylthio- 3-phenylpropyl)amino]-1,2,3,4,6,7,8,12b-octahydro-6-oxo-pyrido[2,1-a][2]benzazepine-4-carboxylic acid (2.079 g, 4.33 mmol) in tetrahydrofuran (10 mL). Add to a solution of lithium hydroxide (20 mL of an 1N solution, 20 mmol) in methanol (60 mL, deoxygenated by bubbling with nitrogen for 10 minutes). Stir the cloudy solution for 40 minutes. Acidify and dilute the water until cloudy. Remove 10 mL of volatile solvent under high vacuum then dilute the mixture to 25 mL with water. Stir the mixture for 10 minutes, filter under a blanket of nitrogen, and partially suction dry under nitrogen atmosphere. Dry the solid overnight under high vacuum, then for 18 hours at 35° C. under high vacuum, 24 hours at 40° C., then 64 hours at 50° C. at 10 mm Hg.

In a second run, dissolve [4S-[4α, 7α(R*), 12bβ]]-7-[(1-oxo- 2(R)-acetylthio-3-phenylpropyl)amino]-1,2,3,4,6,7,8, 12b-octahydro- 6-oxo-pyrido[2,1-a][2]benzazepine-4-carboxylic acid (2.819 g, 5.87 mmol) in tetrahydrofuran (degassed). Add to a degassed solution of lithium hydroxide (27 mL of a 1N solution, 27 mmol) in methanol (80 mL). Stir at ambient temperature under nitrogen atmosphere for 45 minutes. Acidify with hydrochloric acid (15 mL of a 2N solution), dilute with water to 250 mL and stir for 15 minutes. Collect the solid by filtration under a blanket of nitrogen and wash with water. Dry for 2 hours at ambient temperature under high vacuum, then for 18 hours at 40° C. under high vacuum, then for 64 hours at 56° C. Combine materials for both runs to yield 3.955 g (88.5%) of the title compound.

EXAMPLE 4

Preparation of [4S-[4α,7α(R*), 12bβ]]-7-[(1-Oxo-2(R)-acetylthio-3-phenylpropyl)amino]-1,2,3,4,6,7,8,12b-octahydro-6-oxo-pyrido[2,1-a][2]benzazepine-4-carboxylic acid, benzyl ester Dissolve [4S-[4α, 7α(R*), 12bβ]]-7-[(1-oxo-2(R)-acetylthio- 3-phenylpropyl)amino]-1,2,3,4,6,7,8,12b-octahydro-6-oxo-pyrido[2,1-a][2]benzazepine-4-carboxylic acid (2.08 g, 4.33 mmol) in methylene chloride (25 mL) and dry over anhydrous MgSO$_4$. Filter and wash with methylene chloride (3×200 mL). Evaporate in vacuo to a residue. Dissolve the residue in anhydrous dimethylformamide (25 mL) and place under nitrogen atmosphere. Add cesium carbonate (1.65 g, 5.0 mmole) in one portion. Stir for 45 minutes at ambient temperature. Add benzyl bromide (550 mg, 5.0 mmol). Stir the resulting mixture at ambient temperature for 18 hours. Quench the reaction with ethyl acetate (50 mL) and water (50 mL). Separate the organic phase and wash with water (7×50 mL), ¼ saturated potassium hydrogen carbonate (50 mL), water (50 mL), and saturated sodium chloride (50 mL). Dry (MgSO$_4$), filter and evaporate in vacuo to yield the title compound.

EXAMPLE 5

Preparation of [4S-[4α, 7α(R*), 12bβ]]-7-[(1-Oxo-2(R)-thio-3-phenylpropyl)amino]-1,2,3,4,6,7,8,12b-octahydro-6-oxo-pyrido-[2,1-a][2]benzazepine-4-carboxylic acid, benzyl ester Stir [4S-[4α, 7α(R*), 12bβ]]-7-[(1-oxo-2(R)-acetylthio-3-phenylpropyl)amino]-1,2,3,4,6,7,8,12b-octahydro-6-oxo-pyrido[2,1-a][2]benzazepine-4-carboxylic acid, benzyl ester (2.28 g, 4 mmol) and saturated methanolic ammonia at ambient temperature until hydrolysis is complete. Evaporate the solvent in vacuo and purify by silica gel chromatography to give the title compound.

EXAMPLE 6

Preparation of [4S-[4α, 7α(R*), 12bβ]]-7-[(1-Oxo-2(S)-acetylthio-3-phenylpropyl)amino]-1,2,3,4,6,7,8,12b-octahydro-6-oxo-pyrido[2,1-a][2]benzazepine-4-carboxylic acid, diphenylmethyl ester Step j: [4S-[4α, 7α(R*), 12bβ]]-7-[(1Oxo-2(R)-hydroxy-3-phenylpropyl)amino]-1,2,3,4,6,7,8,12b-octahydro-6-oxo-pyrido[2,1-a][2]benzazepine-4-carboxylic acid, diphenylmethyl ester Dissolve [4S-[4α, 7α(R*), 12bβ]]-7-[(1-oxo-2(S)-hydroxy- 3-phenylpropyl)amino]-1,2,3,4,6,7,8,12b-octahydro-6-oxopyrido[2,1-a][2]benzazepine-4-carboxylic acid, diphenylmethyl ester (59 mg, 0.1 mmol), triphenylphosphine (39 mg, 0.15 mmol) and acetic acid (8.7 μL, 0.15 mmol) in anhydrous tetrahydrofuran (3 mL). Treat with DIAD (32 mg, 0.15 mmol) at 0° C. Stir for 5 minutes at 0° C., then allow to stir at ambient temperature for 45 minutes. Remove the volatiles in vacuo and purify the residue by silica gel chromatography (3:1/hexane:tetrahydrofuran) to yield 67 mg (106%) [4S-[4α, 7α(R*), 12bβ]]-7-[(1-oxo-2(R)-acetyloxy- 3-phenylpropyl)amino]-1,2,3,4,6,7,8,12b-octahydro-6-oxo-pyrido[2,1-a][2]benzazepine-4-carboxylic acid, diphenylmethyl ester.

Dissolve [4S-[4α, 7α(R*), 12bβ]]-7-[(1-oxo-2(R)-acetyloxy- 3-phenylpropyl)amino]-1,2,3,4,6,7,8,12b-octahydro-6-oxo-pyrido[2,1-a][2]benzazepine-4-carboxylic acid, diphenylmethyl ester (366 mg, 0.58 mmol) in methanol (5 mL) and tetrahydrofuran (5 mL) and add lithium hydroxide (0.8 mL of a 1M solution, 0.8 mmol). Stir the reaction mixture for 2 hours and remove the solvent in vacuo. Acidify and partition between methylene chloride and water. Separate the organic phase, dry (MgSO₄) and concentrate in vacuo to yield a white foam.

In another run, dissolve [4S-[4α, 7α(R*), 12bβ]]-7-[(1-oxo- 2(R)-acetyloxy-3-phenylpropyl)amino]-1,2,3,4,6,7,8,12b-octahydro- 6-oxo-pyrido[2,1-a][2]benzazepine-4-carboxylic acid, diphenylmethyl ester (100 mg, 0.16 mmol) in methanol (5 mL) and tetrahydrofuran (5 mL) and add lithium hydroxide (0.2 mL of a 1M solution, 0.2 mmol). Stir the reaction mixture for 1 hour, dilute with water (50 mL), make acidic and extract with diethyl ether (50 mL). Separate the organic phase, wash with water (2×50 mL), dry (MgSO₄) and concentrate in vacuo.

Combine the material from both runs and purify by silica gel chromatography (30%, then 50% tetrahydrofuran/hexane) to yield 355 mg (85%) of the title compound as a white foam.

Step k: [4S-[4α, 7α(R*), 12bβ]]-7-[(1-Oxo-2(S)-acetylthio- 3-phenylpropyl)amino]-1,2,3,4,6,7,8,12b-octahydro-6-oxo-pyrido[2,1-a][2]benzazepine-4-carboxylic acid, diphenylmethyl ester Mix DIAD (31 mg, 0.15 mmol), triphenylphosphine (39 mg, 0.16 mmol) and anhydrous tetrahydrofuran (2 mL). Cool to 0° C. and stir for 30 minutes under an argon atmosphere. Add the [4S-[4α, 7α(R*), 12bβ]]-7-[(1-oxo- 2(R)-hydroxy-3-phenylpropyl)amino]- 1,2,3,4,6,7,8,12b-octahydro-6-oxo-pyrido[2,1-a][2]benzazepine-4-carboxylic acid, diphenylmethyl ester (59 mg, 0.1 mmol) as a solid, then immediately add thiolacetic acid (11 μL, 0.15 mmol). Allow the reaction to warm to ambient temperature and stir overnight. Remove the solvent in vacuo and purify the residue by silica gel chromatography (40% ethyl acetate/hexane then 50% ethyl acetate/hexane) to yield 51 mg of the title compound.

EXAMPLE 7

Preparation of [4S-[4α, 7α(R*), 12bβ]]-7-[(1-Oxo-2(S)-acetylthio-3-phenylpropyl)amino]-1,2,3,4,6,7,8,12b-octahydro-6-oxo-pyrido[2,1-a][2]benzazepine-4-carboxylic acid Dissolve [4S-[4α, 7α(R*), 12bβ]]-7-[(1-oxo-2(S)-acetylthio- 3-phenylpropyl)amino]-1,2,3,4,6,7,8,12b-octahydro-6-oxo-pyrido[2,1-a][2]benzazepine-4-carboxylic acid, diphenylmethyl ester (51 mg, 0.079 mmol) in anisole (4 drops) and trifluoroacetic acid (1 mL) under argon atmosphere at ambient temperature. Allow to stand for 45 minutes, remove the trifluoroacetic acid in vacuo and purify by silica gel chromatography (50 mL of 40% ethyl acetate/hexane then 50 mL of 40% ethyl acetate/hexane with 5% acetic acid added) to yield 30 mg (74%) of the title compound.

EXAMPLE 8

Preparation of [4S-[4α, 7α(R*), 12bβ]]-7-[(1-Oxo-2(S)-thio-3-phenylpropyl)amino]-1,2,3,4,6,7,8,12b-octahydro-6-oxo-pyrido[2,1-a][2]benzazepine-4-carboxylic acid Dissolve [4S-[4α, 7α(R*), 12bβ]]-7-[(1-oxo-2(S)-acetylthio- 3-phenylpropyl)amino]-1,2,3,4,6,7,8,12b-octahydro-6-oxo-pyrido[2,1-a][2]benzazepine-4-carboxylic acid (57 mg, 0.12 mmol) in deoxygenated methanol (3 mL) plus 1N lithium hydroxide (0.25 mL, 0.25 mmol). Stir for 30 minutes under argon atmosphere at ambient temperature. Reduce in volume to 1.5 mL in vacuo, then add, by dropwise addition, to a rapidly stirring solution of 2N hydrochloric acid (2 mL). Collect the resulting precipitate, wash with water and dry in a vacuum dessicator for 1 hour. Dry at 35° C. overnight to yield 30 mg (58%) of the title compound as a white electrostatic powder.

EXAMPLE 9

Preparation of [4S-[4α, 7α(R*), 12bβ]]-7-[(1-Oxo-2(S)-acetylthio-3-phenylpropyl)amino]-1,2,3,4,6,7,8,12b-octahydro-6-oxo-pyrido[2,1-a][2]benzazepine-4-carboxylic acid, pivaloyloxymethyl ester Dissolve [4S-[4α, 7α(R*), 12bβ]]-7-[(1-oxo-2(S)-acetylthio- 3-phenylpropyl)amino]-1,2,3,4,6,7,8,12b-octahydro-6-oxo-pyrido[2,1-a][2]benzazepine-4-carboxylic acid (2.08 g, 4.33 mmol) in methylene chloride (25 mL) and dry over anhydrous MgSO₄. Filter and wash with methylene chloride (3×200 mL). Evaporate in vacuo to a residue. Dissolve the residue in anhydrous dimethylformamide (25 mL) and place under nitrogen atmosphere. Add cesium carbonate (1.65 g, 5.0 mmole) in one portion. Stir for 45 minutes at ambient temperature. Add chloromethyl pivalate (753 mg, 5.0 mmol). Stir the resulting mixture at ambient temperature for 18 hours. Quench the reaction with ethyl acetate (50 mL) and water (50 mL). Separate the organic phase and wash with water (7×50 mL), ¼ saturated potassium hydrogen carbonate (50 mL), water (50 mL), and saturated sodium chloride (50 mL). Dry (MgSO₄), filter and evaporate in vacuo to yield the title compound.

EXAMPLE 10

Preparation of [4S-[4α, 7α(R*), 12bβ]]-7-[(1-Oxo-2(S)-thio-3-phenylpropyl)amino]-1,2,3,4,6,7,8,12b-octahydro-6-oxo-pyrido[2,1-a][2]benzazepine-4-carboxylic acid, pivaloyloxymethyl ester Stir [4S-[4α, 7α(R*), 12bβ]]-7-[(1-oxo-2(S)-acetylthio-3-phenylpropyl)amino]-1,2,3,4,6,7,8,12b-octahydro-6-oxo-pyrido[2,1-a][2]benzazepine-4-carboxylic acid pivaloyloxymethyl ester (2.38 g, 4 mmol) and saturated methanolic ammonia at ambient temperature until hydrolysis is complete. Evaporate the solvent in vacuo and purify by silica gel chromatography to give the title compound.

The following compounds can be prepared by procedures analogous to those described above in Examples 1–10:

[4S-[4α, 7α(R*), 12bβ]]-7-[(1-oxo-2(R)-benzoylthio-3-phenylpropyl)amino]- 1,2,3,4,6,7,8,12b-octahydro-6-oxopyrido[2,1-a][2]benzazepine-4-carboxylic acid, diphenylmethyl ester;

[4S-[4α, 7α(R*), 12bβ]]-7-[(1-oxo-2(R)-benzoylthio-3-phenylpropyl)amino]- 1,2,3,4,6,7,8,12b-octahydro-6-oxopyrido[2,1-a][2]benzazepine-4-carboxylic acid;

[4S-[4α, 7α(R*), 12bβ]]-7-[(1-oxo-2-thio-ethyl)amino]-1,2,3,4,6,7,8,12b-octahydro-6-oxo-pyrido[2,1-a][2]benzazepine-4-carboxylic acid;

[4S-[4α, 7α(R*), 12bβ]]-7-[(1-oxo-2(R)-benzoylthio-3-phenylpropyl)amino]- 1,2,3,4,6,7,8,12b-octahydro-6-oxo-pyrido[2,1-a][2]benzazepine-4-carboxylic acid, benzyl ester;

[4S-[4α, 7α(R*), 12bβ]]-7-[(1-oxo-2-thio-ethyl)amino]-1,2,3,4,6,7,8,12b-octahydro-6-oxo-pyrido[2,1-a][2]benzazepine-4-carboxylic acid, benzyl ester;

[4S-[4α, 7α(R*), 12bβ]]-7-[(1-oxo-2(S)-benzoylthio-3-phenylpropyl)amino]- 1,2,3,4,6,7,8,12b-octahydro-6-oxo-pyrido[2,1-a][2]benzazepine-4-carboxylic acid, diphenylmethyl ester;

[4S-[4α, 7α(R*), 12bβ]]-7-[(1-oxo-2(S)-benzoylthio-3-phenylpropyl)amino]- 1,2,3,4,6,7,8,12b-octahydro-6-oxo-pyrido[2,1-a][2]benzazepine-4-carboxylic acid;

[4S-[4α, 7α(R*), 12bβ]]-7-[(1-oxo-2(S)-benzoylthio-3-phenylpropyl)amino]- 1,2,3,4,6,7,8,12b-octahydro-6-oxo-pyrido[2,1-a][2]benzazepine-4-carboxylic acid, benzyl ester;

[4R-[4β, 7α(R*), 12bβ]]-7-[(1-oxo-2-benzoylthio-ethyl)amino]- 1,2,3,4,6,7,8,12b-octahydro-6-oxo-pyrido[2,1-a][2]benzazepine-4-carboxylic acid;

[4S-[4α, 7α(R*), 12bβ]]-7-[(1-oxo-2-thio-2-phenylethyl)amino]- 1,2,3,4,6,7,8,12b-octahydro-6-oxo-pyrido[2,1-a][2]benzazepine-4-carboxylic acid;

The compounds of Formula (I) wherein $A_1$ is hydrogen and $A_2$ is —$COOR_4$ can be prepared by utilizing procedures and techniques well known and appreciated by one of ordinary skill in the art. A general synthetic scheme for the preparation of appropriate starting materials for these compounds is set forth in Scheme B wherein all substituents, unless otherwise indicated, are previously defined.

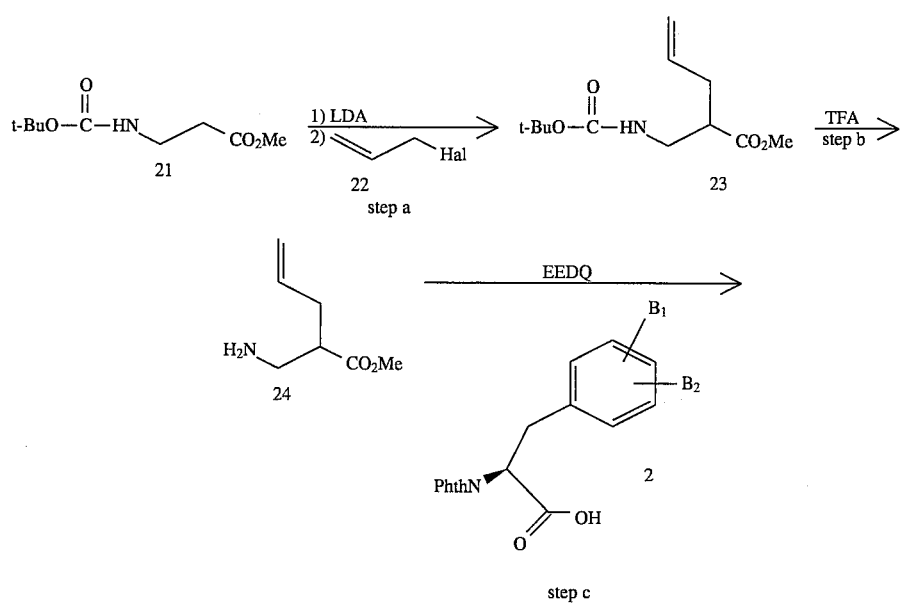

Scheme B

-continued
Scheme B

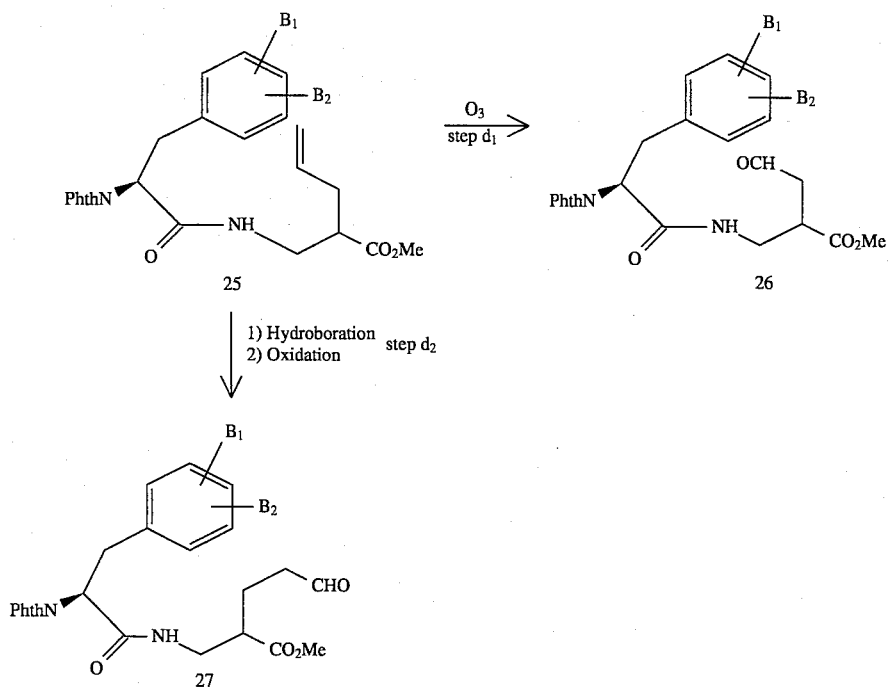

Scheme B provides a general synthetic procedure for preparing the compounds of Formula (I) wherein $A_1$ is hydrogen and $A_2$ is —$COOR_4$.

In step a, N-(t-butyloxycarbonyl)-β-alanine methyl ester (21) can be treated with two equivalents of a non-nucleophillic base, such as lithium diisopropylamide, in a suitable aprotic solvent, such as tetrahydrofuran, followed by addition of an allyl halide of structure 22 to give 2-(2-propenyl)-N-(t-butyloxycarbonyl)-β-alanine methyl ester (23).

In step b, the t-butyloxycarbonyl-amino functionality of 2-(2-propenyl)-N-(t-butyloxycarbonyl)-β-alanine methyl ester (23) can be hydrolyzed under acidic conditions, such as with trifluoroacetic acid in a suitable aprotic solvent, such as methylene chloride to give 2-(2-propenyl)-β-alanine methyl ester (24).

In step c, the appropriate amide compound of structure 25 can be prepared by reacting the appropriate phthalimide protected (S)-phenylalanine compound of structure 2 (described previously in Scheme A) with 2-(2-propenyl)-β-alanine methyl ester (24) under coupling reaction conditions, such as with EEDQ, in a suitable aprotic solvent, such as methylene chloride.

In step $d_1$, the olefin functionality of the appropriate amide compound of structure 25 can be converted to the appropriate aldehyde compound of structure 26 under conditions of oxidative cleavage, such as treatment with ozone in a suitable solvent mixture, such as methylene chloride and methanol.

Alternatively, in step $d_2$, the olefin functionality of the appropriate amide compound of structure 25 can be converted to the appropriate aldehyde compound of structure 27 by first subjecting to hydroboration, followed by oxidation. For example, the olefin functionality of the appropriate amide compound of structure 25 can be hydroborated with 9-borabicyclo[3.3.1]nonane (9-BBN) in a suitable aprotic solvent, such as tetrahydrofuran. The hydroborated olefin can than be oxidized under techniques and procedures well known and appreciated in the art, such as treatment with sodium hydroxide and hydrogen peroxide to give the alcohol, followed by Swern oxidation, using oxalyl chloride and methyl sulfoxide in a suitable aprotic solvent, such as methylene chloride.

The compounds of Formula (I) wherein $A_1$ is hydrogen, $A_2$ is —$COOR_4$, $R_3$ is acetate or benzoate, $R_4$ is methyl, and n=0 can be prepared from an appropriate aldehyde of structure 26 in a process as outlined previously in Scheme A, steps d–k.

The compounds of Formula (I) wherein $A_1$ is hydrogen, $A_2$ is —$COOR_4$, $R_3$ is acetate or benzoate, $R_4$ is methyl, and n=1 can be prepared from an appropriate aldehyde of structure 27 in a process as outlined previously in Scheme A, Steps d–k.

The groups $R_3$ and $R_4$ may be manipulated by techniques and procedures well known and appreciated in the art and described previously in Scheme A and Table 1.

Starting materials for use in the general synthetic procedures outlines in Scheme B are readily available to one of ordinary skill in the art and described previously in Schemes A.

The following examples present typical syntheses as described in Scheme B. These examples are understood to be illustrative only and are not intended to limit the scope of the present invention in any way.

EXAMPLE 11

Preparation of [6α(R*), 11bβ]-6-[(S)-(1-Oxo-2(R)-acetylthio-3-phenylpropyl)amino]-1,2,3,5,6,7,11b-heptahydro-5-oxo-pyrrolo[2,1-a][2]benzazepine-2(R)-carboxylic acid, methyl ester Step a: N-(t-Butyloxycarbonyl)-2-(2-propenyl)-β-alanine, methyl ester Dissolve diisopropylamine (5.6 mL, 40 mmol) in anhydrous tetrahydrofuran, cool to −78° C. and place under nitrogen atmosphere. Treat with n-butyllithium (25 mL of a 1.6M solution in hexane, 40 mmol). Stir for 30 minutes and add, by dropwise addition, a solution of N-(t-butyloxycarbonyl)-β-alanine methyl ester (4.06 g, 20 mmol) in tetrahydrofuran (25 mL) over 20 minutes. Stir for an additional 30 minutes. Add allyl bromide (1.72 mL, 20 mmol) and allow the mixture to warm to room temperature with stirring until homogeneous. Cool to −78° C. and slowly warm to −20° C. over 30 minutes. Pour into 5% hydrochloric acid, extract into ether, wash with saturated sodium chloride, dry, and concentrate to yield 5.01 g yellow oil. Purify by silica gel chromatography (25% ethyl acetate/hexane) to yield 4.2 g (87%) of a racemic mixture of the title compound as a clear colorless oil.

Step b: 2-(2-Propenyl)-β-alanine, methyl ester

Dissolve N-(t-butyloxycarbonyl)-2-(2-propenyl)-β-alanine, methyl ester (5.6 g, 23.0 mmol) in methylene chloride (25 mL) and treat with trifluoroacetic acid (15 mL). Stir for three hours and remove the volatiles in vacuo. Treat the residue with water, make basic with sodium hydroxide (1.0 g, 25 mmol) and extract with ethyl acetate. Separate the organic phase and dry ($Na_2SO_4$). Evaporate to give 4.0 g of the title compound as an oil in ethyl acetate.

Step c: (S)-N-[2-(1,3-Dihydro-1,3-dioxo-2H-isoindol-2-yl)- 1-oxo-3-phenylpropyl]-2-(2-propenyl)-β-alanine, methyl esters Stir a solution of N-phthaloyl-(S)-phenylalanine (7.5 g, 25 mmol) and EEDQ (7.0 g, 28 mmol) in methylene chloride (50 mL). Add crude 2-(2-propenyl)-β-alanine, methyl ester (4.0 g, 23 mmol) and stir under nitrogen atmosphere for 2.5 days. Pour into ethyl acetate, wash with 10% hydrochloric acid (2×200 mL), and saturated sodium hydrogen carbonate. Dry ($MgSO_4$) and concentrate. Treat the residue with ethyl acetate, dilute with hexane and allow to crystallize. Remove the solid to yield 5.33 g (55%) of the diastereomeric title compounds as a white powder; mp 133°–5° C.

Anal. Calcd for $C_{24}H_{24}N_2O_5$: C, 68.56; H, 5.75; N, 6.66; Found: C, 68.32; H, 5.81; N, 6.47.

Step $d_1$: (S)-N-[2-(1,3-Dihydro-1,3-dioxo-2H-isoindol-2-yl)]-(S)-phenylalanyl]- 2-(2-oxoethyl)-β-alanine, methyl esters Dissolve the diastereomeric (S)-N-[2-(1,3-dihydro-1,3-dioxo- 2H-isoindol-2-yl)-1-oxo-3-phenylpropyl]-2-(2-propenyl)-β-alanine, methyl esters (4.2 g, 10 mmol) in methylene chloride (150 mL) and methanol (25 mL). Cool to −70° C. and treat with ozone until a blue color persists. Add dimethyl sulfide (7 mL) and pyridine (2 mL) and allow the solution to warm to 25° C., then stir for 18 hours. Dilute the solution with methylene chloride, wash with 10% hydrochloric acid, dry ($MgSO_4$) and concentrate to yield 4.5 g of the title compound as a foam.

Scheme A, Step d: (S)-N-[2-(1,3-Dihydro-1,3-dioxo-2H-isoindol- 2-yl)]-1-oxo-3-phenylpropyl-1,2,3-trihydro-3-pyrrolecarboxylic acid, methyl esters Mix the (S)-N-[2-(1,3-dihydro-1,3-dioxo-2H-isoindol-2-yl)]-(S)- 1-oxo-3-phenylpropyl]-2-(2-oxoethyl)-β-alanine, methyl esters (4.5 g), methylene chloride (150 mL) and trifluoroacetic acid (0.5 mL). Reflux for 8 hours and purify by silica gel chromatography (50% ethyl acetate/hexane) to yield 3.5 g (87%) of the title compound.

Scheme A, Step e: [6α(R*), 11bβ]-6-[(S)-(1,3-Dihydro-1,3-dioxo- 2H-isoindol-2-yl)]-1,2,3,5,6,7,11b-heptahydro-5-oxo-pyrrolo[2,1-a][2]benzazepine-2(R)-carboxylic acid, methyl ester and [6α(R*), 11bβ]-6-[(S)-(1,3-Dihydro-1,3-dioxo-2H-isoindol- 2-yl)]-1,2,3,5,6,7,11b-heptahydro-5-oxo-pyrrolo[2,1-a][2]benzazepine-2(S)-carboxylic acid, methyl ester Place trifluromethane-sulfonic acid (10 mL) in a flask under nitrogen atmosphere at 25° C. Ad (S)-N-[2-(1,3-dihydro-1,3-dioxo- 2H-isoindol-2-yl)]-1-oxo-3-phenylpropyl-1,2,3-trihydro- 3-pyrrolecarboxylic acid, methyl esters (2.5 g, 6 mmol) in methylene chloride (10 mL). Stir the mixture for 6 hours, pour into water and extract with ethyl acetate. Wash well with water, dry ($MgSO_4$) and concentrate to yield 2.3 g foam. An additional 1.0 g foam can be obtained by treating (S)-N-[2-(1,3-dihydro-1,3-dioxo-2H-isoindol-2-yl)]-1-oxo-3-phenylpropyl- 1,2,3-trihydro-3-pyrrolecarboxylic acid, methyl ester (1.0 g, from a second crop of the above experiment) with trifluromethane-sulfonic acid (5 mL) in methylene chloride (5 mL), stirring under nitrogen atmosphere for 6 hours, and working-up as described above.

Combine both products, concentrate and allow to stand for 2 days. Take up the crude product in ethyl acetate to form a solid. Dilute with hexane and filter to yield 1.85 g solid. Recrystallize (50 mL hot ethyl acetate to 1:1 ethyl acetate/hexane) to yield 1.37 g of the 2(R)-carboxylic acid title compound as colorless needles; mp 199°–200° C.

Anal. Calcd for $C_{23}H_{20}N_2O_5$: C, 68.31; H, 4.98; N, 6.93; Found: C, 68.01; H, 5.06; N, 6.80.

Purify the mother liquors by chromatography to give the 2(S)-carboxylic acid title compound.

Scheme A, Step f: [6α(R*), 11bβ]-6-[(S)-Amino]- 1,2,3,5,6,7,11b-heptahydro-5-oxo-pyrrolo[2,1-a][2]benzazepine-2(R)-carboxylic acid, methyl ester Mix [6α(R*), 11bβ]-6-[(S)-(1,3-dihydro-1,3-dioxo-2H-isoindol- 2-yl)]-1,2,3,5,6,7,11b-heptahydro-5-oxo-pyrrolo[2,1-a][2]benzazepine-2(R)-carboxylic acid, methyl ester (1.37 g, 3.38 mmol)), hydrazine monohydrate (389 mg, 7.7 mmol)) and methanol (38 mL) under nitrogen atmosphere. Heat at reflux for 5 hours. Cool to ambient temperature and filter to remove phthaloyl hydrazide. Evaporate the filtrate in vacuo to a residue and slurry in chloroform (60 mL). Remove insoluble phthaloyl hydrazide by filtration and wash with chloroform (4×21 mL). Wash the filtrate with water (4×50 mL), dry ($MgSO_4$), and filter. Evaporate the filtrate to give the title compound.

Scheme A, Step g: [6α(R*), 11bβ]-6-[(S)-(1-Oxo-2(S)-acetyloxy- 3-phenylpropyl)amino]-1,2,3,5,6,7,11b-heptahydro- 5-oxo-pyrrolo[2,1-a][2]benzazepine-2(R)-carboxylic acid, methyl ester Mix (S)-3-phenyl-2-acetyloxypropionic acid (3.6 g, 17 mmol) and [6α(R*), 11bβ]-6-[(S)-amino]-1,2,3,5,6,7,11b-heptahydro- 5-oxo-pyrrolo[2,1-a][2]benzazepine-2(R)-carboxylic acid, methyl ester (4.64 g, 17 mmol) in methylene chloride (50 mL). Add EEDQ (4.3 g, 17 mmol). Stir for 18 hours at ambient temperature under argon atmosphere. Extract with 2N hydrochloric acid, separate the organic phase, wash with water, then with saturated sodium hydrogen carbonate. Dry ($MgSO_4$), concentrate in vacuo and purify by silica gel chromatography to give the title compound.

Scheme A, Step h: [6α(R*), 11bβ]-6-[(S)-(1-Oxo-2(S)-hydroxy- 3-phenylpropyl)amino]-1,2,3,5,6,7,11b-heptahydro-5-oxo-pyrrolo[2,1-a][2]benzazepine-2(R)-carboxylic acid, methyl ester Dissolve [6α(R*), 11bβ]-6-[(S)-(1-oxo-2(S)-acetyloxy-3-phenylpropyl)amino]- 1,2,3,5,6,7,11b-heptahydro-5-oxo-pyrrolo[2,1-a][2]benzazepine-2(R)-carboxylic acid, methyl ester (7.87 g, 17.4 mmol) in ethanol (75 mL) and tetrahydrofuran (40 mL) and add lithium hydroxide (22 mL of a 1M solution, 22 mmol). Stir the reaction mixture for 2 hours. Remove the solvent in vacuo at 35° C. and partition the residue between ethyl acetate and 1N hydrochloric acid. Separate the organic phase, dry (MgSO$_4$), and concentrate in vacuo and treat with diazomethane. Purify by silica gel chromatography to give the title compound.

Scheme A, Step i: [6α(R*), 11bβ]-6-[(S)-(1-Oxo-2(R)-acetylthio- 3-phenylpropyl)amino]-1,2,3,5,6,7,11b-heptahydro- 5-oxo-pyrrolo[2,1-a][2]benzazepine-2(R)-carboxylic acid, methyl ester Mix DIAD (3.4 g, 16.3 mmol), triphenylphosphine (4.28 g, 16.3 mmol) and anhydrous tetrahydrofuran (200 mL). Cool to 0° C. and stir for 30 minutes under nitrogen atmosphere. Add a solution of [6α(R*), 11bβ]-6-[(S)-(1-oxo-2-(S)-hydroxy-3-phenylpropyl)amino]- 1,2,3,5,6,7,11b-heptahydro-5-oxo-pyrrolo[2,1-a][2]benzazepine-2(R)-carboxylic acid, methyl ester (6.7 g, 16.3 mmol) and thiolacetic acid (1.75 mL, 24.5 mmol) in anhydrous tetrahydrofuran (200 mL). Stir at 0° C. for 30 minutes, then allow to warm to ambient temperature. Remove the volatiles in vacuo and purify by silica gel chromatography to give the title compound.

EXAMPLE 12

Preparation of [6α(R*), 11bβ]-6-[(S)-(1-Oxo-2(R)-thio-3-phenylpropyl)amino]- 1,2,3,5,6,7,11b-heptahydro-5-oxo-pyrrolo[2,1-a][2] benzazepine-2(R)-carboxylic acid Dissolve [6α(R*), 11bβ]-6-[(S)-(1-oxo-2(R)-acetylthio-3-phenylpropyl)amino]- 1,2,3,5,6,7,11b-heptahydro-5-oxo-pyrrolo[2,1-a][2]benzazepine-2(R)-carboxylic acid, methyl ester (56 mg, 0.12 mmol) in deoxygenated methanol (3 mL) plus 1N lithium hydroxide (0.50 mL, 0.50 mmol). Stir for 30 minutes under argon atmosphere at ambient temperature. Reduce in volume to 1.5 mL in vacuo, then add, by dropwise addition, to a rapidly stirring solution of 2N hydrochloric acid (2 mL). Collecting the resulting precipitate, wash with water and dry in a vacuum dessicator for 1 hour. Dry at 35° overnight to give the title compound.

EXAMPLE 13

Preparation of [6α(R*), 11bβ]-6-[(S)-(1-Oxo-2(R)-acetylthio-3-phenylpropyl)amino]-1,2,3,5,6,7,11b-heptahydro-5-oxo-pyrrolo[2,1-a][2]benzazepine-2(R)-carboxylic acid Mix [6α(R*), 11bβ]-6-[(S)-(1-oxo-2(R)-thio-3-phenylpropyl)amino]- 1,2,3,5,6,7,11b-heptahydro-5-oxo-pyrrolo[2,1-a][2]benzazepine-2(R)-carboxylic acid (51 mg, 0.12 mmol) and sulfuric acid (0.3 mL of a 10% solution in acetic acid). Add acetic anhydride (11 mg, 0.12 mmol) over 10 minutes. Warm to 90° C. with stirring for 45 minutes. Allow to cool, pour into diethyl ether and wash with water three times. Separate the organic phase, dry (MgSO$_4$) and concentrate in vacuo. Purify by silica gel chromatography to yield the title compound.

EXAMPLE 14

Preparation of [6α(R*), 11bβ]-6-[(S)-(1-Oxo-2(R)-acetylthio-3-phenylpropyl)amino]-1,2,3,5,6,7,11b-heptahydro-5-oxo-pyrrolo[2,1-a][2]benzazepine-2(R)-carboxylic acid, benzyl ester Dissolve [6α(R*), 11bβ]-6-[(S)-(1-oxo-2(R)-acetylthio-3-phenylpropyl)amino]- 1,2,3,5,6,7,11b-heptahydro-5-oxo-pyrrolo[2,1-a][2]benzazepine-2(R)-carboxylic acid (2.08 g, 4.33 mmol) in methylene chloride (25 mL) and dry over anhydrous MgSO$_4$. Filter and wash with methylene chloride (3×200 mL). Evaporate in vacuo to a residue. Dissolve the residue in anhydrous dimethylformamide (25 mL) and place under nitrogen atmosphere. Add cesium carbonate (1.65 g, 5.0 mmole) in one portion. Stir for 45 minutes at ambient temperature. Add benzyl bromide (550 mg, 5.0 mmol). Stir the resulting mixture at ambient temperature for 18 hours. Quench the reaction with ethyl acetate (50 mL) and water (50 mL). Separate the organic phase and wash with water (7×50 mL), ¼ saturated potassium hydrogen carbonate (50 mL), water (50 mL), and saturated sodium chloride (50 mL). Dry (MgSO$_4$), filter and evaporate in vacuo to yield the title compound.

EXAMPLE 15

Preparation of [6α(R*), 11bβ]-6-[(S)-(1-Oxo-2(R)-thio-3-phenylpropyl)amino]- 1,2,3,5,6,7,11b-heptahydro-5-oxo-pyrrolo[2,1-a][2] benzazepine-2(R)-carboxylic acid, benzyl ester Stir [6α(R*), 11bβ]-6-[(S)-(1-oxo-2-(R)-acetylthio-3-phenylpropyl)amino]- 1,2,3,5,6,7,11b-heptahydro-5-oxo-pyrrolo[2,1-a][2]benzazepine-2(R)-carboxylic acid, benzyl ester (1.87 g, 4 mmol) and saturated methanolic ammonia at ambient temperature until hydrolysis is complete. Evaporate the solvent in vacuo and purify by silica gel chromatography to give the title compound.

EXAMPLE 16

Preparation of [6α(R*), 11bβ]-6-[(S)-(1-Oxo-2(R)-acetylthio-3-phenylpropyl)amino]-1,2,3,5,6,7,11b-heptahydro-5-oxo-pyrrolo-[2,1-a][2]benzazepine-2(S)-carboxylic acid, methyl ester Scheme A, Step f: [6α(R*), 11bβ]-6-[(S)-Amino]- 1,2,3,5,6,7,11b-heptahydro-5-oxo-pyrrolo-[2,1-a][2]benzazepine-2(S)-carboxylic acid, methyl ester Mix [6α(R*), 11bβ]-6-[(S)-(1,3-dihydro-1,3-dioxo-2H-isoindol- 2-yl)]-1,2,3,5,6,7,11b-heptahydro-5-oxo-pyrrolo [2,1-a][2]benzazepine-2(S)-carboxylic acid, methyl ester (see Example 21; Scheme A, Step e) (1.37 g, 3.38 mmol)), hydrazine monohydrate (389 mg, 7.7 mmol)) and methanol (38 mL) under nitrogen atmosphere. Heat at reflux for 5 hours. Cool to ambient temperature and filter to remove phthaloyl hydrazide. Evaporate the filtrate in vacuo to a residue and slurry in chloroform (60 mL). Remove insoluble phthaloyl hydrazide by filtration and wash with chloroform (4×21 mL). Wash the filtrate with water (4×50 mL), dry (MgSO$_4$), and filter. Evaporate the filtrate to give the title compound.

Scheme A, Step g: [6α(R*), 11bβ]-6-[(S)-(1-Oxo-2(S)-acetyloxy- 3-phenylpropyl)amino]-1,2,3,5,6,7,11b-heptahydro- 5-oxo-pyrrolo[2,1-a][2]benzazepine-2(S)-carboxylic acid, methyl ester Mix (S)-3-phenyl-2-acetyloxypropionic acid (3.6 g, 17 mmol) and [6α(R*), 11bβ]-6-[(S)-amino]-1,2,3,5,6,7,11b-heptahydro- 5-oxo-pyrrolo[2,1-a][2]benzazepine-2(S)-carboxylic acid, methyl ester (4.64 g, 17 mmol) in methylene chloride (50 mL). Add EEDQ (4.3 g, 17 mmol). Stir for 18 hours at ambient temperature under argon atmosphere. Extract with 2N hydrochloric acid, separate the organic phase, wash with water, then with saturated sodium hydrogen carbonate. Dry (MgSO$_4$), concentrate in vacuo and purify by silica gel chromatography to give the title compound.

Scheme A, Step h: [6α(R*), 11bβ]-6-[(S)-(1-Oxo-2(S)-hydroxy- 3-phenylpropyl)amino]-1,2,3,5,6,7,11b-heptahydro-5-oxo-pyrrolo[2,1-a][2]benzazepine-2(S)-carboxylic acid, methyl ester Dissolve [6α(R*), 11bβ]-6-[(S)-(1-oxo-2(S)-acetyloxy-3-phenylpropyl)amino]- 1,2,3,5,6,7,11b-heptahydro-5-oxo-pyrrolo[2,1-a][2]benzazepine-2(S)-carboxylic acid, methyl ester (7.87 g, 17.4 mmol) in ethanol (75 mL) and tetrahydrofuran (40 mL) and add lithium hydroxide (22 mL of a 1M solution, 22 mmol). Stir the reaction mixture for 2 hours. Remove the solvent in vacuo at 35° C. and partition the residue between ethyl acetate and 1N hydrochloric acid. Separate the organic phase, dry (MgSO$_4$), and concentrate in vacuo and treat with diazomethane. Purify by silica gel chromatography to give the title compound.

Scheme A, Step i: [6α(R*), 11bβ]-6-[(S)-(1-Oxo-2(R)-acetylthio- 3-phenylpropyl)amino]-1,2,3,5,6,7,11b-heptahydro- 5-oxo-pyrrolo[2,1-a][2]benzazepine-2(S)-carboxylic acid, methyl ester Mix DIAD (3.4 g, 16.3 mmol), triphenylphosphine (4.28 g, 16.3 mmol) and anhydrous tetrahydrofuran (200 mL). Cool to 0° C. and stir for 30 minutes under nitrogen atmosphere. Add a solution of [6α(R*), 11bβ]-6-[(S)-(1-oxo-2-(S)-hydroxy-3-phenylpropyl)amino]- 1,2,3,5,6,7,11b-heptahydro-5-oxo-pyrrolo[2,1-a][2]benzazepine-2(S)-carboxylic acid, methyl ester (6.7 g, 16.3 mmol) and thioacetic acid (1.75 mL, 24.5 mmol) in anhydrous tetrahydrofuran (200 mL). Stir at 0° C. for 30 minutes, then allow to warm to ambient temperature. Remove the volatiles in vacuo and purify by silica gel chromatography to give the title compound.

EXAMPLE 17

Preparation of [6α(R*), 11bβ[-6-[(S)-(1-Oxo-2(R)-thio-3-phenylpropyl)amino]-1,2,3,5,6,7,11b-heptahydro-5-oxo-pyrrolo[2,1-a][2]benzazepine-2(S)-carboxylic acid Dissolve [6α(R*), 11bβ]-6-[(S)-(1-oxo-2(R)-acetylthio-3-phenylpropyl)amino]- 1,2,3,5,6,7,11b-heptahydro-5-oxo-pyrrolo[2,1-a][2]benzazepine-2(R)-carboxylic acid, methyl ester (56 mg, 0.12 mmol) in deoxygenated methanol (3 mL) plus 1N lithium hydroxide (0.50 mL, 0.50 mmol). Stir for 30 minutes under argon atmosphere at ambient temperature. Reduce in volume to 1.5 mL in vacuo, then add, by dropwise addition, to a rapidly stirring solution of 2N hydrochloric acid (2 mL). Collect the resulting precipitate, wash with water and dry in a vacuum dessicator for 1 hour. Dry at 35° C. overnight to give the title compound.

EXAMPLE 18

Preparation of [6α(R*), 11bβ]-6-[(S)-(1-Oxo-2(R)-acetylthio-3-phenylpropyl)amino]-1,2,3,5,6,7,11b-heptahydro-5-oxo-pyrrolo[2,1-a][2]benzazepine-2(S)-carboxylic acid Mix [6α(R*), 11bβ]-6-[(S)-(1-oxo-2(R)-thio-3-phenylpropyl)amino]- 1,2,3,5,6,7,11b-heptahydro-5-oxo-pyrrolo[2,1-a][2]benzazepine-2(S)-carboxylic acid (51 mg, 0.12 mmol) and sulfuric acid (0.3 mL of a 10% solution in acetic acid). Add acetic anhydride (11 mg, 0.12 mmol) over 10 minutes. Warm to 90° C. with stirring for 45 minutes. Allow to cool, pour into diethyl ether and wash with water three times. Separate the organic phase, dry (MgSO$_4$) and concentrate in vacuo. Purify by silica gel chromatography to yield the title compound.

EXAMPLE 19

Preparation of [6α(R*), 11bβ]-6-[(S)-(1-Oxo-2(R)-acetylthio-3-phenylpropyl)amino]-1,2,3,5,6,7,11b-heptahydro-5-oxo-pyrrolo[2,1-a][2]benzazepine-2(S)-carboxylic acid, benzyl ester Dissolve [6α(R*), 11bβ]-6-[(S)-(1-oxo-2(R)-acetylthio-3-phenylpropyl)amino]- 1,2,3,5,6,7,11b-heptahydro-5-oxo-pyrrolo[2,1-a][2]benzazepine-2(S)-carboxylic acid (2.08 g, 4.33 mmol) in methylene chloride (25 mL) and dry over anhydrous MgSO$_4$. Filter and wash with methylene chloride (3×200 mL). Evaporate in vacuo to a residue. Dissolve the residue in anhydrous dimethylformamide (25 mL) and place under nitrogen atmosphere. Add cesium carbonate (1.65 g, 5.0 mmole) in one portion. Stir for 45 minutes at ambient temperature. Add benzyl bromide (550 mg, 5.0 mmol). Stir the resulting mixture at ambient temperature for 18 hours. Quench the reaction with ethyl acetate (50 mL) and water (50 mL). Separate the organic phase and wash with water (7×50 mL), ¼ saturated potassium hydrogen carbonate (50 mL), water (50 mL), and saturated sodium chloride (50 mL). Dry (MgSO$_4$), filter and evaporate in vacuo to yield the title compound.

EXAMPLE 20

Preparation of [6α(R*), 11bβ]-6-[(S)-(1-Oxo-2(R)-thio-3-phenylpropyl)amino]-1,2,3,5,6,7,11b-heptahydro-5-oxo-pyrrolo[2,1-a][2] benzazepine-2(S)-carboxylic acid, benzyl ester Stir [6α(R*), 11bβ]-6-[(S)-(1-oxo-2-(R)-acetylthio-3-phenylpropyl)amino]- 1,2,3,5,6,7,11b-heptahydro-5-oxo-pyrrolo[2,1-a][2]benzazepine-2(S)-carboxylic acid, benzyl ester (1.87 g, 4 mmol) and saturated methanolic ammonia at ambient temperature until hydrolysis is complete. Evaporate the solvent in vacuo and purify by silica gel chromatography to give the title compound.

EXAMPLE 21

Preparation of [6α(R*), 11bβ]-6-[(S)-(1-Oxo-2(S)-acetylthio-3-phenylpropyl)amino]-1,2,3,5,6,7,11b-heptahydro-5-oxo-pyrrolo[2,1-a][2]benzazepine-2(R)-carboxylic acid, methyl ester Scheme A, Step j: [6α(R*), 11bβ]-6-[(S)-(1-Oxo-2(R)-hydroxy- 3-phenylpropyl)amino]-1,2,3,5,6,7,11b-heptahydro-5-oxo-pyrrolo[2,1-a][2]benzazepine-2(R)-carboxylic acid, methyl ester Dissolve [6α(R*), 11bβ]-6-[(S)-(1-oxo-2(S)-hydroxy-3-phenylpropyl)amino]- 1,2,3,5,6,7,11b-heptahydro-5-oxo-pyrrolo[2,1-a][2]benzazepine-2(R)-carboxylic acid, methyl ester (see Example 21; Scheme A, Step h) (41 mg, 0.1 mmol), triphenylphosphine (39 mg, 0.15 mmol) and acetic acid (8.7 μL, 0.15 mmol) in anhydrous tetrahydrofuran (3 mL). Treat with DIAD (32 mg, 0.15 mmol) at 0° C. Stir for 5 minutes at 0° C., then allow to stir at ambient temperature for 45 minutes. Remove the volatiles in vacuo and purify the residue by silica gel chromatography to give [6α(R*), 11bβ]-6-[(S)-(1-oxo- 2(R)-acetyloxy-3-phenylpropyl)amino]-1,2,3,5,6,7,11b-heptahydro- 5-oxo-pyrrolo[2,1-a][2]benzazepine-2(R)-carboxylic acid, methyl ester.

Dissolve [6α(R*), 11bβ]-6-[()S-(1-oxo-2(R)-acetyloxy-3-phenylpropyl)amino]- 1,2,3,5,6,7,11b-heptahydro-5-oxo-pyrrolo[2,1-a][2]benzazepine-2(R)-carboxylic acid, methyl ester (262 mg, 0.58 mmol) in methanol (5 mL) and tetrahydrofuran (5 mL) and add lithium hydroxide (0.8 mL of a 1M solution, 0.8 mmol). Stir the reaction mixture for 2 hours and remove the solvent in vacuo. Acidify and partition between methylene chloride and water. Separate the organic phase, dry (MgSO$_4$), concentrate in vacuo and purify by silica gel chromatography to give the title compound.

Scheme A, Step k: [6α(R*), 11bβ]-6-[(S)-(1-Oxo-2(S)-acetylthio- 3-phenylpropyl)amino]-1,2,3,5,6,7,11b-heptahydro- 5-oxo-pyrrolo[2,1-a][2]benzazepine-2(R)-carboxylic acid, methyl ester Mix DIAD (31 mg, 0.15 mmol), triphenylphosphine (39 mg, 0.16 mmol) and anhydrous tetrahydrofuran (2 mL). Cool to 0° C. and stir for 30 minutes under an argon atmosphere. Add [6α(R*), 11bβ]-6-[(S)-(1-oxo-2(R)-hydroxy-3-phenylpropyl)amino]- 1,2,3,5,6,7,11b-heptahydro-5-oxo-pyrrolo[2,1-a][2]benzazepine-2(R)-carboxylic acid, methyl ester (41 mg, 0.1 mmol) as a solid, then immediately add thiolacetic acid (11 μL, 0.15 mmol). Allow the reaction to warm to ambient temperature and stir overnight. Remove the solvent in vacuo and purify the residue by silica gel chromatography to give the title compound.

EXAMPLE 22

Preparation of [6α(R*), 11bβ]-6-[(S)-(1-Oxo-2(S)-thio-3-phenylpropyl)amino]-1,2,3,5,6,7,11b-heptahydro-5-oxo-pyrrolo[2,1-a][2]benzazepine-2(R)-carboxylic acid Dissolve [6α(R*), 11bβ]-6-[(S)-(1-oxo-2(S)-acetylthio-3-phenylpropyl)amino]- 1,2,3,5,6,7,11b-heptahydro-5-oxo-pyrrolo[2,1-a][2]benzazepine-2(R)-carboxylic acid, methyl ester (56 mg, 0.12 mmol) in deoxegenated methanol (3 mL) plus 1N lithium hydroxide (0.50 mL, 0.50 mmol). Stir for 30 minutes under argon atmosphere at ambient temperature. Reduce in volume to 1.5 mL in vacuo, then add, by dropwise addition, to a rapidly stirring solution of 2N hydrochloric acid (2 mL). Collecting the resulting precipitate, wash with water and dry in a vacuum dessicator for 1 hour. Dry at 35° C. overnight to give the title compound.

EXAMPLE 23

Preparation of [6α(R*), 11bβ]-6-[(S)-(1-Oxo-2(S)-acetylthio- 3-phenylpropyl)amino]-1,2,3,5,6,7,11b-heptahydro-5-oxo-pyrrolo[2,1-a][2]benzazepine-2(R)-carboxylic acid Mix [6α(R*), 11bβ]-6-[(S)-(1-oxo-2(S)-thio-3-phenylpropyl)amino]- 1,2,3,5,6,7,11b-heptahydro-5-oxo-pyrrolo [2,1-a][2]benzazepine-2(R)-carboxylic acid (51 mg, 0.12 mmol) and sulfuric acid (0.3 mL of a 10% solution in acetic acid). Add acetic anhydride (11 mg, 0.12 mmol) over 10 minutes. Warm to 90° C. with stirring for 45 minutes. Allow to cool, pour into diethyl ether and wash with water three times. Separate the organic phase, dry (MgSO$_4$) and concentrate in vacuo. Purify by silica gel chromatography to give the title compound.

EXAMPLE 24

Preparation of [6α(R*), 11bβ]-6-[(S)-(1-Oxo-2(S)-acetylthio- 3-phenylpropyl)amino]-1,2,3,5,6,7,11b-heptahydro-5-oxo-pyrrolo[2,1-a][2]benzazepine-2(R)-carboxylic acid, benzyl ester Dissolve [6α(R*), 11bβ]-6-[(S)-(1-oxo-2(S)-acetylthio-3-phenylpropyl)amino]- 1,2,3,5,6,7,11b-heptahydro-5-oxo-pyrrolo[2,1-a][2]benzazepine-2(R)-carboxylic acid (2.08 g, 4.33 mmol) in methylene chloride (25 mL) and dry over anhydrous MgSO$_4$. Filter and wash with methylene chloride (3×200 mL). Evaporate in vacuo to a residue. Dissolve the residue in anhydrous dimethylformamide (25 mL) and place under nitrogen atmosphere. Add cesium carbonate (1.65 g, 5.0 mmole) in one portion. Stir for 45 minutes at ambient temperature. Add benzyl bromide (550 mg, 5.0 mmol). Stir the resulting mixture at ambient temperature for 18 hours. Quench the reaction with ethyl acetate (50 mL) and water (50 mL). Separate the organic phase and wash with water (7×50 mL), ¼ saturated potassium hydrogen carbonate (50 mL), water (50 mL), and saturated sodium chloride (50 mL). Dry (MgSO$_4$), filter and evaporate in vacuo to give the title compound.

EXAMPLE 25

Preparation of [6α(R*), 11bβ]-6-[(S)-(1-Oxo-2(S)-thio-3-phenylpropyl)amino]-1,2,3,5,6,7,11b-heptahydro-5-oxo-pyrrolo[2,1-a][2] benzazepine-2(R)-carboxylic acid, benzyl ester Stir [6α(R*), 11bβ]-6-[(S)-(1-oxo-2(S)-acetylthio-3-phenylpropyl)amino]- 1,2,3,5,6,7,11b-heptahydro-5-oxo-pyrrolo[2,1-a][2]benzazepine-2(R)-carboxylic acid, benzyl ester (1.87 g, 4 mmol) and saturated methanolic ammonia at ambient temperature until hydrolysis is complete. Evaporate the solvent in vacuo and purify by silica gel chromatography to give the title compound.

EXAMPLE 26

Preparation of [6α(R*), 11bβ]-6-[(S)-(1-Oxo-2(S)-acetylthio- 3-phenylpropyl)amino]-1,2,3,5,6,7,11b-heptahydro-5-oxo-pyrrolo[2,1-a][2]benzazepine-2(S)-carboxylic acid, methyl ester Scheme A, Step j: [6α(R*), 11bβ]-6-[(S)-(1-Oxo-2(R)-hydroxy- 3-phenylpropyl)amino]-1,2,3,5,6,7,11b-heptahydro-5-oxo-pyrrolo[2,1-a][2]benzazepine-2(S)-carboxylic acid, methyl ester Dissolve [6α(R*), 11bβ]-6-[(S)-(1-oxo-2(S)-hydroxy-3-phenylpropyl)amino]- 1,2,3,5,6,7,11b-heptahydro-5-oxo-pyrrolo[2,1-a][2]benzazepine-2(S)-carboxylic acid, methyl ester (see Example 26; Scheme A, Step h) (41 mg, 0.1 mmol), triphenylphosphine (39 mg, 0.15 mmol) and acetic acid (8.7 μL, 0.15 mmol) in anhydrous tetrahydrofuran (3 mL). Treat with DIAD (32 mg, 0.15 mmol) at 0° C. Stir for 5 minutes at 0° C., then allow to stir at ambient temperature for 45 minutes. Remove the volatiles in vacuo and purify the residue by silica gel chromatography to give [6α(R*), 11bβ]-6-[(S)-(1-oxo- 2(R)-acetyloxy-3-phenylpropyl)amino]-1,2,3,5,6,7,11b-heptahydro- 5-oxo-pyrrolo[2,1-a][2]benzazepine-2(S)-carboxylic acid, methyl ester.

Dissolve [6α(R*), 11bβ]-6-[()S-(1-oxo-2-(R)-acetyloxy-3-phenylpropyl)amino]- 1,2,3,5,6,7,11b-heptahydro-5-oxo-pyrrolo[2,1-a][2]benzazepine-2(S)-carboxylic acid, methyl ester (262 mg, 0.58 mmol) in methanol (5 mL) and tetrahydrofuran (5 mL) and add lithium hydroxide (0.8 mL of a 1M solution, 0.8 mmol). Stir the reaction mixture for 2 hours and remove the solvent in vacuo. Acidify and partition between methylene chloride and water. Separate the organic phase, dry (MgSO$_4$), concentrate in vacuo and purify by silica gel chromatography to give the title compound.

Scheme A, Step k: [6α(R*), 11bβ]-6-[(S)-(1-Oxo-2(S)-acetylthio- 3-phenylpropyl)amino]-1,2,3,5,6,7,11b-heptahydro- 5-oxo-pyrrolo[2,1-a][2]benzazepine-2(S)-carboxylic acid, methyl ester Mix DIAD (31 mg, 0.15 mmol), triphenylphosphine (39 mg, 0.16 mmol) and anhydrous tetrahydrofuran (2 mL). Cool to 0° C. and stir for 30 minutes under an argon atmosphere. Add [6α(R*), 11bβ]-6-[(S)-(1-oxo-2(R)-hydroxy-3-phenylpropyl)amino]- 1,2,3,5,6,7,11b-heptahydro-5-oxo-pyrrolo[2,1-a][2]benzazepine-2(S)-carboxylic acid, methyl ester (41 mg, 0.1 mmol) as a solid, then immediately add thiolacetic acid (11 μL, 0.15 mmol). Allow the reaction to warm to ambient temperature and stir overnight. Remove the solvent in vacuo and purify the residue by silica gel chromatography to give the title compound.

EXAMPLE 27

Preparation of [6α(R*), 11bβ]-6-[(S)-(1-Oxo-2(S)-thio-3-phenylpropyl)amino]-1,2,3,5,6,7,11b-heptahydro-5-oxo-pyrrolo[2,1-a][2]benzazepine-2(S)-carboxylic acid Dissolve 6α(R*), 11bβ]-6-[(S)-(1-oxo-2(S)-acetylthio-3-phenylpropyl)amino]- 1,2,3,5,6,7,11b-heptahydro-5-oxo-pyrrolo[2,1-a][2]benzazepine-2(S)-carboxylic acid, methyl ester (56 mg, 0.12 mmol) in deoxegenated methanol (3 mL) plus 1N lithium hydroxide (0.50 mL, 0.50 mmol). Stir for 30 minutes under argon atmosphere at ambient temperature. Reduce in volume to 1.5 mL in vacuo, then add, by dropwise addition, to a rapidly stirring solution of 2N hydrochloric acid (2 mL). Collect the resulting precipitate, wash with water and dry in a vacuum dessicator for 1 hour. Dry at 35° C. overnight to give the title compound.

EXAMPLE 28

Preparation of [6α(R*), 11bβ]-6-[(S)-(1-Oxo-2(S)-acetylthio-3-phenylpropyl)amino]-1,2,3,5,6,7,11b-heptahydro-5-oxo-pyrrolo[2,1-a][2]benzazepine-2(S)-carboxylic acid Mix [6α(R*), 11bβ]-6-[(S)-(1-oxo-2(S)-thio-3-phenylpropyl)amino]- 1,2,3,5,6,7,11b-heptahydro-5-oxo-pyrrolo[2,1-a][2]benzazepine-2(S)-carboxylic acid (51 mg, 0.12 mmol) and sulfuric acid (0.3 mL of a 10% solution in acetic acid). Add acetic anhydride (11 mg, 0.12 mmol) over 10 minutes. Warm to 90° C. with stirring for 45 minutes. Allow to cool, pour into diethyl ether and wash with water three times. Separate the organic phase, dry (MgSO$_4$) and concentrate in vacuo. Purify by silica gel chromatography to give the title compound.

EXAMPLE 29

Preparation of [6α(R*), 11bβ]-6-[(S)-(1-Oxo-2(S)-acetylthio-3-phenylpropyl)amino]-1,2,3,5,6,7,11b-heptahydro-5-oxo-pyrrolo-[2,1-a][2]benzazepine-2(S)-carboxylic acid, benzyl ester Dissolve [6α(R*), 11bβ]-6-[(S)-(1-oxo-2(S)-acetylthio-3-phenylpropyl)amino]- 1,2,3,5,6,7,11b-heptahydro-5-oxo-pyrrolo[2,1-a][2]benzazepine-2(S)-carboxylic acid (2.08 g, 4.33 mmol) in methylene chloride (25 mL) and dry over anhydrous MgSO$_4$. Filter and wash with methylene chloride (3×200 mL). Evaporate in vacuo to a residue. Dissolve the residue in anhydrous dimethylformamide (25 mL) and place under nitrogen atmosphere. Add cesium carbonate (1.65 g, 5.0 mmole) in one portion. Stir for 45 minutes at ambient temperature. Add benzyl bromide (550 mg, 5.0 mmol). Stir the resulting mixture at ambient temperature for 18 hours. Quench the reaction with ethyl acetate (50 mL) and water (50 mL). Separate the organic phase and wash with water (7×50 mL), ¼ saturated potassium hydrogen carbonate (50 mL), water (50 mL), and saturated sodium chloride (50 mL). Dry (MgSO$_4$), filter and evaporate in vacuo to give the title compound.

EXAMPLE 30

Preparation of [6α(R*), 11bβ]-6-[(S)-(1-Oxo-2(S)-thio-3-phenylpropyl)amino]-1,2,3,5,6,7,11b-heptahydro-5-oxo-pyrrolo[2,1-a][2]benzazepine-2(S)-carboxylic acid, benzyl ester Stir [6α(R*), 11bβ]-6-[(S)-(1-oxo-2(S)-acetylthio-3-phenylpropyl)amino]- 1,2,3,5,6,7,11b-heptahydro-5-oxo-pyrrolo[2,1-a][2]benzazepine-2(S)-carboxylic acid, benzyl ester (1.87 g, 4 mmol) and saturated methanolic ammonia at ambient temperature until hydrolysis is complete. Evaporate the solvent in vacuo and purify by silica gel chromatography to give the title compound.

EXAMPLE 31

Preparation of [7α(R*), 12bβ]-7-[(S)-(1-Oxo-2(R)-acetylthio-3-phenylpropyl)amino]-1,2,3,4,6,7,8,12b-octahydro-6-oxo-pyrido[2,1-a][2]benzazepine-3(R)-carboxylic acid, methyl ester Step d$_2$: (S)-N-[2-(1,3-Dihydro-1,3-dioxo-2H-isoindol-2-yl)- 1-oxo-3-phenylpropyl]-2-(3-oxopropyl)-β-alanine, methyl esters Mix (S)-N-[2-(1,3-dihydro-1,3-dioxo-2H-isoindol-3-yl)-1-oxo- 3-phenylpropyl]-2-(2-propenyl)-β-alanine, methyl ester (4.2 g, 10 mmol) in anhydrous tetrahydrofuran (5 mL) under nitrogen atmosphere. Add, by dropwise addition, a solution of 9-BBN (20 mL of a 0.5M solution in tetrahydrofuran, 10 mmol). Stir until hydroboration is complete. Add 30% hydrogen peroxide (0.2 mL) and 10N sodium hydroxide (2.0 mL), then isolate the alcohol.

Mix oxalyl chloride (2 mL, 20 mmole) and methylene chloride (40 mL) and place under nitrogen atmosphere. Cool below −50° C. and add a solution of methyl sulfoxide (1.6 g, 20 mmol) in methylene chloride (1.5 mL). Stir for 15 minutes and add a solution of the above alcohol (10 mmol) in methylene chloride, keeping the pot temperature below −50° C. for 30 minutes. Add triethylamine (8 mL, 60 mmol) over 30 minutes. Stir while warming to 0° C., quench with water, extract with ethyl acetate and dry (MgSO$_4$). Purify by silica gel chromatography to give the diatereomeric title compounds.

Scheme A, Step d: (S)-N-[2-(1,3-Dihydro-1,3-dioxo-2H-isoindol- 2-yl)]-1-oxo-3-phenylpropyl-1,2,3,4-tetrahydro-3-pyridinecarboxylic acid, methyl esters Mix (S)-N-[2-(1,3-dihydro-1,3-dioxo-2H-isoindol-2-yl)]-(S)- 1-oxo-3-phenylpropyl]-2-(3-oxopropyl)-β-alanine, methyl esters (4.5 g), methylene chloride (150 mL) and trifluoroacetic acid (0.5 mL). Reflux for 8 hours and purify by silica gel chromatography (50% ethyl acetate/hexane) to yield 3.5 g (87%) diastereomeric title compounds.

Scheme A, Step e: [7α(R*), 12bβ]-7-[(S)-(1,3-Dihydro-1,3-dioxo- 2H-isoindol-2-yl)]-1,2,3,4,6,7,8,12b-octahydro-6-oxo-pyrido[2,1-a][2]benzazepine-3(R)-carboxylic acid, methyl ester and [7α(R*), 12bβ]-7-[(S)-(1,3-Dihydro-1,3-dioxo-2H-isoindol- 2-yl)]-1,2,3,4,6,7,8,12b-octahydro-6-oxo-pyrido[2,1-a][2]benzazepine-3(S)-carboxylic acid, methyl ester Place trifluoromethane sulfonic acid (10 mL) in a flask under nitrogen atmosphere at 25° C. Add (S)-N-[2-(1,3-dihydro-1,3-dioxo- 2H-isoindol-2-yl)]-1-oxo-3-phenylpropyl-1,2,3,4-tetrahydro- 3-pyridinecarboxylic acid, methyl ester (2.5 g, 6 mmol) in methylene chloride (10 mL). Stir the mixture for 6 hours until the reaction is complete. Pour into water and extract with ethyl acetate. Wash well with water, dry (MgSO$_4$) and concentrate to yield the diastereomeric title compounds. Separate by HPLC.

Scheme A, Step f: [7α(R*), 12bβ]-7-[(S)-Amino]- 1,2,3, 4,6,7,8,12b-octahydro-6-oxo-pyrido[2,1-a][2]benzazepine-3(R)-carboxylic acid, methyl ester Mix [7α(R*), 12bβ]-7-[(S)-(1,3-dihydro-1,3-dioxo-2H-isoindol- 2-yl)]-1,2,3,4,6,7,8,12b-octahydro-6-oxo-pyrido[2,1-a][2]benzazepine-3(R)-carboxylic acid, methyl ester (1.37 g, 3.38 mmol)), hydrazine monohydrate (389 mg, 7.7 mmol)) and methanol (38 mL) under nitrogen atmosphere. Heat at reflux for 5 hours. Cool to ambient temperature and filter to remove phthaloyl hydrazide. Evaporate the filtrate in vacuo to a residue and slurry in chloroform (60 mL). Remove insoluble phthaloyl hydrazide by filtration and wash with chloroform (4×20 mL). Wash the filtrate with water (4×50 mL), dry (MgSO$_4$), and filter. Evaporate the filtrate to yield the title compound.

Scheme A, Step g: [7α(R*), 12bβ]-7-[(S)-(1-Oxo-2(S)-acetyloxy- 3-phenylpropyl)amino]-1,2,3,4,6,7,8,12b-octahydro- 6-oxo-pyrido[2,1-a][2]benzazepine-3(R)-carboxylic acid, methyl ester Mix (S)-3-phenyl-2-acetyloxypropionic acid (3.6 g, 17 mmol) and [7α(R*), 12bβ]-7-[(S)-amino]-1,2,3,4,6,7,8,12b-octahydro- 6-oxo-pyrido[2,1-a][2]benzazepine-3(R)-carboxylic acid, methyl ester (4.64 g, 17 mmol) in methylene chloride (50 mL). Add EEDQ (4.3 g, 17 mmol). Stir for 18 hours at ambient temperature under argon atmosphere. Extract with 2N hydrochloric acid, separate the organic phase, wash with water, then with saturated sodium hydrogen carbonate. Dry (MgSO$_4$), concentrate in vacuo and purify by silica gel chromatography to give the title compound.

Scheme A, Step h: [7α(R*), 12bβ]-7-[(S)-(1-Oxo-2(S)-hydroxy- 3-phenylpropyl)amino]-1,2,3,4,6,7,8,12b-octahydro-6-oxo-pyrido[2,1-a][2]benzazepine-3(R)-carboxylic acid, methyl ester Dissolve [7α(R*), 12bβ]-7-[(S)-(1-oxo-2(S)-acetyloxy-3-phenylpropyl)amino]- 1,2,3,4,6,7,8,12b-octahydro-6-oxo-pyrido[2,1-a][2]benzazepine-3(R)-carboxylic acid, methyl ester (7.87 g, 17.4 mmol) in ethanol (75 mL) and tetrahydrofuran (40 mL) and add lithium hydroxide (22 mL of a 1M solution, 22 mmol). Stir the reaction mixture for 2 hours. Remove the solvent in vacuo at 35° C. and partition the residue between ethyl acetate and 1N hydrochloric acid. Separate the organic phase, dry (MgSO$_4$), and concentrate in vacuo. Purify by silica gel chromatography to give the title compound.

Scheme A, Step i: [7α(R*), 12bβ]-7-[(S)-(1-Oxo-2(R)-acetylthio- 3-phenylpropyl)amino]-1,2,3,4,6,7,8,12b-octahydro- 6-oxo-pyrido[2,1-a][2]benzazepine-3(R)-carboxylic acid, methyl ester Mix DIAD (3.4 g, 16.3 mmol), triphenylphosphine (4.28 g, 16.3 mmol) and anhydrous tetrahydrofuran (200 mL). Cool to 0° C. and stir for 30 minutes under nitrogen atmosphere. Add a solution of [7α(R*), 12bβ]-7-[(S)-(1-oxo-2(S)-hydroxy-3-phenylpropyl)amino]- 1,2,3,4,6,7,8, 12b-octahydro-6-oxo-pyrido[2,1-a][2]benzazepine-3(R)-carboxylic acid, methyl ester (6.7 g, 16.3 mmol) and thiolacetic acid (1.75 mL, 24.5 mmol) in anhydrous tetrahydrofuran (200 mL). Stir at 0° C. for 30 minutes, then allow to warm to ambient temperature. Remove the volatiles in vacuo and purify by silica gel chromatography to give the title compound.

EXAMPLE 32

Preparation of [7α(R*), 12bβ]-7-[(S)-(1-Oxo-2(R)-thio-3-phenylpropyl)amino]-1,2,3,4,6,7,8,12b-octahydro-6-oxo-pyrido[2,1-a][2] benzazepine-3(R)-carboxylic acid Dissolve [7α(R*), 12bβ]-7-[(S)-(1-oxo-2(R)-acetylthio-3-phenylpropyl)amino]- 1,2,3,4,6,7,8,12b-octahydro-6-oxo-pyrido[2,1-a][2]benzazepine-3(R)-carboxylic acid, methyl ester (56 mg, 0.12 mmol) in deoxegenated methanol (3 mL) plus 1N lithium hydroxide (0.50 mL, 0.50 mmol). Stir for 30 minutes under argon atmosphere at ambient temperature. Reduce in volume to 1.5 mL in vacuo, then add, by dropwise addition, to a rapidly stirring solution of 2N hydrochloric acid (2 mL). Collect the resulting precipitate, wash with water and dry in a vacuum dessicator for 1 hour. Dry at 35° C. overnight to give the title compound.

EXAMPLE 33

Preparation of [7α(R*), 12bβ]-[(S)-(1-Oxo-2(R)-acetylthio-3-phenylpropyl)amino]-1,2,3,4,6,7,8,12b-octahydro-6-oxo-pyrido[2,1-a][2]benzazepine-3(R)-carboxylic acid Mix [7α(R*), 12bβ]-7-[(S)-(1-oxo-2(R)-thio-3-phenylpropyl)amino]- 1,2,3,4,6,7,8,12b-octahydro-6-oxo-pyrido[2,1,-a][2]benzazepine-3(R)-carboxylic acid (51 mg, 0.12 mmol) and sulfuric acid (0.3 mL of a 10% solution in acetic acid). Add acetic anhydride (11 mg, 0.12 mmol) over 10 minutes. Warm to 90° C. with stirring for 45 minutes. Allow to cool, pour into diethyl ether and wash with water three times. Separate the organic phase, dry (MgSO$_4$) and concentrate in vacuo. Purify by silica gel chromatography to give the title compound.

EXAMPLE 34

Preparation of [7α(R*), 12bβ]-7-[(S)-(1-Oxo-2(R)-acetylthio-3-phenylpropyl)amino]-1,2,3,4,6,7,8,12b-octahydro-6-oxo-pyrido[2,1-a][2]benzazepine-3(R)-carboxylic acid, benzyl ester Dissolve [7α(R*), 12bβ]-7-[(S)-(1-oxo-2(R)-acetylthio-3-phenylpropyl)amino]- 1,2,3,4,6,7,8,12b-octahydro-6-oxopyrido[2,1-a][2]benzazepine-3(R)-carboxylic acid (2.08 g, 4.33 mmol) in methylene chloride (25 mL) and dry over anhydrous MgSO$_4$. Filter and wash with methylene chloride (3×200 mL). Evaporate in vacuo to a residue. Dissolve the residue in anhydrous dimethylformamide (25 mL) and place under nitrogen atmosphere. Add cesium carbonate (1.65 g, 5.0 mmole) in one portion. Stir for 45 minutes at ambient temperature. Ad benzyl bromide (550 mg, 5.0 mmol). Stir the resulting mixture at ambient temperature for 18 hours. Quench the reaction with ethyl acetate (50 mL) and water (50 mL). Separate the organic phase and wash with water (7×50 mL), ¼ saturated potassium hydrogen carbonate (50 mL), water (50 mL), and saturated sodium chloride (50 mL). Dry (MgSO$_4$), filter and evaporate in vacuo to yield the title compound.

EXAMPLE 35

Preparation of [7α(R*), 12bβ]-7-[(S)-(1-Oxo-2(R)-thio-3-phenylpropyl)amino]-1,2,3,4,6,7,8,12b-octahydro-6-oxo-pyrido[2,1-a][2]benzazepine-3(R)-carboxylic acid, benzyl ester Stir [7α(R*), 12bβ]-7-[(S)-(1-oxo-2(R)-acetylthio-3-phenylpropyl)amino]- 1,2,3,4,6,7,8,12b-octahydro-6-oxo-pyrido[2,1-a][2]benzazepine-3(R)-carboxylic acid, benzyl ester (1.87 g, 4 mmol) and saturated methanolic ammonia at ambient temperature until hydrolysis is complete. Evaporate the solvent in vacuo and purify by silica gel chromatography to give the title compound.

EXAMPLE 36

Preparation of [7α(R*), 12bβ]-7-[(S)-(1-Oxo-2(R)-acetylthio-3-phenylpropyl)amino]-1,2,3,4,6,7,8,12b-octahydro-6-oxo-pyrido[2,1-a][2]benzazepine-3(S)-carboxylic acid, methyl ester Scheme A, Step f: [7α(R*), 12bβ]-7-[(S)-Amino]- 1,2,3,4,6,7,8,12b-octahydro-6-oxo-pyrido[2,1-a][2]benzazepine-3(S)-carboxylic acid, methyl ester Mix [7α(R*), 12bβ]-7-[(S)-(1,3-dihydro-1,3-dioxo-2H-isoindol- 2-yl)]-1,2,3,4,6,7,8,12b-octahydro-6-oxo-pyrido[2,1-a][2]benzazepine-3(S)-carboxylic acid, methyl ester (see Example 41; Scheme A, Step e) (1.37 g, 3.38 mmol)), hydrazine monohydrate (389 mg, 7.7 mmol)) and methanol (38 mL) under nitrogen atmosphere. Heat at reflux for 5 hours. Cool to ambient temperature and filter to remove phthaloyl hydrazide. Evaporate the filtrate in vacuo to a residue and slurry in chloroform (60 mL). Remove insoluble phthaloyl hydrazide by filtration and wash with chloroform (4×20 mL). Wash the filtrate with water (4×50 mL), dry (MgSO$_4$), and filter. Evaporate the filtrate to yield the title compound.

Scheme A, Step q: [7α(R*), 12bβ]-7-[(S)-(1-Oxo-2(S)-acetyloxy- 3(S)-phenylpropyl)amino]-1,2,3,4,6,7,8,12b-octahydro- 6-oxo-pyrido[2,1-a][2]benzazepine-3(S)-carboxylic acid, methyl ester Mix (S)-3-phenyl-2-acetyloxypropionic acid (3.6 g, 17 mmol) and [7α(R*), 12bβ]-7-[(S)-amino]-1,2,3,4,6,7,8,12b-octahydro- 6-oxo-pyrido[2,1-a][2]benzazepine-3(S)-carboxylic acid, methyl ester (4.64 g, 17 mmol) in methylene chloride (50 mL). Add EEDQ (4.3 g, 17 mmol). Stir for 18 hours at ambient temperature under argon atmosphere. Extract with 2N hydrochloric acid, separate the organic phase, wash with water, then with saturated sodium hydrogen carbonate. Dry (MgSO$_4$), concentrate in vacuo and purify by silica gel chromatography to give the title compound.

Scheme A, Step h: [7α(R*), 12bβ]-7-[(S)-(1-Oxo-2(S)-hydroxy- 3-phenylpropyl)amino]-1,2,3,4,6,7,8,12b-octahydro-6-oxo-pyrido[2,1-a][2]benzazepine-3(S)-carboxylic acid, methyl ester Dissolve [7α(R*), 12bβ]-7-[(S)-(1-oxo-2(S)-acetyloxy-3-phenylpropyl)amino]- 1,2,3,4,6,7,8,12b-octahydro-6-oxo-pyrido[2,1-a][2]benzazepine-3(S)-carboxylic acid, methyl ester (7.87 g, 17.4 mmol) in ethanol (75 mL) and tetrahydrofuran (40 mL) and add lithium hydroxide (22 mL of a 1M solution, 22 mmol). Stir the reaction mixture for 2 hours. Remove the solvent in vacuo at 35° C. and partition the residue between ethyl acetate and 1N hydrochloric acid. Separate the organic phase, dry (MgSO$_4$), and concentrate in vacuo. Purify by silica gel chromatography to give the title compound.

Scheme A, Step i: [7α(R*), 12bβ]-7-[(S)-(1-Oxo-2(R)-acetylthio- 3-phenylpropyl)amino]-1,2,3,4,6,7,8,12b-octahydro- 6-oxo-pyrido[2,1-a][2]benzazepine-3(S)-carboxylic acid, methyl ester Mix DIAD (3.4 g, 16.3 mmol), triphenylphosphine (4.28 g, 16.3 mmol) and anhydrous tetrahydrofuran (200 mL). Cool to 0° C. and stir for 30 minutes under nitrogen atmosphere. Add a solution of [7α(R*), 12bβ]-7-[(S)-(1-oxo-2(S)-hydroxy-3-phenylpropyl)amino]- 1,2,3,4,6,7,8,12b-octahydro-6-oxo-pyrido[2,1-a][2]benzazepine-3(S)-carboxylic acid, methyl ester (6.7 g, 16.3 mmol) and thiolacetic acid (1.75 mL, 24.5 mmol) in anhydrous tetrahydrofuran (200 mL). Stir at 0° C. for 30 minutes, then allow to warm to ambient temperature. Remove the volatiles in vacuo and purify by silica gel chromatography to give the title compound.

EXAMPLE 37

Preparation of [7α(R*), 12bβ]-7-[(S)-(1-Oxo-2(R)-thio-3-phenylpropyl)amino]-1,2,3,4,6,7,8,12b-octahydro-6-oxo-pyrido[2,1-a][2]benzazepine-3(S)-carboxylic acid Dissolve [7α(R*), 12bβ]-7-[(S)-(1-oxo-2(R)-acetylthio-3-phenylpropyl)amino]- 1,2,3,4,6,7,8,12b-octahydro-6-oxo-pyrido[2,1-a][2]benzazepine-3(S)-carboxylic acid, methyl ester (56 mg, 0.12 mmol) in deoxegenated methanol (3 mL) plus 1N lithium hydroxide (0.50 mL, 0.50 mmol). Stir for 30 minutes under argon atmosphere at ambient temperature. Reduce in volume to 1.5 mL in vacuo, then add, by dropwise addition, to a rapidly stirring solution of 2N hydrochloric acid (2 mL). Collect the resulting precipitate, wash with water and dry in a vacuum dessicator for 1 hour. Dry at 35° C. overnight to give the title compound.

EXAMPLE 38

Preparation of [7α(R*), 12bβ]-7-[(S)-(1-Oxo-2(R)-acetylthio- 3-phenylpropyl)amino]-1,2,3,4,6,7,8,12b-octahydro-6-oxo-pyrido[2,1-a][2]benzazepine-3(S)-carboxylic acid Mix [7α(R*), 12bβ]-7-[(S)-(1-oxo-2(R)-thio-3-phenylpropyl)amino]- 1,2,3,4,6,7,8,12b-octahydro-6-oxo-pyrido[2,1-a][2]benzazepine-3(S)-carboxylic acid (51 mg, 0.12 mmol) and sulfuric acid (0.3 mL of a 10% solution in acetic acid). Add acetic anhydride (11 mg, 0.12 mmol) over 10 minutes. Warm to 90° C. with stirring for 45 minutes. Allow to cool, pour into diethyl ether and wash with water three times. Separate the organic phase, dry (MgSO$_4$) and concentrate in vacuo. Purify by silica gel chromatography to give the title compound.

EXAMPLE 39

Preparation of [7α(R*), 12bβ]-7-[(S)-(1-Oxo-2(R)-acetylthio-3-phenylpropyl)amino]-1,2,3,4,6,7,8,12b-octahydro-6-oxo-pyrido[2,1-a][2]benzazepine-3(S)-carboxylic acid, benzyl ester Dissolve [7α(R*), 12bβ]-7-[(S)-(1-oxo-2(R)-acetylthio-3-phenylpropyl)amino]- 1,2,3,4,6,7,8,12b-octahydro-6-oxo-pyrido[2,1-a][2]benzazepine-3(S)-carboxylic acid (2.08 g, 4.33 mmol) in methylene chloride (25 mL) and dry over anhydrous MgSO$_4$. Filter and wash with methylene chloride (3×200 mL). Evaporate in vacuo to a residue. Dissolve the residue in anhydrous dimethylformamide (25 mL) and place under nitrogen atmosphere. Add cesium carbonate (1.65 g, 5.0 mmole) in one portion. Stir for 45 minutes at ambient temperature. Add benzyl bromide (550 mg, 5.0 mmol). Stir the resulting mixture at ambient temperature for 18 hours. Quench the reaction with ethyl acetate (50 mL) and water (50 mL). Separate the organic phase and wash with water (7×50 mL), ¼ saturated potassium hydrogen carbonate (50 mL), water (50 mL), and saturated sodium chloride (50 mL). Dry (MgSO$_4$), filter and evaporate in vacuo to yield the title compound.

EXAMPLE 40

Preparation of [7α(R*), 12bβ]-7-[(S)-(1-Oxo-2(R)-thio-3-phenylpropyl)amino]-1,2,3,4,6,7,8,12b-octahydro-6-oxo-pyrido[2,1-a][2] benzazepine-3(S)-carboxylic acid, benzyl ester Stir [7α(R*), 12bβ]-7-[(S)-(1-oxo-2(R)-acetylthio-3-phenylpropyl)amino]- 1,2,3,4,6,7,8,12b-octahydro-6-oxo-pyrido-[2,1-a][2]benzazepine-3(S)-carboxylic acid, benzyl ester (1.87 g, 4 mmol) and saturated methanolic ammonia at ambient temperature until hydrolysis is complete. Evaporate the solvent in vacuo and purify by silica gel chromatography to give the title compound.

EXAMPLE 41

Preparation of [7α(R*), 12bβ]-7-[(S)-(1-Oxo-2(S)-acetylthio-3-phenylpropyl)amino]-1,2,3,4,6,7,8,12b-octahydro-6-oxo-pyrido[2,1-a][2]benzazepine-3(R)-carboxylic acid, methyl ester Scheme A, Step j: [7α(R*), 12bβ]-7-[(S)-(1-Oxo-2(R)-hydroxy- 3-phenylpropyl)amino]-1,2,3,4,6,7,8,12b-octahydro-6-oxo-pyrido[2,1-a][2]benzazepine-3(R)-carboxylic acid, methyl ester Dissolve [7α(R*), 12bβ]-7-[(S)-(1-oxo-2(S)-hydroxy-3-phenylpropyl)amino]- 1,2,3,4,6,7,8,12b-octahydro-6-oxo-pyrido[2,1-a][2]benzazepine-3(R)-carboxylic acid, methyl ester (see Example 41; Scheme A, Step h) (41 g, 0.1 mmol), triphenylphosphine (39 mg, 0.15 mmol) and acetic acid (8.7 μL, 0.15 mmol) in anhydrous tetrahydrofuran (3 mL). Treat with DIAD (32 mg, 0.15 mmol) at 0° C. Stir for 5 minutes at 0° C., then allow to stir at ambient temperature for 45 minutes. Remove the volatiles in vacuo and purify the residue by silica gel chromatography to give [7α(R*), 12bβ]-7-[(S)-(1-oxo- 2(R)-acetyloxy-3-phenylpropyl)amino]-1,2,3,4,6,7,8,12b-octahydro- 6-oxo-pyrido[2,1-a][2]benzazepine-3(R)-carboxylic acid, methyl ester.

Dissolve [7α(R*), 12bβ]-7-[(S)-(1-oxo-2(R)-acetyloxy-3-phenylpropyl)amino-]- 1,2,3,4,6,7,8,12b-octahydro-6-oxo-pyrido[2,1-a][2]benzazepine-3(R)-carboxylic acid, methyl ester (262 mg, 0.58 mmol) in methanol (5 mL) and tetrahydrofuran (5 mL) and add lithium hydroxide (0.8 mL of a 1M solution, 0.8 mmol). Stir the reaction mixture for 2 hours and remove the solvent in vacuo. Acidify and partition between methylene chloride and water. Separate the organic phase, dry (MgSO$_4$), concentrate in vacuo and purify by silica gel chromatography to give the title compound.

Scheme A, Step k: [7α(R*), 12bβ]-7-[(S)-(1-Oxo-2(S)-acetylthio- 3-phenylpropyl)amino]-1,2,3,4,6,7,8,12b-octahydro- 6-oxo-pyrido[2,1-a][2]benzazepine-3(R)-carboxylic acid, methyl ester Mix DIAD (31 mg, 0.15 mmol), triphenylphosphine (39 mg, 0.16 mmol) and anhydrous tetrahydrofuran (2 mL). Cool to 0° C. and stir for 30 minutes under an argon atmosphere. Add [7α(R*), 12bβ]-7-[(S)-(1-oxo-2(R)-hydroxy-3-phenylpropyl)amino]- 1,2,3,4,6,7,8,12b-octahydro-6-oxo-pyrido[2,1-a][2]benzazepine-3(R)-carboxylic acid, methyl ester (41 mg, 0.1 mmol) as a solid, then immediately add thiolacetic acid (11 μL, 0.15 mmol). Allow the reaction to warm to ambient temperature and stir overnight. Remove the solvent in vacuo and purify the residue by silica gel chromatography to give the title compound.

EXAMPLE 42

Preparation of [7α(R*), 12bβ]-7-[(S)-(1-Oxo-2(S)-thio-3-phenylpropyl)amino]-1,2,3,4,6,7,8,12b-octahydro-6-oxo-pyrido[2,1-a][2] benzazepine-3(R)-carboxylic acid Dissolve [7α(R*), 12bβ]-7-[(S)-(1-oxo-2(S)-acetylthio-3-phenylpropyl)amino]- 1,2,3,4,6,7,8,12b-octahydro-6-oxo-pyrido[2,1-a][2]benzazepine-3(R)-carboxylic acid, methyl ester (56 mg, 0.12 mmol) in deoxegenated methanol (3 mL) plus 1N lithium hydroxide (0.50 mL, 0.50 mmol). Stir for 30 minutes under argon atmosphere at ambient temperature. Reduce in volume to 1.5 mL in vacuo, then add, by dropwise addition, to a rapidly stirring solution of 2N hydrochloric acid (2 mL). Collect the resulting precipitate, wash with water and dry in a vacuum dessicator for 1 hour. Dry at 35° C. overnight to give the title compound.

EXAMPLE 43

Preparation of [7α(R*), 12bβ]-7-[(S)-(1-Oxo-2-(S)-acetylthio-3-phenylpropyl)amino]-1,2,3,4,6,7,8,12b-octahydro-6-oxo-pyrido[2,1-a][2]benzazepine-3(R)-carboxylic acid Mix [7α(R*), 12bβ]-7-[(S)-(1-oxo-2(S)-thio-3-phenylpropyl)amino]- 1,2,3,4,6,7,8,12b-octahydro-6-oxo-pyrido[2,1-a][2]benzazepine-3(R)-carboxylic acid (51 mg, 0.12 mmol) and sulfuric acid (0.3 mL of a 10% solution in acetic acid). Add acetic anhydride (11 mg, 0.12 mmol) over 10 minutes. Warm to 90° C. with stirring for 45 minutes. Allow to cool, pour into diethyl ether and wash with water three times. Separate the organic phase, dry (MgSO$_4$) and concentrate in vacuo. Purify by silica gel chromatography to give the title compound.

EXAMPLE 44

Preparation of [7α(R*), 12bβ]-7-[(S)-(1-Oxo-2(S)-acetylthio-3-phenylpropyl)amino]-1,2,3,4,6,7,8,12b-octahydro-6-oxo-pyrido[2,1-a][2]benzazepine-3(R)-carboxylic acid, benzyl ester Dissolve [7α(R*), 12bβ]-7-[(S)-(1-oxo-2(S)-acetylthio-3-phenylpropyl)amino]- 1,2,3,4,6,7,8,12b-octahydro-6-oxo-pyrido[2,1-a][2]benzazepine-3(R)-carboxylic acid (2.08 g, 4.33 mmol) in methylene chloride (25 mL) and dry over anhydrous MgSO₄. Filter and wash with methylene chloride (3×200 mL). Evaporate in vacuo to a residue. Dissolve the residue in anhydrous dimethylformamide (25 mL) and place under nitrogen atmosphere. Add cesium carbonate (1.65 g, 5.0 mmole) in one portion. Stir for 45 minutes at ambient temperature. Add benzyl bromide (550 mg, 5.0 mmol). Stir the resulting mixture at ambient temperature for 18 hours. Quench the reaction with ethyl acetate (50 mL) and water (50 mL). Separate the organic phase and wash with water (7×50 mL), ¼ saturated potassium hydrogen carbonate (50 mL), water (50 mL), and saturated sodium chloride (50 mL). Dry (MgSO₄), filter and evaporate in vacuo to give the title compound.

EXAMPLE 45

Preparation of [7α(R*), 12bβ]-7-[(S)-(1-Oxo-2(S)-thio-3-phenylpropyl)amino]-1,2,3,4,6,7,8,12b-octahydro-6-oxo-pyrido[2,1-a][2]benzazepine-3(R)-carboxylic acid, benzyl ester Stir [7α(R*), 12bβ]-7-[(S)-(1-oxo-2(S)-acetylthio-3-phenylpropyl)amino]- 1,2,3,4,6,7,8,12b-octahydro-6-oxo-pyrido[2,1-a][2]benzazepine-3(R)-carboxylic acid, benzyl ester (1.87 g, 4 mmol) and saturated methanolic ammonia at ambient temperature until hydrolysis is complete. Evaporate the solvent in vacuo and purify by silica gel chromatography to give the title compound.

EXAMPLE 46

Preparation of [7α(R*), 12bβ]-7-[(S)-(1-Oxo-2(S)-acetylthio-3-phenylpropyl)amino]-1,2,3,4,6,7,8,12b-octahydro-6-oxo-pyrido[2,1-a][2]benzazepine-3(S)-carboxylic acid, methyl ester Scheme A, Step j: [7α(R*), 12bβ]-7-[(S)-(1-Oxo-2(R)-hydroxy- 3-phenylpropyl)amino]-1,2,3,4,6,7,8,12b-octahydro-6-oxo-pyrido[2,1-a][2]benzazepine-3(S)-carboxylic acid, methyl ester Dissolve [7α(R*), 12bβ]-7-[(S)-(1-oxo-2(S)-hydroxy-3-phenylpropyl)amino]- 1,2,3,4,6,7,8,12b-octahydro-6-oxo-pyrido[2,1-a][2]benzazepine-3(S)-carboxylic acid, methyl ester (see Example 46; Scheme A, Step h) (41 mg, 0.1 mmol), triphenylphosphine (39 mg, 0.15 mmol) and acetic acid (8.7 μL, 0.15 mmol) in anhydrous tetrahydrofuran (3 mL). Treat with DIAD (32 mg, 0.15 mmol) at 0° C. Stir for 5 minutes at 0° C., then allow to stir at ambient temperature for 45 minutes. Remove the volatiles in vacuo and purify the residue by silica gel chromatography to give [7α(R*), 12bβ]-7-[(S)-(1-oxo- 2(R)-acetyloxy-3-phenylpropyl)amino]-1,2,3,4,6,7,8,12b-octahydro- 6-oxo-pyrido[2,1-a][2]benzazepine-3(S)-carboxylic acid, methyl ester Dissolve [7α(R*), 12bβ]-7-[(S)-(1-oxo-2(R)-acetyloxy-3-phenylpropyl)amino]- 1,2,3,4,6,7,8,12b-octahydro-6-oxo-pyrido[2,1-a][2]benzazepine-3(S)-carboxylic acid, methyl ester (262 mg, 0.58 mmol) in methanol (5 mL) and tetrahydrofuran (5 mL) and add lithium hydroxide (0.8 mL of a 1M solution, 0.8 mmol). Stir the reaction mixture for 2 hours and remove the solvent in vacuo. Acidify and partition between methylene chloride and water. Separate the organic phase, dry (MgSO₄), concentrate in vacuo and purify by silica gel chromatography to give the title compound.

Scheme A, Step k: [7α(R*), 12bβ]-7-[(S)-(1-Oxo-2(S)-acetylthio- 3-phenylpropyl)amino]-1,2,3,4,6,7,8,12b-octahydro- 6-oxo-pyrido[2,1-a][2]benzazepine-3(S)-carboxylic acid, methyl ester Mix DIAD (31 mg, 0.15 mmol), triphenylphosphine (39 mg, 0.16 mmol) and anhydrous tetrahydrofuran (2 mL). Cool to 0° C. and stir for 30 minutes under an argon atmosphere. Add [7α(R*), 12bβ]-7-[(S)-(1-oxo-2(R)-hydroxy-3-phenylpropyl)amino]- 1,2,3,4,6,7,8,12b-octahydro-6-oxo-pyrido[2,1-a][2]benzazepine-3(S)-carboxylic acid, methyl ester (41 mg, 0.1 mmol) as a solid, then immediately add thiolacetic acid (11 μL, 0.15 mmol). Allow the reaction to warm to ambient temperature and stir overnight. Remove the solvent in vacuo and purify the residue by silica gel chromatography to give the title compound.

EXAMPLE 47

Preparation of [7α(R*), 12bβ]-7-[(S)-(1-Oxo-2(S)-thio-3-phenylpropyl)amino]-1,2,3,4,6,7,8,12b-octahydro-6-oxo-pyrido[2,1-a][2]benzazepine-3(S)-carboxylic acid Dissolve [7α(R*), 12bβ]-7-[(S)-(1-oxo-2(S)-acetylthio-3-phenylpropyl)amino]- 1,2,3,4,6,7,8,12b-octahydro-6-oxo-pyrido[2,1-a][2]benzazepine-3(S)-carboxylic acid, methyl ester (56 mg, 0.12 mmol) in deoxegenated methanol (3 mL) plus 1N lithium hydroxide (0.50 mL, 0.50 mmol). Stir for 30 minutes under argon atmosphere at ambient temperature. Reduce in volume to 1.5 mL in vacuo, then add, by dropwise addition, to a rapidly stirring solution of 2N hydrochloric acid (2 m). Collect the resulting precipitate, wash with water and dry in a vacuum dessicator for 1 hour. Dry at 35° C. overnight to give the title compound.

EXAMPLE 48

Preparation of [7α(R*), 12bβ]-7-[(S)-(1-Oxo-2(S)-acetylthio-3-phenylpropyl)amino]-1,2,3,4,6,7,8,12b-octahydro-6-oxo-pyrido[2,1-a][2]benzazepine-3(S)-carboxylic acid Mix [7α(R*), 12bβ]-7-[(S)-(1-oxo-2(S)-thio-3-phenylpropyl)amino]- 1,2,3,4,6,7,8,12b-octahydro-6-oxo-pyrido[2,1-a][2]benzazepine-3(S)-carboxylic acid (51 mg, 0.12 mmol) and sulfuric acid (0.3 mL of a 10% solution in acetic acid). Add acetic anhydride (11 mg, 0.12 mmol) over 10 minutes. Warm to 90° C. with stirring for 45 minutes. Allow to cool, pour into diethyl ether and wash with water three times. Separate the organic phase, dry (MgSO₄) and concentrate in vacuo. Purify by silica gel chromatography to give the title compound.

EXAMPLE 49

Preparation of [7α(R*), 12bβ]-7-[(S)-(1-Oxo-2(S)-acetylthio-3-phenylpropyl)amino]-1,2,3,4,6,7,8,12b-octahydro-6-oxo-pyrido[2,1-a][2]benzazepine-3(S)-carboxylic acid, benzyl ester Dissolve [7α(R*), 12bβ]-7-[(S)-(1-oxo-2(S)-acetylthio-3-phenylpropyl)amino]- 1,2,3,4,6,7,8,12b-octahydro-6-oxo-pyrido[2,1-a][2]benzazepine-3(S)-carboxylic acid (2.08 g, 4.33 mmol) in methylene chloride (25 mL) and dry over anhydrous MgSO₄. Filter and wash with methylene chloride (3×200 mL). Evaporate in vacuo to a residue. Dissolve the residue in anhydrous dimethylformamide (25 mL) and place under nitrogen atmosphere. Add cesium carbonate (1.65 g, 5.0 mmole) in one portion. Stir for 45 minutes at ambient temperature. Add benzyl bromide (550 mg, 5.0 mmol). Stir the resulting mixture at ambient temperature for 18 hours. Quench the reaction with ethyl acetate (50 mL) and water (50 mL). Separate the organic phase and wash with water (7×50 mL), ¼ saturated potassium hydrogen carbonate (50 mL), water (50 mL), and saturated sodium chloride (50 mL). Dry (MgSO₄), filter and evaporate in vacuo to give the title compound.

EXAMPLE 50

Preparation of [7α(R*), 12bβ]-7-[(S)-(1-Oxo-2(S)-thio-3-phenylpropyl)amino]-1,2,3,4,6,7,8,12b-octahydro-6-oxo-pyrido-[2,1-a][2]benzazepine-3(S)-carboxylic acid, benzyl ester Stir [7α(R*), 12bβ]-7-[(S)-(1-oxo-2(S)-acetylthio-3-phenylpropyl)amino]- 1,2,3,4,6,7,8,12b-octahydro-6-oxo-pyr-×7÷×-×-ido[2,1-a][2]benzazepine-3(S)-carboxylic acid, benzyl ester (1.87 g, 4 mmol) and saturated methanolic ammonia at ambient temperature until hydrolysis is complete. Evaporate the solvent in vacuo and purify by silica gel chromatography to give the title compound.

The following compounds can be prepared by procedures analogous to those described above in Example 11–50:

[6α(R*), 11bβ]-6-[(S)-(1-oxo-2(R)-benzolythio-3-phenylpropyl)amino]- 1,2,3,5,6,7,11b-heptahydro-5-oxo-pyrrolo[2,1-a][2]benzazepine-2(R)-carboxylic acid, methyl ester;

[6α(R*), 11bβ]-6-[(S)-(1-oxo-2-thio-ethyl)amino]- 1,2,3,5,6,7,11b-heptahydro-5-oxo-pyrrolo[2,1-a][2]benzazepine-2(R)-carboxylic acid;

[6α(R*), 11bβ]-6-[(S)-(1-oxo-2(R)-benzoylthio-3-phenylpropyl)amino]- 1,2,3,5,6,7,11b-heptahydro-5-oxo-pyrrolo[2,1-a][2]benzazepine-2(R)-carboxylic acid;

6α(R*), 11bβ]-6-[(S)-(1-oxo-2(R)-benzoylthio-3-phenylpropyl)amino]- 1,2,3,5,6,7,11b-heptahydro-5-oxo-pyrrolo[2,1-a][2]benzazepine-2(R)-carboxylic acid, benzyl ester;

[6α(R*), 11bβ]-6-[(S)-(1-oxo-2-thio-ethyl)amino]- 1,2,3,5,6,7,11b-heptahydro-5-oxo-pyrrolo[2,1-a][2]benzazepine-2(R)-carboxylic acid, benzyl ester;

6α(R*), 11bβ]-6-[(S)-(1-oxo-(2(S)-benzolythio-3-phenylpropyl)amino]- 1,2,3,5,6,7,11b-heptahydro-5-oxo-pyrrolo[2,1-a][2]benzazepine-2(R)-carboxylic acid, methyl ester;

[6α(R*), 11bβ]-6-[(S)-(1-oxo-2(S)-benzoylthio-3-phenylpropyl)amino]- 1,2,3,5,6,7,11b-heptahydro-5-oxo-pyrrolo[2,1-a][2]benzazepine-2(R)-carboxylic acid;

[6α(R*), 11bβ]-6-[(S)-(1-oxo-2(S)-benzolythio-3-phenylpropyl)amino]- 1,2,3,5,6,7,11b-heptahydro-5-oxo-pyrrolo[2,1-a][2]benzazepine-2(R)-carboxylic acid, benzyl ester;

[7α(R*), 12bβ]-7-[(S)-(1-oxo-2(R)-benzoylthio-3-phenylpropyl)amino]- 1,2,3,4,6,7,8,12b-octahydro-6-oxo-pyrido[2,1-a][2]benzazepine-3(R)-carboxylic acid, methyl ester;

[7α(R*), 12bβ]-7-[(S)-(1-oxo-2-thio-ethyl)amino]- 1,2,3,4,6,7,8,12b-octahydro-6-oxo-pyrido[2,1-a][2]benzazepine-3-(R)-carboxylic acid;

[7α(R*), 12bβ]-7-[(S)-(1-oxo-2(R)-benzoylthio-3-phenylpropyl)amino]- 1,2,3,4,6,7,8,12b-octahydro-6-oxo-pyrido[2,1-a][2]benzazepine-3(R)-carboxylic acid;

[7α(R*), 12bβ]-7-[(S)-(1-oxo-2(R)-benzoylthio-3-phenylpropyl)amino]- 1,2,3,4,6,7,8,12b-octahydro-6-oxo-pyrido-[2,1-a][2]benzazepine-3(R)-carboxylic acid, benzyl ester;

[7α(R*), 12bβ]-7-[(S)-(1-oxo-2-thio-ethyl)amino]- 1,2,3,4,6,7,8,12b-octahydro-6-oxo-pyrido[2,1-a][2]benzazepine-3(R)-carboxylic acid, benzyl ester;

[7α(R*), 12bβ]-7-[(S)-(1-oxo-2(S)-benzoylthio-3-phenylpropyl)amino]- 1,2,3,4,6,7,8,12b-octahydro-6-oxo-pyrido[2,1-a][2]benzazepine-3(R)-carboxylic acid, methyl ester;

[7α(R*), 12bβ]-7-[(S)-(1-oxo-2(S)-benzoylthio-3-phenylpropyl)amino]- 1,2,3,4,6,7,8,12b-octahydro-6-oxo-pyrido[2,1-a][2]benzazepine-3(R)-carboxylic acid;

7α(R*), 12bβ]-7-[(S)-(1-oxo-2(S)-benzolythio-3-phenylpropyl)amino]- 1,2,3,4,6,7,8,12b-octahydro-6-oxo-pyrido[2,1-a][2]benzazepine-3(R)-carboxylic acid, benzyl ester;

6α(R*), 11bβ]-6-[(S)-(1-oxo-2(R)-benzoylthio-3-phenylpropyl)amino]- 1,2,3,5,6,7,11b-heptahydro-5-oxo-pyrrolo[2,1-a][2]benzazepine-2(S)-carboxylic acid, methyl ester;

[6α(R*), 11bβ]-6-[(S)-(1-oxo-2-thio-ethyl)amino]- 1,2,3,5,6,7,11b-heptahydro-5-oxo-pyrrolo[2,1-a][2]benzazepine-2(S)-carboxylic acid;

[6α(R*), 11bβ]-6-[(S)-(1-oxo-2(R)-benzolythio-3-phenylpropyl)amino]- 1,2,3,5,6,7,11b-heptahydro-5-oxo-pyrrolo[2,1-a][2]benzazepine-2(S)-carboxylic acid;

[6α(R*), 11bβ]-6-[(S)-(1-oxo-2(R)-benzoylthio-3-phenylpropyl)amino]- 1,2,3,5,6,7,11b-heptahydro-5-oxo-pyrrolo[2,1-a][2]benzazepine-2(S)-carboxylic acid, benzyl ester;

[6α(R*), 11bβ]-6-[(S)-(1-oxo-2-thio-ethyl)amino]- 1,2,3,5,6,7,11b-heptahydro-5-oxo-pyrrolo[2,1-a][2]benzazepine-2(S)-carboxylic acid, benzyl ester;

[6α(R*), 11bβ]-6-[(S)-(1-oxo-2(S)-benzolythio-3-phenylpropyl)amino]- 1,2,3,5,6,7,11b-heptahydro-5-oxo-pyrrolo[2,1-a][2]benzazepine-2(S)-carboxylic acid, methyl ester;

[6α(R*), 11bβ]-6[(S)-(1-oxo-2(S)-benzoylthio-3-phenylpropyl)amino]- 1,2,3,5,6,7,11b-heptahydro-5-oxo-pyrrolo[2,1-a][2]benzazepine-2(S)-carboxylic acid;

[6α(R*), 11bβ]-6-[(S)-(1-oxo-2(S)-benzoylthio-3-phenylpropyl)amino]- 1,2,3,5,6,7,11b-heptahydro-5-oxo-pyrrolo[2,1-a][2]benzazepine-2(S)-carboxylic acid, benzyl ester;

[7α(R*), 12bβ]-7-[(S)-(1-oxo-2(R)-benzoylthio-3-phenylpropyl)amino]- 1,2,3,4,6,7,8,12b-octahydro-6-oxo-pyrido[2,1-a][2]benzazepine-3(S)-carboxylic acid, methyl ester;

[7α(R*), 12bβ]-7-[(S)-(1-oxo-2-thio-ethyl)amino]- 1,2,3,4,6,7,8,12b-octahydro-6-oxo-pyrido[2,1-a][2]benzazepine-3(S)-carboxylic acid;

[7α(R*), 12bβ]-7-[(S)-(1-oxo-2(R)-benzoylthio-3-phenylpropyl)amino]- 1,2,3,4,6,7,8,12b-octahydro-6-oxo-pyrido[2,1-a][2]benzazepine-3(S)-carboxylic acid;

[7α(R*), 12bβ]-7-[(S)-(1-oxo-2(R)-benzoylthio-3-phenylpropyl)amino]- 1,2,3,4,6,7,8,12b-octahydro-6-oxo-pyrido[2,1-a][2]benzazepine-3(S)-carboxylic acid, benzyl ester;

[7α(R*), 12bβ]-7-[(S)-(1-oxo-2-thio-ethyl)amino]- 1,2,3,4, 6,7,8,12b-octahydro-6-oxo-pyrido[2,1-a][2]benzazepine-3(S)-carboxylic acid, benzyl ester;

[7α(R*), 12bβ]-7-[(S)-(1-oxo-2(S)-benzolythio-3-phenyl-propyl)amino]- 1,2,3,4,6,7,8,12b-octahydro-6-oxo-pyrido[2,1-a][2]benzazepine-3(S)-carboxylic acid, methyl ester;

[7α(R*), 12bβ]-7-[(S)-(1-oxo-2(S)-benzoylthio-3-phenyl-propyl)amino]- 1,2,3,4,6,7,8,12b-octahydro-6-oxo-pyrido[2,1-a][2]benzazepine-3(S)-carboxylic acid;

[7α(R*), 12bβ]-7-[(S)-(1-oxo-2(S)-benzoylthio-3-phenyl-propyl)amino]- 1,2,3,4,6,7,8,12b-octahydro-6oxo-pyrido[2,1-a][2]benzazepine-3(S)-carboxylic acid, benzyl ester.

The compounds of Formula (I) wherein $A_1$ is —$COOR_4$ and $A_2$ is hydrogen and the compounds of Formula (II) wherein X is O, S or NH can be prepared by techniques and procedures well known and appreciated by one of ordinary skill in the art. A general synthetic procedure for preparing these compounds is set forth in Scheme C. In Scheme C, all substituents unless otherwise indicated are as previously defined.

Alternatively, in step b, the appropriate amino compound of structure 28 wherein X is O, S, NH or $(CH_2)_n$ wherein n is 0 or 1 is reacted with the appropriate (R)-thioacetate of structure 30 to give the corresponding (R)-thioacetate compound of structure 32 wherein X is O, S, NH or $(CH_2)_n$ wherein n is 0 or 1 as described previously in Scheme A, step g.

Although Scheme C provides for the preparation of compounds of Formula (I) wherein $A_1$ is (S)-$COOR_4$ and $A_2$ is hydrogen and Formula (II) wherein X is O, S or NH and the 4-carboxy functionality is of the (S)-configuration, the compounds of Formula (I) wherein $A_1$ is (R)-$COOR_4$ or Formula (II) wherein X is O, S, or NH and the 4-carboxy functionality is of the (R)-configuration may be prepared by substituting the appropriate (4R)-carboxy compound amino compound for the amino compound of structure 28 whose preparation is described in Scheme A and Schemes F, G and H vide infra.

The groups $R_3$ and $R_4$ may be manipulated by techniques and procedures well known and appreciated in the art and described previously in Scheme A and Table 1.

Scheme C

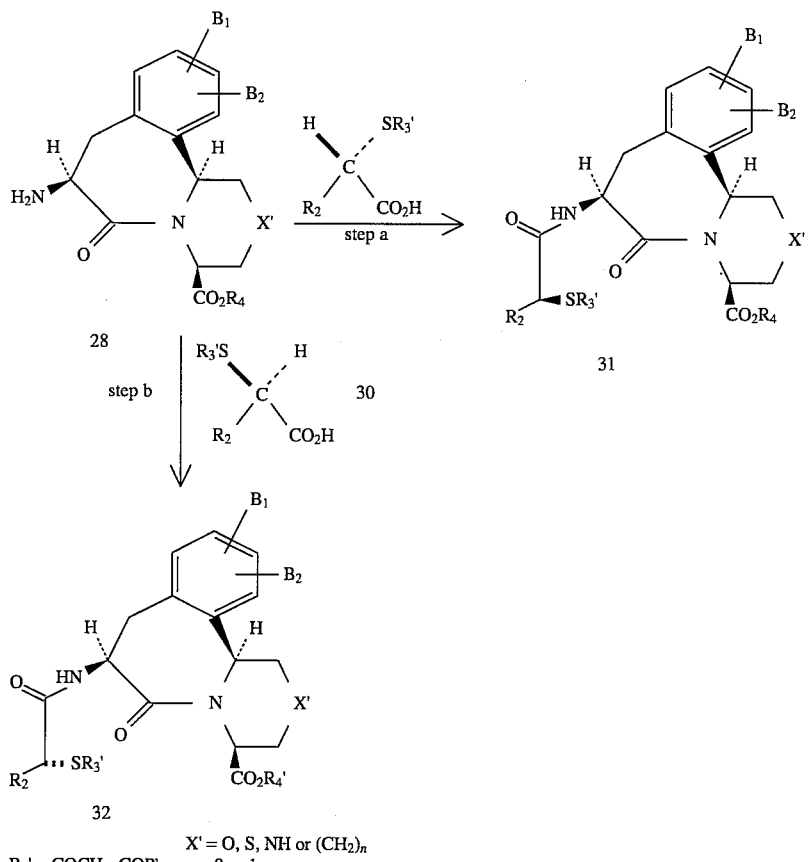

$X' = O, S, NH$ or $(CH_2)_n$
$R_3' = COCH_3, COPh$  $n = 0$ or $1$

Scheme C provides an alternate general synthetic procedure for preparing compounds of Formula (I) wherein $A_1$ is —$COOR_4$ and a general synthetic procedure for preparing the compounds of Formula (II) wherein X is O, S, or NH.

In step a, the appropriate amino compound of structure 28 wherein X is O, S, NH or $(CH_2)_n$ wherein n is 0 or 1 is reacted with the appropriate (S)-thioacetate of structure 29 to give the corresponding (S)-thioacetate compound of structure 31 wherein X is O, S, NH or $(CH_2)_n$ wherein n is 0 or 1 as described previously in Scheme A, step g.

Scheme D provides another general synthetic procedure for preparing compounds of Formula (I) wherein $A_1$ is —$COOR_4$ and $A_2$ is hydrogen and the compounds of Formula (II) wherein X is O, S or NH.

Scheme D

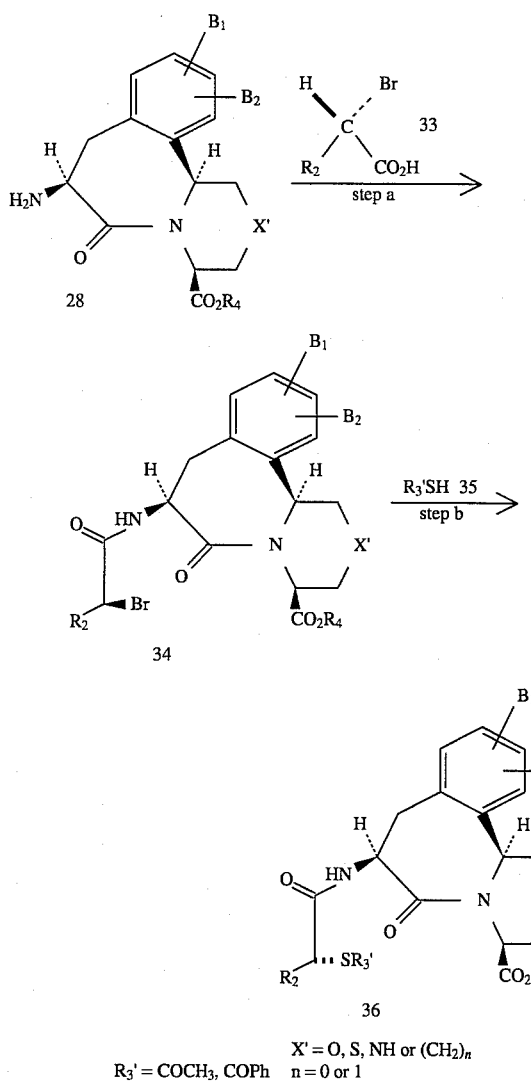

X' = O, S, NH or $(CH_2)_n$
$R_3'$ = $COCH_3$, COPh    n = 0 or 1

In step a, the appropriate amino compound of structure 28 wherein X is O, S, NH or $(CH_2)_n$ wherein n is 0 or 1 is reacted with the appropriate (S)-bromoacid of structure 33 to give the corresponding (S)-bromoamide of structure 34 wherein X is O, S, NH or $(CH_2)_n$ wherein n is 0 or 1 as described previously in Scheme A, step g.

Alternatively the appropriate amino compound of structure 28 wherein X is O, S, NH or $(CH_2)_n$ wherein n is 0 or 1 is reacted with the appropriate (R)-bromoacid to give the corresponding (R)-bromoamide wherein X is O, S, NH or $(CH_2)_n$ wherein n is 0 or 1 or the appropriate amino compound of structure 28 wherein X is O, S, NH or $(CH_2)_n$ wherein n is 0 or 1 is reacted with the appropriate enantiomeric mixture of the bromoacid to give the corresponding enantiomeric mixture of bromoamide wherein X is O, S, NH or $(CH_2)_n$ wherein n is 0 or 1 as described previously in Scheme A, step g.

In step b, the (S)-bromo functionality of the appropriate (S)-bromoamide compound of structure 34 wherein X is O, S, NH or $(CH_2)_n$ wherein n is 0 or 1 is converted to the corresponding (R)-thioacetate or (R)-thiobenzoate of structure 36 wherein X is O, S, NH or $(CH_2)_n$ wherein n is 0 or 1.

For example, the appropriate (S)-bromoamide compound of structure 34 wherein X is O, S, NH or $(CH_2)_n$ wherein n is 0 or 1 is reacted with thiolacetic acid or thiolbenzoic acid of structure 35 in the presence of a base, such as cesium carbonate. The reactants are typically contacted in a suitable organic solvent such as a mixture of dimethylformamide and tetrahydrofuran. The reactants are typically stirred together at room temperature for a period of time ranging from 1 to 8 hours. The resulting (R)-thioacetate or (R)-thiobenzoate of structure 36 wherein X is O, S, NH or $(CH_2)_n$ wherein n is 0 or 1 is recovered from the reaction zone by extractive methods as is known in the art. It may be purified by chromatography.

Alternatively, the (R)-bromo functionality of the appropriate (R)-bromoamide wherein X is O, S, NH or $(CH_2)_n$ wherein n is 0 or 1 is converted to the corresponding (S)-thioacetate or (S)-thiobenzoate wherein X is O, S, NH or $(CH_2)_n$ wherein n is 0 or 1 or the bromo functionality of the appropriate enantiomeric mixture of the bromoamide wherein X is O, S, NH or $(CH_2)_n$ wherein n is 0 or 1 is converted to the corresponding enantiomeric mixture of thioacetate or thiobenzoate compounds wherein X is O, S, NH or $(CH_2)_n$ wherein n is 0 or 1.

Although Scheme D provides for the preparation of compounds of Formula (I) wherein $A_1$ is (S)-$COOR_4$ and $A_2$ is hydrogen and the compounds of Formula (II) wherein X is O, S or NH and the 4-carboxy functionality is of the (S) configuration, the compounds of Formula (I) wherein $A_1$ is (R)-$COOR_4$ or the compounds of Formula (II) wherein X is O, S or NH and the 4-carboxy functionality is of the (R) configuration may be prepared by substituting the appropriate (4R)-carboxy compound amino compound for the amino compound of structure 28 whose preparation is described in Scheme A and Schemes F, G and H infra.

The groups $R_3$ and $R_4$ may be manipulated by techniques and procedures well known and appreciated in the art and described previously in Scheme A and Table 1.

The compounds of Formula (II) wherein X is —$NR_6$ or —$NCOR_7$ can be prepared by techniques and procedures well known and appreciated by one of ordinary skill in the art. A general synthetic procedure for preparing these compounds is set forth in Scheme E. In Scheme E, all substituents unless otherwise indicated are as previously defined.

Scheme E

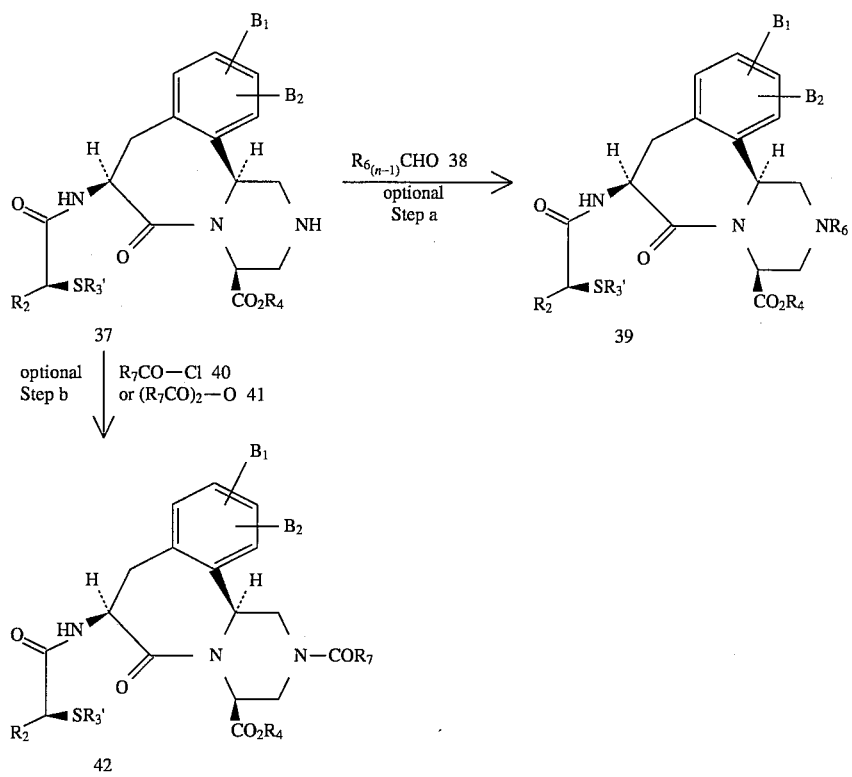

$R_3' = COCH_3$, COPh

Scheme E provides a general synthetic procedure for preparing the compounds of Formula (II) wherein X is —$NR_6$ or —$NCOR_7$.

In optional step a, the amino functionality of the appropriate (S)-thioacetate compound of structure 37 is subjected to reductive alkylation with the appropriate aldehyde of structure 38 using sodium cyanoborohydride, as is well know in the art, to give the corresponding N-alkyl-(S)-thioacetate compound of structure 39.

In optional step b, the amino functionality of the appropriate (S)-thioacetate compound of structure 37 is acylated using the appropriate acyl chloride of structure 40 or the appropriate anhydride of structure 41, as is well known in the art, to give the corresponding N-acyl-(S)-thioacetate compound of structure 42.

Although Scheme E provides for the preparation of compounds of Formula (II) wherein X is —$NR_6$ or —$NCOR_7$ and the 4-carboxy functionality is of the (S) configuration, the compounds of Formula (II) wherein X is —$NR_6$ or —$NCOR_7$ and the 4-carboxy functionality is of the (R) configuration may be prepared by substituting the appropriate (4R)-carboxy (S)-thioacetate compound for the (4S)-carboxy (S)-thioacetate compound of structure 37 whose preparation is described in Scheme F infra.

The corresponding N-alkyl-(R)-thioacetate compounds and N-acyl-(R)-thioacetate compounds may be prepared in a similar fashion by substituting the appropriate (R)-thioacetate compound for the appropriate (S)-thioacetate compound of structure 37 in Scheme E.

The groups $R_3$ and $R_4$ may be manipulated by techniques and procedures well known and appreciated in the art and described previously in Scheme A and shown in Table 1.

Amino compounds of structure 28 wherein X is O may be prepared as described in Scheme F. In Scheme F, all substituents unless otherwise indicated are as previously defined.

Scheme F

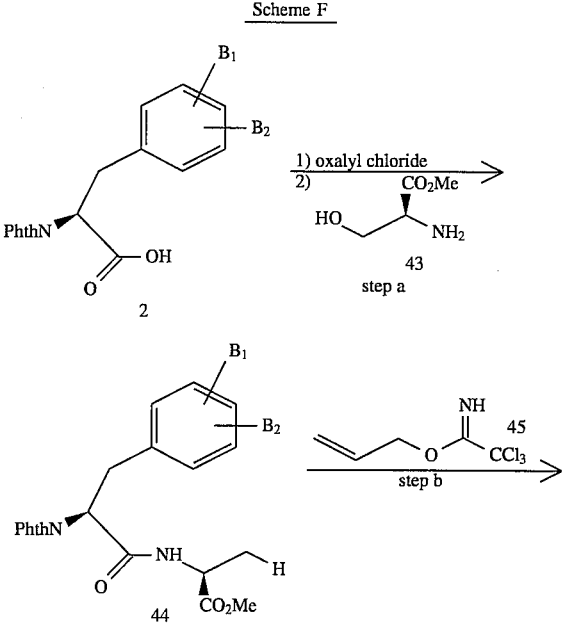

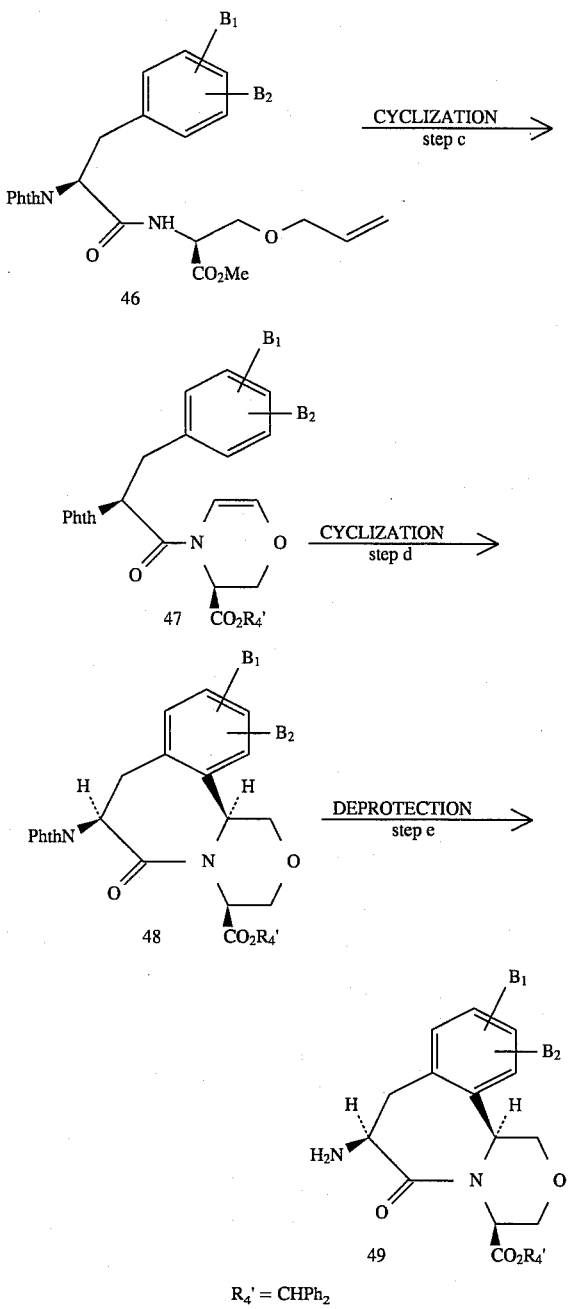

-continued
Scheme F $R_4' = CHPh_2$

Scheme F provides a general synthetic procedure for preparing amino compounds of structure 28 wherein X is O.

In step a, the appropriate phthalimide blocked (S)-phenylalanine derivative of structure 2 is converted to the corresponding acid chloride, then reacted with the appropriate L-serine methyl ester of structure 43 to give the corresponding 1-oxo-3-phenylpropyl-L-serine methyl ester of structure 44 as described previously in Scheme A, step b.

In step b, the hydroxy functionality of the appropriate 1-oxo-3-phenylpropyl-L-serine methyl ester of structure 4 is allylated with the allyl imidate of structure 45 to give the corresponding 1-oxo-3-phenylpropyl-L-serine-O-allyl methyl ester of structure 46.

For example, appropriate 1-oxo-3-phenylpropyl-L-serine methyl ester of structure 44 is contacted with 2 molar equivalents of the allyl imidate of structure 45 and a molar equivalent of a suitable acid such as trifluoromethanesulfonic acid. The reactants are typically contacted in a suitable organic solvent mixture such as methylene chloride/cyclohexane. The reactants are typically stirred together at room temperature under an inert atmosphere for a period of time ranging from 2–24 hours. The 1-oxo-3-phenylpropyl-L-serine-O-allyl methyl ester of structure 46 is recovered from the reaction zone by extractive methods as is known in the art. It may be purified by silica gel chromatography or crystallization.

In step c, the appropriate 1-oxo-3-phenylpropyl-L-serine-O-allyl methyl ester of structure 46 is cyclized to give the corresponding (4S)-enamide of structure 47.

For example, the appropriate 1-oxo-3-phenylpropyl-L-serine-O-allyl methyl ester of structure 46 is first contacted with a molar excess of a mixture of ozone/oxygen. The reactants are typically contacted in a suitable organic solvent mixture such as methylene chloride/methanol. The reactants are typically stirred together for a period of time ranging from 5 minutes to 30 minutes or until a blue color persists and at a temperature range from −78° C. to −40° C. The reaction is quenched with an excess of methylsulfide and the intermediate aldehyde compound recovered from the reaction zone by extractive methods as is known in the art.

The intermediate aldehyde compound is then contacted with trifluoroacetic acid to give the corresponding (4S)-enamine of structure 47 as described previously in Scheme A, step d.

In step d, the appropriate and (4S)-enamine of structure 47 is cyclized to give the corresponding (4S)-tricyclic compound of structure 48 as described previously in Scheme A, step e.

In step e, the phthalimide protecting group of the appropriate (4S)-tricyclic compound of structure 48 is removed to give the corresponding (4S)-amino compound of structure 49 wherein X is O as described in Scheme A, step f.

Alternatively, the appropriate (4R)-amino compound of structure 49 may be prepared by substituting D-serine methyl ester for L-serine methyl ester of structure 43 in step a to give the corresponding 1-oxo-3-phenylpropyl-D-serine methyl ester as described previously in Scheme A, step b. The appropriate 1-oxo-3-phenylpropyl-D-serine methyl ester is then subjected to steps b–f as described previously to give the corresponding (4R)-amino compound of structure 28 wherein X is O.

Amino compounds of structure 28 wherein X is NH may be prepared as described in Scheme G. In Scheme G, all substituents unless otherwise indicated are as previously defined.

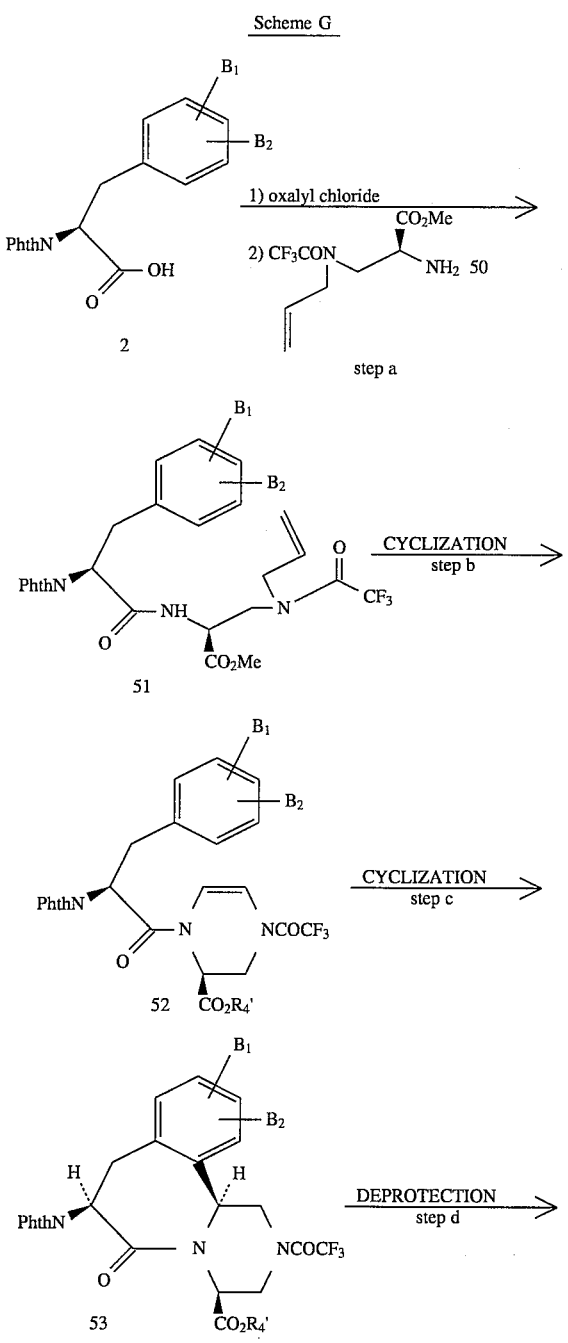

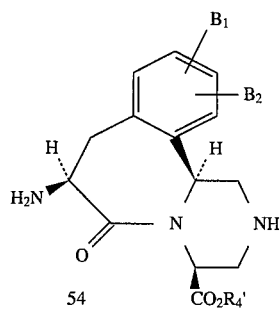

$R_4' = CHPh_2$

Scheme G provides an alternative general synthetic procedure for preparing amino compounds of structure 28 wherein X is NH.

In step a, the appropriate phthalimide blocked (S)-phenylalanine derivative of structure 2 is converted to the corresponding acid chloride, then reacted with the appropriate 3-trifluoracetylamino-3-allyl-L-2-aminopropionic acid, methyl ester of structure 50 to give the corresponding 1-oxo-3-phenylpropyl-N-trifluoroacetyl-N-allyl-L-amino acid, methyl ester of structure 51 as described previously in Scheme A, step b.

3-Trifluoroacetylamino-3-allyl-L-2-aminopropionic acid, methyl ester of structure (50) may be prepared from $N^\alpha$-(benzyloxycarbonyl)-β-(amino)-L-alanine in a 4-step process.

$N^\alpha$-Benzyloxycarbonyl)-β-(amino)-L-alanine is first converted to $N^\alpha$-(benzyloxycarbonyl)-β-(amino)-L-alanine, methyl ester by techniques and procedures well known and appreciated by one of ordinary skill in the art, such as methanol/sulfuric acid esterification.

The β-amino functionality of $N^\alpha$-(benzyloxycarbonyl)-β-(amino)-L-alanine, methyl ester is then allylated with allyl trichloroacetimidate to give the corresponding $N^\alpha$-(benzyloxycarbonyl)-β-(allylamino)-L-alanine, methyl ester using conditions described previously in Scheme F, step b.

The B-allylamine functionality of $N^\alpha$-(benzyloxycarbonyl)-β-(allylamino)-L-alanine, methyl ester is then acylated with trifluoroacetic anhydride as is known in the art to give $N^\alpha$-(benzyloxycarbonyl)-β-(trifluoroacetyl-allylamino)-L-alanine, methyl ester.

The $N^\alpha$-(benzyloxycarbonyl) protecting group is then removed using boron tris(trifluoroacetate)/trifluoroacetic acid as is known in the art to give 3-trifluoracetylamino-3-allyl-L-2-aminopropionic acid, methyl ester of structure (50).

In step b, the appropriate 1-oxo-3-phenylpropyl-N-trifluoroacetyl-N-allyl-L-amino acid methyl ester of structure 51 is cyclized to give the corresponding enamine of structure 52 as described previously in Scheme F, step c.

In step c, the appropriate (4S)-enamine of structure 52 is cyclized to give the corresponding (4S)-tricyclic compound of structure 53 as described previously in Scheme A, step e.

In step d, the phthalimide protecting group of the appropriate (4S)-tricyclic compound of structure 53 is removed to give the corresponding (4S)-amino compound of structure 54 wherein X is NH as described in Scheme A, step f.

Alternatively, the appropriate (4R)-amino compound of structure 54 may be prepared by substituting 3-trifluoroacetylamino- 3-allyl-D-2-aminopropionic acid methyl ester for 3-trifluoroacetylamino-3-allyl-L-2-aminopropionic acid methyl ester of structure 50 in step a to give the corresponding 1-oxo-3-phenylpropyl-N-trifluoroacetyl-N-allyl-D-amino acid methyl ester as described previously in Scheme A, step b. The appropriate 1-oxo-3-phenylpropyl-N-trifluoroacetyl-N-allyl-D-amino acid methyl ester is then subjected to steps b–f as described previously to give the corresponding (R)-amino compound of structure 28 wherein X is NH.

Another method for the preparation of the compounds of Formula (I) wherein $A_1$ is —COOR$_4$, $A_2$ is hydrogen and n=0 is set forth in Scheme H wherein all substituents, unless otherwise indicated, are previously defined.

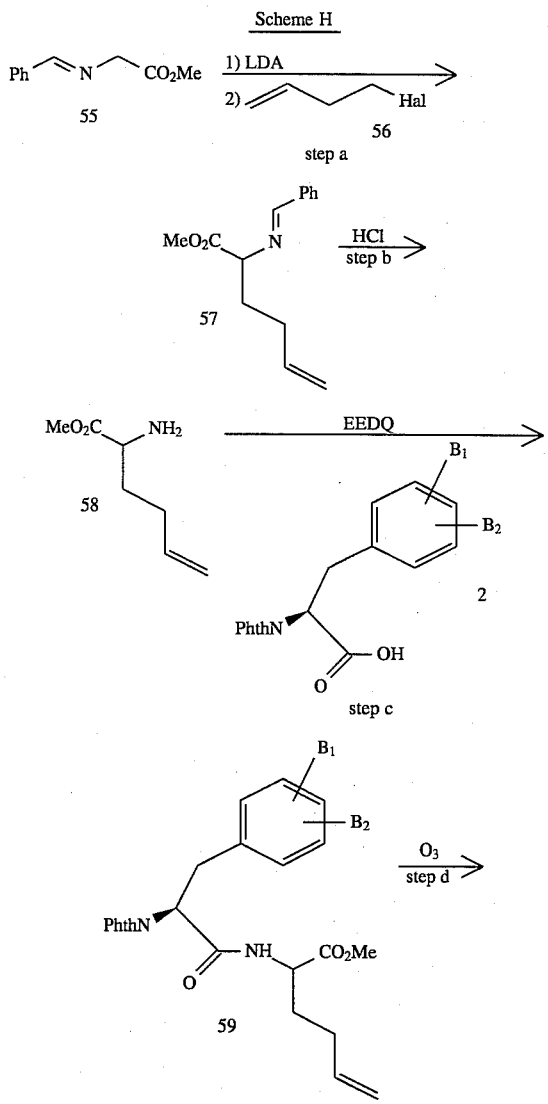

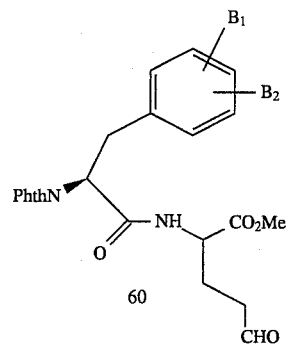

Scheme H provides another general synthetic procedure for preparing compounds of Formula (I) wherein $A_1$ is —COOR$_4$, $A_2$ is hydrogen and n=0.

In step a, the N-(phenylmethylene)glycine methyl ester of structure 55 can be treated with one equivalent of a non-nucleophilic base, such as lithium diisopropylamide, in a suitable aprotic solvent, such as tetrahydrofuran, followed by addition of a 4-halobutene of structure 56 to give 2-(3-butenyl)-N-(phenylmethylene)glycine methyl ester of structure 57.

In step b, the N-(phenylmethylene) functionality of 2-(3-butenyl)-N-(phenylmethylene)glycine methyl ester of structure 57 can be hydrolyzed under acidic conditions, such as with hydrochloric acid in a suitable aprotic solvent, such as ethyl ether to give 2-(3-butenyl)-glycine methyl ester of structure 58.

In step c, the appropriate amide compound of structure 59 can be prepared by reacting the appropriate phthalimide protected (S)-phenylalanine compound of structure 2 (described previously in Scheme A) with 2-(3-butenyl)-glycine methyl ester of structure 57 under coupling reaction conditions as described previously in Scheme B, step c and Scheme A, step b.

In step d, the olefin functionality of the appropriate amide compound of structure 59 can be converted to the appropriate aldehyde compound of structure 60 as described previously in Scheme B, step $d_1$.

The compounds of Formula (I) wherein $A_1$ is —COOR$_4$, $A_2$ is hydrogen, n=0, $R_3$ is acetate or benzoate and $R_4$ is methyl can be prepared from an appropriate aldehyde of structure 60 in a process as outlined previously in Scheme A, steps d–f, Scheme C, steps a or b and Scheme D, steps a or b.

The individual 3(S) and 3(R) esters of the compounds of Formula (I) wherein $A_1$ is —COOR$_4$, $A_2$ is hydrogen, n=0, $R_3$ is acetate or benzoate and $R_4$ is methyl can be prepared from an appropriate aldehyde of structure 60 in a process as outlined previously in Scheme A, steps d, separating the 3(S) and 3(R) esters of the enamine compounds formed from the cyclization reaction described in Scheme A, step d and completing the process as outlined in Scheme A, steps e–f, Scheme C, steps a or b and Scheme D, steps a or b.

The groups $R_3$ and $R_4$ may be manipulated by techniques and procedures well known and appreciated in the art and described previously in Scheme A and Table 1.

Starting materials for use in Scheme C through Scheme H are readily available to one of ordinary skill in the art. For example, (R)- and (S)-3-phenyl-2-acetylthiopropionic acid as described in *J. Org. Chem.*, 51 3664 1986, N$^\alpha$-(benzyloxycarbonyl)-β-(amino)-L-alanine is described in *J. Am. Chem. Soc.*, 107(24) 7105 1985, N-(phenylmethylene)glycine methyl ester is described in *J. Org. Chem.* 41, 3491 1976 and allyl trichloroacetimidate is described in *J. Chem. Soc. Perkin Trans.* 1(11) 2247 1985.

The following examples present typical syntheses as described in Scheme C through H. These examples are understood to be illustrative only and are not intended to limit the scope of the present invention in any way.

EXAMPLE 51

Preparation of [4S-[4α, 7α(R*), 12bβ]]-7-[(1-Oxo-2(S)-acetylthio-3-phenylpropyl)amino]-1,2,3,4,6,7,8,12b-octahydro-6-oxo-pyrido[2,1-a][2]benzazepine-4-carboxylic acid Scheme D, step a: [4S-[4α, 7α(R*), 12bβ]]-7-[(1-Oxo-2(S)-bromo- 3-phenylpropyl)amino]-1,2,3,4,6,7,8,12b-octahydro-6-oxo-pyrido[2,1-a][2]benzazepine-4-carboxylic acid Mix 3-phenyl-2(R)-bromopropionic acid (967 g, 4.22 mmol), tetrahydrofuran (7.74 kg) and N-hydroxysuccinimide (607 g, 5.27 mol) and cool to 5° C. Add, by slow addition over 2.5 hours, a solution of 1,3-dicyclohexylcarbodiimide (828 g, 4.01 mol) in tetrahydrofuran (1.936 kg), maintaining the temperature between −3° and 3° C. Stir for 19 hours, remove 2,3-dicyclohexylurea by vacuum filtration and wash the filter cake with tetrahydrofuran (1.927 kg). Place the filtrate and wash in a 50 L bottom-drain round-bottom flask, add [4S-[4α, 7α(R*), 12bβ]]-7-(amino)-1,2,3,4,6,7,8,12b-octahydro- 6-oxo-pyrido[2,1-a][2]benzazepine-4-carboxylic acid (869 g, 3.17 mol) and stir at 22° C. for 5.5 hours. Add trimethylamine (77 g, 0.75 mol) and stir for an additional 17 hours at 22° C. Dilute with ethyl acetate (10.427 g), wash with 9.94 kg water with 37% hydrochloric acid (214.2 g) and sodium chloride (418 g), then with 12.328 Kg water with sodium chloride (418 g). Dry (MgSO$_4$), filter and wash the filter cake with ethyl acetate (2.193 Kg). Evaporate the solvent in vacuo, add isopropanol (4.210 kg), stir at 12°–16° C. for 17 hour, chill and isolate the product by vacuum filtration. Wash with isopropanol (621 g) and dry to give the title compound 940 g, 61%).

Scheme D, step b: [4S-[4α, 7α(R*), 12bβ]]-7-[(1-Oxo-2(S)-acetylthio- 3-phenylpropyl)amino]-1,2,3,4,6,7,8,12b-octahydro- 6-oxo-pyrido[2,1-a][2]benzazepine-4-carboxylic acid Mix [4S-[4α, 7α(R*), 12bβ]]-7-[(1-oxo-2(S)-bromo-3-phenylpropyl)amino]- 1,2,3,4,6,7,8,12b-octahydro-6-oxo-pyrido[2,1-a][2]benzazepine-4-carboxylic acid (1.052 Kg, 2.17 mol), acetone (13.256 Kg) and thiolacetic acid (207.1 g, 2.72 mol). Cool to −2° C. and add, over approximately 10 minutes, a solution of potassium hydroxide (279.5 g) in water (270 g). Stir at −4° C. for 23 hours, add 1.054 Kg water containing 37% hydrochloric acid (210 g) can evaporate the solvent in vacuo. Dissolve the solid residue in toluene (11.517 Kg) at 43° C., transfer to a 22 L bottom-drain round bottom flask and wash with water (4.067 Kg). Wash at 41° C. with a 4.099 Kg water containing sodium chloride (213 g). Evaporate the solvent in vacuo, dissolve the solid residue in toluene (10.239 Kg), filter and cool. After cooling to −2° C., collect the solid by vacuum filtration, wash with toluene (1.103 Kg) and dry under vacuum at up at 80° C. to give the title compound (859 g, 82.5%).

EXAMPLE 52

Preparation of [4S-[4α, 7α(R*), 12bβ]]-7-[(1-Oxo-2(S)-acetylthio-3-phenylpropyl)amino]-1,2,3,4,6,7,8,12b-hexahydro-6-oxo-1H-[1,4]-oxazino[3,4-a][2]benzazepine-4-carboxylic acid, diphenylmethyl ester Scheme F, step a: N-[2-(1,3-dihydro-1,3-dioxo-2H-isoindol-2-yl)- 1-oxo-3-phenylpropyl]-L-serine, methyl ester Slurry N-phthaloyl-(S)-phenylalanine (90 g, 0.3 mol) in methylene chloride (450 mL) and add, by dropwise addition, oxalyl chloride (54 mL, 0.62 mol). Place under a dry atmosphere (CaSO$_4$ tube) and treat with dimethylformamide (10 µL). Stir for 5 hours, filter and concentrate in vacuo to give N-phthaloyl-(S)-phenylalanine, acid chloride an off white amorphous solid.

Dissolve serine methyl ester hydrochloride (56 g, 0.36 mol) in tetrahydrofuran (300 mL) then cool to 0° C. and add 4-methylmorpholine (88 mL, 0.8 mol). Add, by dropwise addition, a solution of the N-phthaloyl-(S)-phenylalanine, acid chloride in tetrahydrofuran (200 mL). Allow to warm to room temperature and stir for 3 hours. Filter and concentrate the filtrate in vacuo. Dissolve the residue in ethyl acetate and separate the organic phase. Wash with water then saturated sodium chloride and dry (MgSO$_4$). Evaporate the solvent in vacuo to give an oil. Purify by silica gel chromatography (gradient 50% ethyl acetate/hexane to ethyl acetate) to give the title compound (80.8 g, 67%) mp 129°–132° C.

Scheme F, step b: N-[2-(1,3-dihydro-1,3-dioxo-2H-isoindol- 2-yl)-1-oxo-3-phenylpropyl]-O-2-propenyl-L-serine, methyl ester Dissolve N-[2-(1,3-dihydro-1,3-dioxo-2H-isoindol-2-yl)- 1-oxo- 3-phenylpropyl]-L-serine, methyl ester (25 g, 63 mmol) in methylene chloride/cyclohexane (1:1, 600 mL). Add allyl trichloroacetimidate (26 g, 128 mmol) and trifluoromethanesulfonic acid (15 mL), 56.6 mmol). Stir at room temperature under a nitrogen atmosphere for 5 hours and dilute with methylene chloride. Wash with saturated aqueous sodium hydrogen carbonate, water, dry (MgSO$_4$) and evaporate the solvent in vacuo. Purify by silica gel chromatography (gradient 20% ethyl acetate/hexane to 35% ethyl acetate/hexane) to give the title compound; mp 95°–97° C.

Scheme F, step c: [S-(R*, R*)]-N-[2-(1,3-dihydro-1,3-dioxo- 2H-isoindol-2-yl)-1-oxo-3-phenylpropyl]-3,4-dihydro-2H-1,4-oxazino- 3-carboxylic acid, methyl ester Dissolve N-[2-(1,3-dihydro-1,3-dioxo-2H-isoindol-2-yl)- 1-oxo- 3-phenylpropyl]-O-2-propenyl-L-serine, methyl ester (13 g, 29.8 mmol) in methylene chloride/methanol (10:1, 220 mL). Cool to −78° C. and sparge with a mixture of ozone/oxygen for approximately 10 minutes until a blue color persists. Sparge with nitrogen for 10 minutes at −78° C. to remove excess ozone. Treat with methylsulfide (60 mL, 0.82 mol) and allow to warm to room temperature. Stir at room temperature for 2.5 hours, evaporate the solvent in vacuo and dissolve the residue in ethyl acetate (200 mL). Wash with water, saturated sodium chloride, dry (MgSO$_4$) and evaporate the solvent in vacuo to give the intermediate N-[2-(1,3-dihydro-1,3-dioxo-2H-isoindol-2-yl)-1-oxo-3-phenylpropyl]-O- 2-oxoethyl-L-serine, methyl ester as a foam (13.6 g).

Dissolve N-[2-(1,3-dihydro-1,3-dioxo-2H-isoindol-2-yl)-1-oxo- 3-phenylpropyl]-O-2-oxoethyl-L-serine, methyl ester (13.6 g) in methylene chloride/trifluoroacetic acid (10:1/330 mL). Stir at room temperature for 2.5 hours and evaporate the solvent in vacuo. Purify by silica gel chromatography (35% ethyl acetate/hexane) and recrystallize (ethyl acetate/hexane) to give the title compound (8.52 g, 68%); mp 70°–72° C.

Scheme F, step d: [4S-[4α, 7α(R*), 12bβ]]-7-[(1,3-dihydro- 1,3-dioxo-2H-isoindol-2-yl)]-3,4,6,7,8,12b-hexahydro-6-oxo- 1H-[1,4]-oxazino[3,4-a][2]benzazepine-4-carboxylic acid diphenylmethyl ester Dissolve [S-(R*, R*)]-N-[2-(1,3-dihydro-1,3-dioxo-2H-isoindol- 2-yl)-1-oxo-3-phenylpropyl]-3,4-dihydro-2H-1,4-oxazino- 3-carboxylic acid, methyl ester (2.5 g, 5.9 mmol) in methylene chloride (5 mL) and add, by dropwise addition, to a previously prepared solution of trifluoromethanesulfonic acid (4.0 mL, 45 mmol) and trifluoroacetic anhydride (1.0 mL, 7.1 mmol). Place under a nitrogen atmosphere and stir at room temperature for 123 hours. Pour into a separatory funnel containing ice (200 g) and ethyl acetate (200 mL). Separate the organic phase, wash with water (3×200 mL) and saturated aqueous sodium chloride (100 mL). Extract the organic phase with 10% wt. potassium hydrogen carbonate (4×40 mL) and water (40 mL). Layer the combined basic aqueous phases with ethyl acetate (100 mL) and cool in an ice bath. Add, by dropwise addition, 6N hydrochloric acid to adjust the pH to 1 while maintaining the temperature at 5°–10° C. Separate the organic phase and extract the aqueous phase with ethyl acetate (3×200 mL), wash with saturated sodium chloride and dry (MgSO$_4$). Evaporate the solvent in vacuo and dry the residue under high vacuum at 56° C. for 24 hours to give the intermediate [4S-[4α, 7α(R*), 12bβ]]-7-[(1,3-dihydro- 1,3-dioxo-2H-isoindol-2-yl)]-3,4,6,7,8,12b-hexahydro- 6-oxo-1H-[1,4]-oxazino[3,4-a][2]benzazepine-4-carboxylic acid (1.75 g, 73%).

Dissolve [4S-[4α, 7α(R*), 12bβ]]-7-[(1,3-dihydro-1,3-dioxo- 2H-isoindol-2-yl)]-3,4,6,7,8,12b-hexahydro-6-oxo-1H-[1,4]-oxazino[3,4-a][2]benzazepine-4-carboxylic acid (500 mg, 1.23 mmol) in methylene chloride (12 mL) and treat with diphenyldiazomethane (360 mg, 1.86 mmol). Stir for 5.5 hours and evaporate the solvent in vacuo. Purify by silica gel chromatography (gradient 20% ethyl acetate/hexane to 35% ethyl acetate/hexane) to give the title compound (563 mg, 80%); mp 178°–181° C. (isopropanol).

Scheme F, step e: [4S-[4α, 7α(R*), 12bβ]]-7-(amino)-3,4,6,7,8,12b-hexahydro-6-oxo-1H-[1,4]-oxazino[3,4-a][2]benzazepine-4-carboxylic acid, diphenylmethyl ester Dissolve [4S-[4α, 7α(R*), 12bβ]]-7-[(1,3-dihydro-1,3-dioxo- 2H-isoindol-2-yl)]-3,4,6,7,8,12b-hexahydro-6-oxo-1H-[1,4]-oxazino[3,4-a][2]benzazepine-4-carboxylic acid, diphenylmethyl ester (296 mg, 0.517 mmol) in methanol (5 mL) and treat with hydrazine monohydrate (1.1 mL of a 1M solution in methanol, 1.1 mmol). Stir at room temperature for 44 hours, evaporate the solvent in vacuo and slurry the residue in methylene chloride (10 mL). Filter and evaporate the solvent in vacuo to give the title compound (218 mg, 95%).

Scheme C, step a: [4S-[4α, 7α(R*), 12bβ]]-7-[(1-Oxo-2(S)-acetylthio- 3-phenylpropyl)amino]-1,2,3,4,6,7,8,12b-hexahydro- 6-oxo-1H-[1,4]-oxazino[3,4-a][2]benzazepine-4-carboxylic acid, diphenylmethyl ester Dissolve [4S-[4α, 7α(R*), 12bβ]]-7-(amino)-3,4,6,7,8,12b-hexahydro- 6-oxo-1H-[1,4]-oxazino[3,4-a][2]benzazepine-4-carboxylic acid, diphenylmethyl ester (450 mg, 1.018 mmol) and (S)-3-phenyl-2-acetylthiopropionic acid (250 mg, 1.12 mmol) in methylene chloride (10 mL). Add EEDQ (280 mg, 1.13 mmol) and stir at room temperature for 16 hours. Evaporate the solvent in vacuo and purify by silica gel chromatography (gradient 20% ethyl acetate/hexane to 35% ethyl acetate/hexane) to give the title compound (505 mg, 77%).

$^1$H NMR (CDCl$_3$) δ7.44–6.89 (m, 18 H), 6.66–6.63 (m, 2H), 6.31 (s, 1 H), 5.64–5.53 (m, 1 H), 5.10 (d, 1 H), 4.94 (d, 1 H), 4.71 (t, 2 H), 4.37 (t, 1 H), 3.86 (dd, 1 H), 3.77 (dd, 1 H), 3.51 (B part of ABX, 1 H), 3.35 (dd, 1 H), 3.07 (dd, 1 H), 2.51 (A part of ABX, 1 H), 2.40 (s, 3 H).

EXAMPLE 53-MDL-102,179

Preparation of [4S-[4α, 7α(R*), 12bβ]]-7-[(1-Oxo-2(S)-acetylthio-3-phenylpropyl)amino]-1,2,3,4,6,7,8,12b-hexahydro-6-oxo-1H-[1,4]-oxazino[3,4-a][2]-benzazepine-4-carboxylic acid Dissolve [4S-[4α, 7α(R*), 12bβ]]-7-[(1-oxo-2(S)-acetylthio- 3-phenylpropyl)amino]-1,2,3,4,6,7,8,12b-hexahydro-6-oxo-1H-[1,4]-oxazino[3,4-a][2]benzazepine- 4-carboxylic acid, diphenylmethyl ester (505 mg, 0.78 mmol) in methylene chloride (10 mL) and treat with anisole (150 μL, 1.38 mmol) and trifluoroacetic acid (0.8 mL, 10.4 mmol). Stir for 3.25 hours at room temperature under a nitrogen atmosphere. Evaporate the solvent in vacuo and purify by silica gel chromatography (gradient 35% ethyl acetate/hexane to 0.5% acetic acid in ethyl acetate) to give the title compound (349 mg, 93%).

$^1$H NMR (CDCl$_3$) δ7.62–7.00 (m, 10 H), 5.65–5.56 (m, 1H), 5.11 (d, 1 H), 4.77 (d, 1 H, 4.72 (d, 1 H), 4.56 (d, 1 H), 4.35 (t, 1 H), 3.85 (dd, 1 H), 3.74 (dd, 1 H), 3.64 (B part of ABX, 1H), 3.34 (dd, 1 H), 3.05 (dd, 1 H), 2.73 (A part of ABX, 1 H), 2.36 (s, 3 H).

EXAMPLE 54

Preparation of [4S-[4α, 7α(R*), 12bβ]]-7-[(1-Oxo-2(S)-acetylthio-3-phenylpropyl)amino]-1,2,3,4,6,7,8,12b-hexahydro-6-oxo-1H-[1,4]-oxazino[3,4-a][2]benzazepine-4-carboxylic acid, pivaloyloxymethyl ester Dissolve [4S-[4α, 7α(R*), 12bβ]]-7-[(1-oxo-2(S)-acetylthio- 3-phenylpropyl)amino]-1,2,3,4,6,7,8,12b-hexahydro-6-oxo-1H-[1,4]-oxazino[3,4-a][2]benzazepine- 4-carboxylic acid (134 mg, 0.28 mmol) in methylene chloride (3 mL) and dry over anhydrous MgSO$_4$ (60 mg). Filter and wash with methylene chloride (3×200 mL). Evaporate in vacuo to a residue. Dissolve the residue in anhydrous dimethylformamide (2 mL) and place under nitrogen atmosphere. Add cesium carbonate (99 mg, 0.3 mmol) in one portion. Stir for 45 minutes at ambient temperature. Add chloromethyl pivalate (101 mg, 0.67 mmol). Stir the resulting mixture at ambient temperature for 18 hours. Quench the reaction with ethyl acetate (3 mL) and water (0.6 mL). Separate the organic phase and wash with water (7×6 mL), ¼ saturated potassium hydrogen carbonate (6 mL), water (6 mL), and saturated sodium chloride (6 mL). Dry (MgSO$_4$), filter and evaporate in vacuo to yield the title compound.

EXAMPLE 55 MDL-101,519

Preparation of [4S-[4α, 7α(R*), 12bβ]]-7-[(1-Oxo-2(S)-thio-3-phenylpropyl)amino]-1,2,3,4,6,7,8,12b-hexahydro-6-oxo-1H-[1,4]-oxazino[3,4-a][2]benzazepine-4-carboxylic acid Dissolve [4S-[4α, 7α(R*), 12bβ]]-7-[(1-oxo-2(S)-acetylthio-3-phenylpropyl)amino]-1,2,3,4,6,7,8,12b-hexahydro-6-oxo-1H-[1,4]-oxazino[3,4-a][2]benzazepine-4-carboxylic acid (45 mg, 0.093 mmol) in tetrahydrofuran/methanol (1:1, 4 mL) and sparge with nitrogen for 10 minutes at 0° C. Add, by dropwise addition over 4 hours, a solution of lithium hydroxide (0.249 mL of a 1M solution of lithium hydroxide degassed using the freeze-thaw technique). Stir at 0° C. for 7 hours, treat with 1N hydrochloric acid (0.5 mL) at 0° C. and evaporate the solvent in vacuo. Purify by silica gel chromatography (gradient ethyl acetate to 0.2% acetic acid in ethyl acetate) to give the title compound (32.4 mg, 79%).

$^1$H NMR (CDCl$_3$) δ7.67–6.84 (m, 10 H), 5.66–5.56 (m, 1 H), 5.11 (d, 1 H), 4.74 (d, 1 H), 4.74 (d, 1 H), 4.55 (d, 1 H), 3.84 (dd, 1 H), 3.73 (dd, 1 H), 3.68–3.53 (m, 2 H), 3.27 (dd, 1 H), 3.13 (dd, 1 H), 2.76 (A part of ABX, 1 H), 2.06 (d, 1 H).

EXAMPLE 56

Preparation of [4S-[4α, 7α(R*), 12bβ]]-7-[(1-Oxo-2(S)-thio-3-phenylpropyl)amino]-1,2,3,4,6,7,8,12b-hexahydro-6-oxo-1H-[1,4]-oxazino[3,4-a][2]benzazepine-4-carboxylic acid, pivaloyloxymethyl ether ester Dissolve [4S-[4α, 7α(R*), 12bβ]]-7-[(1-oxo-2(S)-acetylthio-3-phenylpropyl)amino]-1,2,3,4,6,7,8,12b-hexahydro-6-oxo-1H-[1,4]-oxazino[3,4-a][2]benzazepine-4-carboxylic acid, pivaloyl methyl ether ester (55 mg, 0.093 mmol) in tetrahydrofuran/methanol (1:1, 4 mL) and sparge with nitrogen for 10 minutes at 0° C. Add, by dropwise addition over 4 hours, a solution of lithium hydroxide (0.249 mL of a 1M solution of lithium hydroxide degassed using the freeze-thaw technique). Stir at 0° C. for 7 hours, treat with 1N hydrochloric acid (0.5 mL) at 0° C. and evaporate the solvent in vacuo. Purify by silica gel chromatography (gradient ethyl acetate to 0.2% acetic acid in ethyl acetate) to give the title compound.

EXAMPLE 57

Preparation of [4S-[4α, 7α(R*), 12bβ]]-7-[(1-Oxo-2(S)-acetylthio-3-phenylpropyl)amino]-1,2,3,4,6,7,8,12b-hexahydro-6-oxo-1H-[1,4]-thiazino[3,4-a][2]benzazepine-4-carboxylic acid, diphenylmethyl ester Dissolve [4S-[4α, 7α(R*), 12bβ]]-7-(amino)-3,4,6,7,8,12b-hexahydro-6-oxo-1H-[1,4]-thiazino[3,4-a][2]benzazepine-4-carboxylic acid, diphenylmethyl ester (466 mg, 1.018 mmol) and (S)-3-phenyl-2-acetylthiopropionic acid (250 mg, 1.12 mmol) in methylene chloride (10 mL). Add EEDQ (280 mg, 1.13 mmol) and stir at room temperature for 16 hours. Evaporate the solvent in vacuo and purify by silica gel chromatography (gradient 20% ethyl acetate/hexane to 35% ethyl acetate/hexane) to give the title compound.

EXAMPLE 58

Preparation of [4S-[4α, 7α(R*), 12bβ]]-7-[(1-Oxo-2(S)-acetylthio-3-phenylpropyl)amino]-1,2,3,4,6,7,8,12b-hexahydro-6-oxo-1H-[1,4]-thiazino[3,4-a][2]benzazepine-4-carboxylic acid Dissolve [4S-[4α, 7α(R*), 12bβ]]-7-[(1-oxo-2(S)-acetylthio-3-phenylpropyl)amino]-1,2,3,4,6,7,8,12b-hexahydro-6-oxo-1H-[1,4]-thiazino[3,4-a][2]benzazepine-4-carboxylic acid, diphenylmethyl ester (515 mg, 0.78 mmol) in methylene chloride (10 mL) and treat with anisole (150 μL, 1.38 mmol) and trifluoroacetic acid (0.8 mL, 10.4 mmol). Stir for 3.25 hours at room temperature under a nitrogen atmosphere. Evaporate the solvent in vacuo and purify by silica gel chromatography (gradient 35% ethyl acetate/hexane to 0.5% acetic acid in ethyl acetate) to give the title compound.

EXAMPLE 59

Preparation of [4S-[4α, 7α(R*), 12bβ]]-7-[(1-oxo-2(S)-thio-3-phenylpropyl)amino-1,2,3,4,6,7,8,12b-hexahydro-6-Oxo-1H-[1,4]-thiazino[3,4-a][2]benzazepine-4-carboxylic acid Dissolve [4S-[4α, 7α(R*), 12bβ]]-7-[(1-oxo-2(S)-acetylthio-3-phenylpropyl)amino]-1,2,3,4,6,7,8,12b-hexahydro-6-oxo-1H-[1,4]-thiazino[3,4-a][2]benzazepine-4-carboxylic acid (459 mg, 0.093 mmol) in tetrahydrofuran/methanol (1:1, 4 mL) and sparge with nitrogen for 10 minutes at 0° C. Add, by dropwise addition over 4 hours, a solution of lithium hydroxide (0.249 mL of a 1M solution of lithium hydroxide degassed using the freeze-thaw technique). Stir at 0° C. for 7 hours, treat with 1N hydrochloric acid (0.5 mL) at 0° C. and evaporate the solvent in vacuo. Purify by silica gel chromatography (gradient ethyl acetate to 0.2% acetic acid in ethyl acetate) to give the title compound.

EXAMPLE 60

Preparation of [4S-[4α, 7α(R*), 12bβ]]-7-[(1-Oxo-2(S)-acetylthio-3-phenylpropyl)amino]-1,2,3,4,6,7,8,12b-hexahydro-6-oxo-1H-[1,4]-azazino[3,4-a][2]benzazepine-4-carboxylic acid, diphenylmethyl ester Scheme G, step a: N-[2-(1,3-dihydro-1,3-dioxo-2H-isoindol-2-yl)-1-oxo-3-phenylpropyl]-(S)-3-[(trifluoroacetyl-2-propenyl)amino]- 2-amino-propionic acid, methyl ester Dissolve N$^α$-(benzyloxycarbonyl)-β-(amino)-L-alanine (47.6 g, 0.2 mol) in methanol (500 mL) and treat with concentrated sulfuric acid (0.5 mL). Heat to 60° C. for 16 hours, cool and reduce the solvent by 50% in vacuo. Dilute with ethyl ether (500 mL), wash with saturated sodium hydrogen carbonate, then brine. Dry (MgSO$_4$) and evaporate the solvent in vacuo to give N$^α$-(benzyloxycarbonyl)-β-(amino)-L-alanine, methyl ester.

Dissolve N$^α$-(benzyloxycarbonyl)-β-(amino)-L-alanine, methyl ester (15.9 g, 63 mmol) in methylene chloride/cyclohexane (1:1, 600 mL). Add allyl trichloroacetimidate (26 g, 128 mmol) and trifluoromethanesulfonic acid (5 mL), 56.6 mmol). Stir at room temperature under a nitrogen atmosphere for 5 hours and dilute with methylene chloride.

Wash with saturated aqueous sodium hydrogen carbonate, water, dry (MgSO$_4$) and evaporate the solvent in vacuo. Purify by silica gel chromatography to give N$^\alpha$-(benzyloxycarbonyl)-β-(allylamino)-L-alanine, methyl ester.

Dissolve N$^\alpha$-(benzyloxycarbonyl)-β-(allylamino)-L-alanine, methyl ester (663 mg, 2.27 mmol) in anhydrous tetrahydrofuran (15 mL). Treat with pyridine (183 μL, 2.27 mmol) followed by trifluoroacetic anhydride (321 μL, 2.27 mmol) and stir at room temperature overnight. Partition between ethyl ether and water. Separate the organic phase, dry (MgSO$_4$) and evaporate the solvent in vacuo. Purify by silica gel chromatography to give N$^\alpha$(benzyloxycarbonyl)-β-(trifluoroacetyl-allylamino)-L-alanine, methyl ester.

Place boron tribromide (215 mg, 0.86 mmol) in a flask and cool to 0° C. Cautiously add trifluoroacetic acid (5 mL) with stirring. Evaporate the solvent to give boron tris(trifluoroacetate).

Dissolve boron tris(trifluoroacetate) (0.3 g, 0.86 mmol) in trifluoroacetic acid (10 mL) and add N$^\alpha$-(benzyloxycarbonyl)-β-(trifluoroacetyl-allylamino)-L-alanine, methyl ester (105 mg, 0.27 mmol). Stir under an argon atmosphere for 1 hour then evaporate the solvent in vacuo at room temperature. Add methanol and evaporate repeatedly to give β-(trifluoroacetyl-allylamino)-L-alanine, methyl ester, hydrochloride.

Dissolve β-(trifluoroacetyl-allylamino)-L-alanine, methyl ester, hydrochloride (104.8 g, 0.36 mmol) in tetrahydrofuran (300 mL) then cool to 0° C. and add 4-methylmorpholine (88 mL, 0.8 mmol). Add, by dropwise addition, a solution of the N-phthaloyl-(S)-phenylalanine, acid chloride (108.7 g, 0.36 mol) in tetrahydrofuran (200 mL). Allow to warm to room temperature and stir for 3 hours. Filter and concentrate the filtrate in vacuo. Dissolve the residue in ethyl acetate and separate the organic phase. Wash with water then saturated sodium chloride and dry (MgSO$_4$). Evaporate the solvent in vacuo to give an oil. Purify by silica gel chromatography to give the title compound.

Scheme G, step b: [S-(R*, R*)]-N-[2-(1,3-dihydro-1,3-dioxo- 2H-isoindol-2-yl)-1-oxo-3-phenylpropyl]-3,4-dihydro-2H-4-trifluoroacetyl- 1,4-azazine-3-carboxylic acid methyl ester Dissolve N-[2-(1,3-dihydro-1,3-dioxo-2H-isoindol-2-yl)-1-oxo- 3-phenylpropyl]-(S)-3-[(trifluoroacetyl-2-propenyl)amino]- 2-amino-propionic acid, methyl ester (15.8 g, 29.8 mmol) in methylene chloride/methanol (10:1, 220 mL). Cool to −78° C. and sparge with a mixture of ozone/oxygen for approximately 10 minutes until a blue color persists. Sparge with nitrogen for 10 minutes at −78° C. to remove excess ozone. Treat with methylsulfide (60 mL, 0.82 mol) and allow to warm to room temperature. Stir at room temperature for 2.5 hours, evaporate the solvent in vacuo and dissolve the residue in ethyl acetate (200 mL). Wash with water, saturated sodium chloride, dry (MgSO$_4$) and evaporate the solvent in vacuo to give the intermediate N-[2-(1,3-dihydro- 1,3-dioxo-2H-isoindol-2-yl)-1-oxo-3-phenylpropyl]-N-2-oxoethyl, methyl ester.

Dissolve N-[2-(1,3-dihydro-1,3-dioxo-2H-isoindol-2-yl)-1-oxo- 3-phenylpropyl]-(S)-3-[(trifluoroacetyl-2-oxoethyl)amino]- 2-amino-propionic acid, methyl ester (15.9 g, 29.8 mmol) in methylene chloride/trifluoroacetic acid (10:1/330 mL). Stir at room temperature for 2.5 hours and evaporate the solvent in vacuo. Purify by silica gel chromatography to give the title compound.

Scheme G, step c: [4S-[4α, 7α(R*), 12bβ]]-7-[(1,3-dihydro- 1,3-dioxo-2H-isoindol-2-yl)]-3,4,6,7,8,12b-hexahydro- 6-oxo- 1H-4-trifluoroacetyl-[1,4]-azazino[3,4-a][2]benzazepine-4-carboxylic acid, diphenylmethyl ester Dissolve [S-(R*, R*)]-N-[2-(1,3-dihydro-1,3-dioxo-2H-isoindol- 2-yl)-1-oxo-3-phenylpropyl]-3,4-dihydro-2H-4-trifluoroacetyl- 1,4-azazine-3-carboxylic acid, methyl ester (3.04 g, 5.9 mmol) in methylene chloride (5 mL) and add, by dropwise addition, to a previously prepared solution of trifluoromethanesulfonic acid (4.0 mL, 45 mmol) and trifluoroacetic anhydride (1.0 mL, 7.1 mmol). Place under a nitrogen atmosphere and stir at room temperature for 123 hours. Pour into a separatory funnel containing ice (200 g) and ethyl acetate (200 mL). Separate the organic phase, wash with water (3×200 mL) and saturated aqueous sodium chloride (100 mL). Extract the organic phase with 10% wt. potassium hydrogen carbonate (4×40 mL) and water (40 mL). Layer the combined basic aqueous phases with ethyl acetate (100 mL) and cool in an ice bath. Add, by dropwise addition, 6N hydrochloric acid to adjust the pH to 1 while maintaining the temperature at 5°–10° C. Separate the organic phase and extract the aqueous phase with ethyl acetate (3×200 mL), wash with saturated sodium chloride and dry (MgSO$_4$). Evaporate the solvent in vacuo and dry the residue under high vacuum at 56° C. for 24 hours to give the intermediate [4S-[4α, 7α(R*), 12bβ]]-7-[(1,3-dihydro-1,3-dioxo-2H-isoindol-2-yl)]- 3,4,6,7,8,12b-hexahydro-6-oxo-1H-4-trifluoroacetyl-[1,4]-oxazino[3,4-a][2]benzazepine-4-carboxylic acid.

Dissolve [4S-[4α, 7α(R*), 12bβ]]-7-[(1,3-dihydro-1,3-dioxo- 2H-isoindol-2-yl)]-3,4,6,7,8,12b-hexahydro-6-oxo-1H-4-trifluoroacetyl-[1,4]-azazino[3,4-a][2]benzazepine-4-carboxylic acid (616 mg, 1.23 mmol) in methylene chloride (12 mL) and treat with diphenyldiazomethane (360 mg, 1.86 mmol). Stir for 5.5 hours and evaporate the solvent in vacuo. Purify by silica gel chromatography to give the title compound.

Scheme G, step e: [4S-[4α, 7α(R*), 12bβ]]-7-(amino)-3,4,6,7,8,12b-hexahydro-6-oxo-1H-[1,4]-azazino[3,4-a][2]benzazepine-4-carboxylic acid, diphenylmethyl ester Dissolve [4S-[4α, 7α(R*), 12bβ]]-7-[(1,3-dihydro-1,3-dioxo- 2H-isoindol-2-yl)]-3,4,6,7,8,12b-hexahydro-6-oxo-1H-4-trifluoroacetyl-[1,4]-azazino[3,4-a][2]benzazepine-4-carboxylic acid, diphenylmethyl ester (345 mg, 0.517 mmol) in methanol (5 mL) and treat with hydrazine monohydrate (1.1 mL of a 1M solution in methanol, 1.1 mmol). Stir at room temperature for 44 hours, evaporate the solvent in vacuo and slurry the residue in methylene chloride (10 mL). Filter and evaporate the solvent in vacuo to give the title compound.

Scheme C, step a: [4S-[4α, 7α(R*), 12bβ]]-7-[(1-Oxo-2(S)-acetylthio- 3-phenylpropyl)amino]-1,2,3,4,6,7,8,12b-hexahydro- 6-oxo-1H-[1,4]-azazino[3,4-a][2]benzazepine-4-carboxylic acid, diphenylmethyl ester Dissolve [4S-[4α, 7α(R*), 12bβ]]-7-(amino-3,4,6,7,8, 12b-hexahydro- 6-oxo-1H-[1,4]-azazino[3,4-a][2]benzazepine-4-carboxylic acid, diphenylmethyl ester (422 mg, 1.018 mmol) and (S)-3-phenyl-2-acetylthiopropionic acid (250 mg, 1.12 mmol) in methylene chloride (10 mL). Add EEDQ (280 mg, 1.13 mmol) and stir at room temperature for 16 hours. Evaporate the solvent in vacuo and purify by silica gel chromatography to give the title compound.

EXAMPLE 61

Preparation of [4S-[4α, 7α(R*), 12bβ]]-7-[(1-Oxo-2(S)-acetylthio-3-phenylpropyl)amino]-1,2,3,4,6,7,8,12b-hexahydro-6-oxo-1H-[1,4]-azazino[3,4-a][2]benzazepine-4-carboxylic acid Dissolve [4S-[4α, 7α(R*), 12bβ]]-7-[(1-oxo-2(S)-acetylthio- 3-phenylpropyl)amino]-1,2,3,4,6,7,8,12b- hexahydro-6-oxo-1H-[1,4]-azazino[3,4-a][2]benzazepine-4-carboxylic acid, diphenylmethyl ester (484 mg, 0.78 mmol) in methylene chloride (10 mL) and treat with anisole (150 μL, 1.38 mmol) and trifluoroacetic acid (0.8 mL, 10.4 mmol). Stir for 3.25 hours at room temperature under a nitrogen atmosphere. Evaporate the solvent in vacuo and purify by silica gel chromatography to give the title compound.

EXAMPLE 62

Preparation of [4S-[4α, 7α(R*), 12bβ]]-7-[(1-Oxo-2(S)-thio-3-phenylpropyl)amino]-1,2,3,4,6,7,8,12b-hexahydro-6-oxo-1H-[1,4]-azazino[3,4-a][2]benzazepine-4-carboxylic acid Dissolve [4S-[4α, 7α(R*), 12bβ]]-7-[(1-oxo-2(S)-acetylthio-3-phenylpropyl)amino]-1,2,3,4,6,7,8,12b-hexahydro-6-oxo-1H-[1,4]-azazino[3,4-a][2]benzazepine-4-carboxylic acid (42 mg, 0.093 mmol) in tetrahydrofuran/methanol (1:1, 4 mL) and sparge with nitrogen for 10 minutes at 0° C. Add, by dropwise addition over 4 hours, a solution of lithium hydroxide (0.249 mL of a 1M solution of lithium hydroxide degassed using the freeze-thaw technique). Stir at 0° C. for 7 hours, treat with 1N hydrochloric acid (0.5 mL) at 0° C. and evaporate the solvent in vacuo. Purify by silica gel chromatography to give the title compound.

EXAMPLE 63

Preparation of [4S-[4α, 7α(R*), 12bβ]]-7-[(1-Oxo-2(S)-acetylthio-3-phenylpropyl)amino]-1,2,3,4,6,7,8,12b-hexahydro-6-oxo-1H-[1,4]-$N^4$-trifluoroacetyl-azazino[3,4-a][2]benzazepine-4-carboxylic acid, diphenylmethyl ester Dissolve [4S-[4α, 7α(R*), 12bβ]]-7-[(1-Oxo-2(S)-thio-3-phenylpropyl)amino]-1,2,3,4,6,7,8,12b-hexahydro-6-oxo-1H-[1,4]-azazino[3,4-a][2]benzazepine-4-carboxylic acid (979 mg, 2.27 mmol) in anhydrous tetrahydrofuran (15 mL). Treat with pyridine (183 μL, 2.27 mmol) followed by trifluoroacetic anhydride (321 μL, 2.27 mmol) and stir at room temperature overnight. Partition between ethyl ester and water. Separate the organic phase, dry (MgSO₄) and evaporate the solvent in vacuo. Purify by silica gel chromatography to give the title compound.

EXAMPLE 64

[6α(R*), 11bβ]-6-[(S)-(1-Oxo-2(R)-benzoylthio-3-phenylpropyl) amino]-1,2,3,5,6,7,11b-heptahydro-5-oxo-pyrrolo[2,1-a][2] benzazepine-3(S)-carboxylic acid, methyl ester Scheme H, step a: N-(Phenylmethylene)-2-(3-butenyl)glycine methyl ester Dissolve diisopropylamine (15.4 mL, 110 mmol) in tetrahydrofuran (250 mL), place under a nitrogen atmosphere and cool to −78° C. Add n-butyllithium (39 mL of a 2.7M solution in hexane, 105 mmol). Stir for 30 minutes and add, by dropwise addition, a solution of N-(phenylmethylene)glycine methyl ester (17.7 g, 100 mmol) in tetrahydrofuran (25 mL). Stir for 15 minutes and add 4-bromobutene (13.4 g, 100 mmol) and allow to warm slowly to room temperature. Add hexamethylphosphoramide (20 mL, 100 mmol) and stir under a nitrogen atmosphere for 3 hours. Pour into water, extract into ethyl ether and wash with brine several times. Dry (MgSO₄) and evaporate the solvent in vacuo to give the title compound as an amber oil (25 g).

Scheme H, step b: 2-(3-Butenyl)glycine methyl ester

Dissolve N-(phenylmethylene)-2-(3-butenyl)glycine methyl ester (25 g) in ethyl ether (400 mL) and stir with 1N hydrochloric acid (150 mL) and water (150 mL). Place under an argon atmosphere and stir for 2 hours. Separate the aqueous phase and adjust to pH 9, extract into chloroform, dry and evaporate the solvent in vacuo to give the title compound as a light oil (4.5 g).

Scheme H, step c: (S)-N-[2-(1,3-Dihydro-1,3-dioxo-2H-isoindol-2-yl)-1-oxo-3-phenylpropyl]-2-(3-butenyl)-glycine, methyl esters Dissolve N-phthaloyl-(S)-phenylalanine (2) (6.0 g, 20 mmol) and EEDQ (6.0 g, 24 mmol) in methylene chloride (30 mL). Add 2-(3-butenyl)glycine methyl ester (3.0 g, 21 mmol) and stir for 18 hours. Pour into methylene chloride, wash with 10% hydrochloric acid then saturated sodium hydrogen carbonate. Dry and evaporate the solvent in vacuo to give 8.3 g yellow oil. Purify by silica gel chromatography (25% ethyl acetate/hexane) to give a diastereomeric mixture of the title compounds as foam (5.2 g).

Scheme H, step d: (S)-N-[2-(1,3-Dihydro-1,3-dioxo-2H-isoindol-2-yl)]-phenylalanyl]-2-(3-oxopropyl)glycine, methyl esters Dissolve the diastereomeric mixture of (S)-N-[2-(1,3-dihydro-1,3-dioxo-2H-isoindol-2-yl)-1-oxo-3-phenylpropyl]-2-(3-butenyl)-glycine, methyl esters (4.2 g, 10 mmol) in methylene chloride (100 mL) and absolute methanol (10 mL). Cool to −78° C. and treat with ozone until blue. Degas with nitrogen and add methyl sulfide (10 mL) and pyridine (0.5 mL). Allow to warm slowly to room temperature and stir for 18 hours. Wash with 10% hydrochloric acid then brine. Dry and evaporate the solvent in vacuo to give a diastereomeric mixture of the title compounds as an oil (4.5 g).

Scheme A, step d: (S)-N-[2-(1,3-Dihydro-1,3-dioxo-2H-isoindol-2-yl)]-1-oxo-3-phenylpropyl-1,2,3-trihydro-2(S)-pyrrolecarboxylic acid, methyl ester and (S)-N-[2-(1,3-Dihydro-1,3-dioxo-2H-isoindol-2-yl)]-1-oxo-3-phenylpropyl-1,2,3-trihydro-2(R)-pyrrolecarboxylic acid, methyl ester Dissolve the diastereomeric mixture of (S)-N-[2-(1,3-dihydro-1,3-dioxo-2H-isoindol-2-yl)]-phenylalanyl]-2-(3-oxopropyl)glycine, methyl esters (4.5 g) in 1,1,1-trichloroethane (150 mL) and treat with trifluoroacetic acid (0.5 mL). Heat at reflux for 18 hours, evaporate the solvent and purify by silica gel chromatography (80% ethyl acetate/hexane) to give the 2(S)-title compound (700 mg) and the 2(R)-title compound (600 mg).

Scheme A, Step e: [6α(R*), 11bβ]-6-[(S)-(1,3-Dihydro-1,3-dioxo-2H-isoindol-2-yl)]-1,2,3,5,6,7,11b-heptahydro-5-oxo-pyrrolo[2,1-a][2]benzazepine-3(S)-carboxylic acid, methyl ester Dissolve (S)-N-[2-(1,3-dihydro-1,3-dioxo-2H-isoindol-2-yl)]-1-oxo-3-phenylpropyl-1,2,3-trihydro-2(S)-pyrrolecarboxylic acid, methyl ester (338 mg, 0.836 mmol) in anhydrous methylene chloride (10 mL) and add to trifluoromethanesulfonic acid (5 mL). Stir for 3.5 hours, cool in an ice bath and carefully add water (25 mL). Extract with ethyl acetate (75 mL) and wash with saturated sodium hydrogen carbonate (25 mL). Dry (Na₂SO₄) and evaporate the solvent in vacuo. Purify by silica gel chromatography (1:1 ethyl acetate/hexane to 2:1 ethyl acetate/hexane) to give the title compound as a white foam (314 mg, 93%).

Scheme A, Step f: [6α(R*), 11bβ]-6-[(S)-Amino]- 1,2,3,5,6,7,11b-heptahydro-5-oxo-pyrrolo-[2,1-a][2]benzazepine-3(S)-carboxylic acid, methyl ester Dissolve [6α(R*), 11bβ]-6-[(S)-(1,3-dihydro-1,3-dioxo-2H-isoindol- 2-yl)]-1,2,3,5,6,7,11b-heptahydro-5-oxo-pyrrolo[2,1-a][2benzazepine-3(S)-carboxylic acid, methyl ester (244 mg, 0.603 mmol) in methanol (3 mL), treat with hydrazine monohydrate (0.70 mL of a 1M solution in methanol) and stir at room temperature for 24 hours. Add additional hydrazine monohydrate (0.3 mL of a 1M solution in methanol) and stir for 48 hours. Filter through filter aid, evaporate the solvent in vacuo and add methylene chloride. Filter slowly through filter aid ($MgSO_4$) and evaporate the solvent in vacuo to give the title compound as a yellow oil (181 mg).

Scheme C, step b: [6α(R*), 11bβ]-6-[(S)-(1-Oxo-2(R)-benzoylthio- 3-phenylpropyl)amino]-1,2,3,5,6,7,11b-heptahydro- 5-oxo-pyrrolo[2,1-a][2]benzazepine-3(S)-carboxylic acid, methyl ester Dissolve (R)-3-phenyl-2-benzoylthiopropionic acid (242 mg, 0.845 mmol) in methylene chloride (6 mL), cool in an ice-methanol bath and treat with oxalyl chloride (0.94 mL, 11 mmol). Stir for 1.5 hours and evaporate the solvent in vacuo at 0°–5° C. Dilute the residue with methylene chloride (3 mL) and add a solution of [6α(R*), 11bβ]-6-[(S)-Amino]-1,2,3,5,6,7,11b-heptahydro-5-oxo-pyrrolo[2,1-a][2]benzazepine-3(S)-carboxylic acid, methyl ester (155 mg, 0.565 mmol) in methylene chloride (6 mL). Add pyridine (68 μL, 0.85 mmol) and stir for 2 hours. Dilute with ethyl acetate (60 mL) and wash with 1N hydrochloric acid (30 mL) and saturated sodium hydrogen carbonate (2×30 mL). Dry ($MgSO_4$), evaporate the solvent in vacuo and purify by silica gel chromatography (3:2 hexane/ethyl acetate) to give the title compound as a white solid (159 g, 53.1%).

EXAMPLE 65

Preparation of [6α(R*), 11bβ]-6-[(S)-(1-Oxo-2(R)-thio-3-phenylpropyl)amino]-1,2,3,5,6,7,11b-heptahydro-5-oxo-pyrrolo[2,1-a][2]benzazepine-3(S)-carboxylic acid Dissolve [6α(R*), 11bβ]-6-[(1-oxo-2(R)-benzoylthio-3-phenylpropyl)amino]- 1,2,3,5,6,7,11b-heptahydro-5-oxo-pyrrolo[2,1-a][2]benzazepine-3(S)-carboxylic acid, methyl ester (52 mg, 0.098 mmol) in methanol (1.5 mL) and degas at 0° C. Add aqueous lithium hydroxide (0.6 mL of a 1N degassed solution, 0.6 mmol) at 0° C. Add tetrahydrofuran to obtain solution (4 mL) and stir for 17 hours at room temperature. Cool in an ice bath and add 1N hydrochloric acid (1 mL). Partition between methylene chloride (30 mL) and water (15 mL) and separate the organic phase. Dry ($Na_2SO_4$), evaporate the solvent in vacuo and purify by silica gel chromatography (2:1 hexane/ethyl acetate) to give the title compound as a white solid (32.2 g, 77%).

EXAMPLE 66

Preparation of [4S-[4α, 7α(R*), 12bβ]]-7-[(1-Oxo-2(R)-acetylthio-3-(3,4-methylenedioxyphenyl)propyl)amino]-1,2,3,4,6,7,8,12b-octahydro-6-oxopyrido[2,1-a][2]benzazepine-4-carboxylic acid, diphenylmethyl ester and [4S-[4α, 7α(R*), 12bβ]]-7-[(1-Oxo-2(S)-acetylthio-3-( 3,4-methylenedioxyphenyl)propyl)amino]-1,2,3,4,6,7,8,12b-octahydro-6-oxopyrido[2,1-a][2]benzazepine-4-carboxylic acid, diphenylmethyl ester Scheme D, step a: [4S-[4α, 7α(R*), 12bβ]]-7-[(1-oxo-2(R)-bromo- 3-(3,4-methylenedioxyphenyl)propyl)amino]-1,2,3,4,6,7,8,12b-octahydro-6-oxo-pyrido[2,1-a][2]benzazepine-4-carboxylic acid, diphenylmethyl ester and [4S-[4α, 7α(R*), 12bβ]]-7-[(1-oxo-2(S)-bromo-3-( 3,4-methylenedioxyphenyl)propyl)amino]-1,2,3,4,6,7,8,12b-octahydro-6-oxo-pyrido[2,1-a][2]benzazepine-4-carboxylic acid, diphenylmethyl ester Stir powdered methylenedioxy cinnamic acid (19.2 g, 210 mmol) in glacial acetic acid (200 mL) at room temperature while adding a solution of bromine (16 g, 100 mmol) in acetic acid (50 mL) over 30 minutes. Stir the homogeneous yellow solution for 15 minutes and add a solution of sodium cyabiborohydride (20 g) in water (50 mL) over 30 minutes. Stir for 48 hours at room temperature. Add water (70 mL) and stir for an additional 2 hours. Filter and wash the filtercake with acetic acid/water. Evaporate the solvent in vacuo and partition the residue between chloroform and water. Dry the organic phase ($MgSO_4$) and evaporate the solvent in vacuo. Redissolve the residue in chloroform, filter and evaporate the solvent in vacuo to give 3-(3,4-methylenedioxyphenyl)- 2-bromopropionic acid as a crystalline solid (15.1 g).

Mix 3-(3,4-methylenedioxyphenyl)-2-bromopropionic acid (273 mg, 1.0 mmol) and [4S-[4α, 7α(R*), 12bβ]]-7-(amino)- 1,2,3,4,6,7,8,12b-octahydro-6-oxopyrido[2,1-a][2]benzazepine-4-carboxylic acid, diphenylmethyl ester (441 mg, 1.0 mmol) in methylene chloride (6 mL). Add EEDQ (247 mg, 1.0 mmol). Stir for 15 hours at ambient temperature under argon atmosphere. Dilute with ethyl acetate (25 mL) and wash with 5% sulfuric acid (15 mL), then saturated sodium hydrogen carbonate (15 mL). Dry ($Na_2SO_4$), concentrate in vacuo and purify by silica gel chromatography (2:1 hexane/ethyl acetate) to yield the mixture of title compounds as a white foam (695 mg).

Scheme D, step b: [4S-[4α, 7α(R*), 12bβ]]-7-[(1-Oxo-2(R)-acetylthio- 3-(3,4-methylenedioxyphenyl)propyl)amino]- 1,2,3,4,6,7,8,12b-octahydro-6-oxopyrido[2,1-a] [2]benzazepine-4-carboxylic acid, diphenylmethyl ester and [4S-[4α, 7α(R*), 12bβ]]-7-[(1-Oxo-2(S)-acetylthio-3-( 3,4-methylenedioxyphenyl)propyl)amino]-1,2,3,4,6,7,8,12b-octahydro- 6-oxopyrido[2,1-a][2]benzazepine-4-carboxylic acid, diphenylmethyl ester Dissolve thiolacetic acid (0.10 mL, 1.4 mmol) in methanol (5 mL) and treat with cesium carbonate (228 mg, 0.70 mmol). Stir the yellow solution for 30 minutes then evaporate the solvent in vacuo. Dilute the resulting cesium salt with dimethylformamide (10 mL) and treat with a solution of a mixture of [4S-[4α, 7α(R*), 12bβ]]-7-[(1-oxo-2(R)-bromo-3-( 3,4-methylenedioxyphenyl)propyl)amino]1,2,3, 4,6,7,8,12b-octahydro- 6-oxo-pyrido[2,1-a][2]benzazepine-4-carboxylic acid, diphenylmethyl ester and [4S-[4α, 7α(R*), 12bβ]]-7-[( 1-oxo-2(S)-bromo-3-(3,4-methylenedioxyphenyl)propyl)amino]- 1,2,3,4,6,7,8,12b-octahydro-6-oxo-pyrido[2,1-a][2]benzazepine-4-carboxylic acid, diphenylmethyl ester (694 mg, 1.0 mmol) in tetrahydrofuran (6 mL). Stir at room temperature for 2 hours, evaporate the solvent in vacuo and partition between ethyl acetate (75 mL) and brine (50 mL). Dry the organic phase (Na$_2$SO$_4$), evaporate the solvent in vacuo and purify by chromatography (3:2 to 1:1 hexane/ethyl acetate) to give the mixture of title compounds as a tan foam (648 mg, 94%).

EXAMPLE 67

Preparation of [4S-[4α, 7α(R*), 12bβ]]-7-[(1-Oxo-2(R)-acetylthio-3-(3,4-methylenedioxyphenyl)propyl)amino]-1,2,3,4,6,7,8,12b-octahydro-6-oxopyrido[2,1-a][2]benzazepine-4-carboxylic acid and [4S-[4α, 7α(R*), 12bβ]]-7-[1-Oxo-2(S)-acetylthio-3-(3,4-methylenedioxyphenyl)propyl)amino]-1,2,3,4,6,7,8,12b-octahydro-6-oxopyrido[2,1-a][2]benzazepine-4-carboxylic acid Dissolve [4S-[4α, 7α(R*), 12bβ]]-7-[(1-Oxo-2(R)-acetylthio- 3-(3,4-methylenedioxyphenyl)propyl)amino]-1, 2,3,4,6,7,8,12b-octahydro- 6-oxopyrido[2,1-a][2]benzazepine-4-carboxylic acid, diphenylmethyl ester and [4S-[4α, 7α(R*), 12bβ]]-7-[( 1-Oxo-2(S)-acetylthio-3-(3,4-methylenedioxyphenyl)propyl)amino]- 1,2,3,4,6,7,8,12b-octahydro- 6-oxopyrido[2,1-a][2]benzazepine-4-carboxylic acid, diphenylmethyl ester (535 mg, 0.775 mmol) in methylene chloride (10 mL), cool in an ice bath and treat with anisole (0.84 mL, 7.8 mmol) and then trifluoroacetic acid (5 mL). Stir for 1 hour under nitrogen atmosphere, partition between ethyl acetate and brine. Dry (Na$_2$SO$_4$), evaporate the solvent in vacuo and purify by chromatography (1:1 to 1:2 hexane/ethyl acetate plus 1% acetic acid) to give the title compounds (419 mg).

EXAMPLE 68

Preparation of [4S-[4α, 7α(R*), 12bβ]]-7-[(1-Oxo-2(R)-thio-3-(3,4-methylenedioxyphenyl)propyl)amino]-1,2,3,4, 6,7,8,12b-octahydro-6-oxopyrido[2,1-a][2]benzazepine-4-carboxylic acid and [4S-[4α, 7α(R*), 12bβ]]-7-[(1-Oxo-2(S)-thio-3-(3,4-methylenedioxyphenyl)propyl)amino]-1,2,3,4,6,7, 8,12b-octahydro-6-oxopyrido[2,1-a][2]benzazepine-4-carboxylic acid Dissolve [4S-[4α, 7α(R*), 12bβ]]-7-[(1-Oxo-2(R)-acetylthio- 3-(3,4-methylenedioxyphenyl)propyl)amino]-1, 2,3,4,6,7,8,12b-octahydro- 6-oxopyrido[2,1-a][2]benzazepine-4-carboxylic acid and [4S-[4α, 7α(R*), 12bβ]]-7-[(1-Oxo-2(S)-acetylthio-3-( 3,4-methylenedioxyphenyl)propyl)amino]-1,2,3,4,6,7,8,12b-octahydro- 6-oxopyrido[2,1-a][2]benzazepine-4-carboxylic acid (0.145 mmol) in methanol (3 mL) and tetrahydrofuran (2 mL), cool in an ice bath and add lithium hydroxide (0.6 mL of a 1M solution, 0.6 mmol). Stir the reaction mixture for 3 hours and add 1N hydrochloric acid. Partition between methylene chloride (75 mL) and water (25 mL). Dry (Na$_2$SO$_4$), evaporate solvent in vacuo and purify by chromatography (Hexane:ethyl acetate/Acetic acid: 1:1:1%) to give the title compounds as a white solid (61 mg, 87%).

EXAMPLE 69

Preparation of [4S-[4α, 7α(R*), 12bβ]]-7-[(1-Oxo-2(S)-acetylthio-3-phenylpropyl)amino]-1,2,3,4,6,7,8,12b-octahydro-6-oxo-pyrido[2,1-a][2]benzazepine-4-carboxylic acid, diphenylmethyl ester Scheme D, step a: [4S-[4α, 7α(R*), 12bβ]]-7-[(1-oxo-2(R)-bromo- 3-phenylpropyl)amino]-1,2,3,4,6,7,8,12b-octahydro-6-oxo-pyrido[2,1-a][2]benzazepine-4-carboxylic acid, diphenylmethyl ester Mix D-phenylalanine (186.4 g, 1.128 mol) and 49% hydrobromic acid (372.8 g), cool to −5° C. and add, by dropwise addition, a solution of sodium nitrite (77.9 g) in water (565 mL) over a period of about 1 hour (vigorous gas evolution). Stir at −5° C. to 0° C. for 4 hours, extract into ethyl ether (3×1 L), dry (MgSO$_4$) and evaporate the solvent in vacuo. Purify by chromatography (5% acetic aci/95% methylene chloride) and distillation to give 3-phenyl-2(R)-bromopropionic acid (112 g, 43%); bp 128°–135° C. @ 0.25 torr.

Mix 3-phenyl-2(R)-bromopropionic acid (7.25 g, 25 mmol) and [4S-[4α, 7α(R*), 12bβ]]-7-(amino)-1,2,3,4,6,7, 8,12b-octahydro- 6-oxopyrido[2,1-a][2]benzazepine-4-carboxylic acid, diphenylmethyl ester (9.0 g, 21 mmol) in methylene chloride (25 mL). Add EEDQ (6.18 g, 25 mmol). Stir for 18 hours at ambient temperature under nitrogen atmosphere. Dilute with methylene chloride and wash with dilute hydrochloric acid (2×200 mL), then saturated sodium hydrogen carbonate. Dry (MgSO$_4$), concentrate in vacuo and triturate with 30% ethyl acetate/hexane and purify by silica gel chromatography (hexane/ethyl acetate) to yield the title compound (10.5 g, 77%).

Scheme D, step b: [4S-[4α, 7α(R*), 12bβ]]-7-[(1-Oxo-2(S)-acetylthio- 3-phenyl)propylamino]-1,2,3,4,6,7,8,12b-octahydro- 6-oxopyrido[2,1-a][2]benzazepine-4-carboxylic acid, diphenylmethyl ester Dissolve thiolacetic acid (1.04 g, 13.4 mmol) in methanol (10 mL) and treat with cesium carbonate (2.2 g, 6.75 mmol). Stir the yellow solution until homogeneous then evaporate the solvent in vacuo. Dissolve the resulting cesium slat in dimethylformamide (10 mL) and treat with [4S-[4α, 7α(R*), 12bβ]]-7-[(1-oxo-2(R)-bromo-3-phenylpropyl)amino]- 1,2,3,4,6,7,8,12b-octahydro-6-oxo-pyrido[2,1-a][2]benzazepine-4-carboxylic acid, diphenylmethyl ester (8.8 g, 13.5 mmol). Stir at room temperature for 4 hours, pour into ethyl acetate, wash with water, then brine. Dry the organic phase (MgSO$_4$), evaporate the solvent in vacuo and purify by chromatography to give the title compound as a light yellow foam (7.1 g, 81%).

EXAMPLE 70

Preparation of [4S-[4α, 7α(R*), 12bβ]]-7-[(1-Oxo-2(S)-acetylthio-3-phenylpropyl)amino]-1,2,3,4,6,7,8,12b-octahydro-6-oxopyrido[2,1-a][2]benzazepine-4-carboxylic acid Dissolve [4S-[4α, 7α(R*), 12bβ]]-7-[(1-Oxo-2(S)-acetylthio- 3-phenyl)propylamino]-1,2,3,4,6,7,8,12b-octahydro-6-oxopyrido[2,1-a][2]benzazepine-4-carboxylic acid, diphenylmethyl ester (7.1 g, 11 mmol) in methylene chloride (15 mL), cool to −20° C. and treat with anisole (2 mL, 7.8 mmol) and then trifluoroacetic acid (8 mL). Stir for 2 hour under nitrogen atmosphere, partition between ethyl acetate and brine. Dry (MgSO$_4$), evaporate the solvent in vacuo and purify by chromatography to give the title compound (4.55 g 86%).

The following compounds can be prepared by procedures analogous to those described above in Example 51–70:

[4S-[4α, 7α(R*), 12bβ]]-7-[(1-Oxo-2(R)-thio-3-phenylpropyl)amino]- 1,2,3,4,6,7,8,12b-hexahydro-6-oxo-1H-[1,4]-oxazino[3,4-a][2]benzazepine-4-carboxylic acid, pivaloyloxymethyl ester;

[4S-[4α, 7α(R*), 12bβ]]-7-[(1-Oxo-2(R)-acetylthio-3-phenylpropyl)amino]- 1,2,3,4,6,7,8,12b-hexahydro-6-oxo-1H-[1,4]-oxazino[3,4-a][2]benzazepine-4-carboxylic acid, pivaloyloxymethyl ester;

[4S-[4α, 7α(R*), 12bβ]]-7-[(1-Oxo-2(R)-thio-3-phenylpropyl)amino]- 1,2,3,4,6,7,8,12b-hexahydro-6-oxo-1H-[1,4]-thiazino[3,4-a][2]benzazepine-4-carboxylic acid

[4S-[4α, 7α(R*), 12bβ]]-7-[(1-Oxo-2(R)-thio-3-phenylpropyl)amino]- 1,2,3,4,6,7,8,12b-hexahydro-6-oxo-1H-[1,4]-thiazino[3,4-a][2]benzazepine-4-carboxylic acid, pivaloyloxymethyl ester;

[4S-[4α, 7α(R*), 12bβ]]-7-[(1-Oxo-2(R)-acetylthio-3-phenylpropyl)amino]- 1,2,3,4,6,7,8,12b-hexahydro-6-oxo-1H-[1,4]-thiazino[3,4-a][2]benzazepine-4-carboxylic acid, pivaloyloxymethyl ester;

[4S-[4α, 7α(R*), 12bβ]]-7-[(1-Oxo-2(R)-thio-3-phenylpropyl)amino]- 1,2,3,4,6,7,8,12b-hexahydro-6-oxo-1H-[1,4]-azazino[3,4-a][2]benzazepine-4-carboxylic acid, pivaloyloxymethyl ester;

[4S-[4α, 7α(R*), 12bβ]]-7-[(1-Oxo-2(R)-thio-3-phenylpropyl)amino]- 1,2,3,4,6,7,8,12b-hexahydro-6-oxo-1H-[1,4]-$N^4$-benzoyl-azazino[3,4-a][2]benzazepine-4-carboxylic acid, pivaloyloxymethyl ester;

[4S-[4α, 7α(R*), 12bβ]]-7-[(1-Oxo-2(R)-acetylthio-3-phenylpropyl)amino]- 1,2,3,4,6,7,8,12b-hexahydro-6-oxo-1H-[1,4]-$N^4$-benzoyl-azazino[3,4-a][2]benzazepine-4-carboxylic acid, pivaloyloxymethyl ester;

[6α(R*), 11bβ]-6-[(S)-(1-oxo-2(R)-benzoylthio-3-phenylpropyl)amino]- 1,2,3,5,6,7,11b-heptahydro-5-oxo-pyrrolo[2,1-a][2]benzazepine-3(R)-carboxylic acid, methyl ester;

[6α(R*), 11bβ]-6-[(S)-(1-oxo-2-thio-ethyl)amino]- 1,2,3,5,6,7,11b-heptahydro-5-oxo-pyrrolo[2,1-a][2]benzazepine-3(R)-carboxylic acid;

[6α(R*), 11bβ]-6-[(S)-(1-oxo-2(R)-benzoylthio-3-phenylpropyl)amino]- 1,2,3,5,6,7,11b-heptahydro-5-oxo-pyrrolo[2,1-a][2]benzazepine-3(R)-carboxylic acid;

6α(R*), 11bβ]-6-[(S)-(1-oxo-2(R)-benzoylthio-3-phenylpropyl)amino]- 1,2,3,5,6,7,11b-heptahydro-5-oxo-pyrrolo[2,1-a][2]benzazepine-3(R)-carboxylic acid, benzyl ester;

[6α(R*), 11bβ]-6-[(S)-(1-oxo-2-thio-ethyl)amino]- 1,2,3,5,6,7,11b-heptahydro-5-oxo-pyrrolo[2,1-a][2]benzazepine-3(R)-carboxylic acid, benzyl ester;

[6α(R*), 11bβ]-6-[(S)-(1-oxo-2(S)-benzoylthio-3-phenylpropyl)amino]- 1,2,3,5,6,7,11b-heptahydro-5-oxo-pyrrolo[2,1-a][2]benzazepine-3(R)-carboxylic acid, methyl ester;

[6α(R*), 11bβ]-6-[(S)-(1-oxo-2(S)-benzoylthio-3-phenylpropyl)amino]- 1,2,3,5,6,7,11b-heptahydro-5-oxo-pyrrolo[2,1-a][2]benzazepine-3(R)-carboxylic acid;

[6α(R*), 11bβ]-6-[(S)-(1-oxo-2(S)-benzoylthio-3-phenylpropyl)amino]- 1,2,3,5,6,7,11b-heptahydro-5-oxo-pyrrolo[2,1-a][2]benzazepine-3(R)-carboxylic acid, benzyl ester;

[6α(R*), 11bβ]-6-[(S)-(1-oxo-2-thio-ethyl)amino]- 1,2,3,5,6,7,11b-heptahydro-5-oxo-pyrrolo[2,1-a][2]benzazepine-3(S)-carboxylic acid;

[6α(R*), 11bβ]-6-[(S)-(1-oxo-2(R)-benzoylthio-3-phenylpropyl)amino]- 1,2,3,5,6,7,11b-heptahydro-5-oxo-pyrrolo[2,1-a][2]benzazepine-3(S)-carboxylic acid, benzyl ester;

[6α(R*), 11bβ]-6-[(S)-(1-oxo-2-thio-ethyl)amino]- 1,2,3,5,6,7,11b-heptahydro-5-oxo-pyrrolo[2,1-a][2]benzazepine-3(S)-carboxylic acid, benzyl ester;

[6α(R*), 11bβ]-6-[(S)-(1-oxo-2(S)-benzoylthio-3-phenylpropyl)amino]- 1,2,3,5,6,7,11b-heptahydro-5-oxo-pyrrolo[2,1-a][2]benzazepine-3(S)-carboxylic acid, methyl ester;

[6α(R*), 11bβ]-6-[(S)-(1-oxo-2(S)-benzoylthio-3-phenylpropyl)amino]- 1,2,3,5,6,7,11b-heptahydro-5-oxo-pyrrolo[2,1-a][2]benzazepine-3(S)-carboxylic acid;

[6α(R*), 11bβ]-6-[(S)-(1-oxo-2(S)-benzoylthio-3-phenylpropyl)amino]- 1,2,3,5,6,7,11b-heptahydro-5-oxo-pyrrolo[2,1-a][2]benzazepine-3(S)-carboxylic acid, benzyl ester;

[6α(R*), 11bβ]-6-[(S)-(1-oxo-2(R)-benzoylthio-3-phenylpropyl)amino]- 1,2,3,5,6,7,11b-heptahydro-5-oxo-pyrrolo[2,1-a][2]benzazepine-3(S)-carboxylic acid, methyl ester;

[6α(R*), 11bβ]-6-[(S)-(1-oxo-2(S)-thio-3-phenylpropyl)amino]- 1,2,3,5,6,7,11b-heptahydro-5-oxo-pyrrolo[2,1-a][2]benzazepine-3(S)-carboxylic acid, pivaloyloxymethyl ester;

[6α(R*), 11bβ]-6-[(S)-(1-oxo-2(S)-acetylthio-3-phenylpropyl)amino]- 1,2,3,5,6,7,11b-heptahydro-5-oxo-pyrrolo[2,1-a][2]benzazepine-3(S)-carboxylic acid, pivaloyloxymethyl ester. In a further embodiment, the present invention provides a method of inhibiting enkephalinase in a patient in need thereof comprising administering to said patient an effective enkephalinase inhibitory amount of a compound of Formulas (I) or (II).

As used herein, the term "patient" refers to warm-blooded animals or mammals, including mice, rats and humans. A patient is in need of treatment to inhibit enkephalinase when the patient is suffering from acute or chronic pain and is in need of an endorphin- or enkephalin-mediated analgesic effect. In addition, a patient is in need of treatment to inhibit enkephalinase when the patient is suffering from a disease state characterized by abnormalities in fluid, electrolyte, blood pressure, intraocular pressure, renin, or aldosterone homeostasis, such as, but not limited to, hypertension, renal diseases, hyperaldosteronemia, cardiac hypertrophy, glaucoma and congestive heart failure. In these instances the patient is in need of an ANP-mediated diuretic, natriuretic, hypotensive, hypoaldosteronemic effect. Inhibition of enkephalinase would provide an endorphin- or enkephalin-mediated analgesic effect by inhibiting the metabolic degradation of endorphins and enkephalins. Inhibition of enkephalinase would provide an ANP-mediated diuretic, natriuretic, hypotensive, hypoaldosteronemic effect by inhibiting the metabolic degradation of ANP. Inhibition of enkephalinase would also potentiate endogenous levels of bradykinin. Inhibition of enkephalinase would also modulate intestinal smooth muscle contractility and would be useful in the treatment of irritable bowel syndrome.

In addition, a patient is in need of treatment to inhibit enkephalinase when the patient is in need of an antidepressant effect or a reduction in severity of withdrawal symptoms associated with termination of opiate or morphine administration.

The identification of those patients who are in need of treatment to inhibit enkephalinase is well within the ability and knowledge of one skilled in the art. A clinician skilled in the art can readily identify, by the use of clinical tests, physical examination and medical/family history, those patients who are in need of an endorphin- or enkephalin-mediated analgesic effect or who are in need of an ANP-mediated diuretic, natriuretic, hypotensive or hypoaldosteronemic effect.

An effective enkephalinase inhibitory amount of a compound of Formula (I) or (II) is an amount which is effective in inhibiting enkephalinase and in thus inhibiting the metabolic degradation of the naturally-occurring circulating regulatory peptides such as the endorphins, including enkephalins, and ANP. Successful treatment is also understood to include prophylaxis in treating a patient in those instances such as, for example, in a pre-operative procedure, where a patient will be suffering from acute or chronic pain in the near future.

An effective enkephalinase inhibitory amount of a compound of Formula (I) or (II) is an amount which is effective in inhibiting enkephalinase in a patient in need thereof which results, for example, in endorphin- or enkephalin-mediated analgesic effects or in ANP-mediated diuretic, natriuretic, hypotensive, hypoaldosteronemic effect.

An effective enkephalinase inhibitory dose can be readily determined by the use of conventional techniques and by observing results obtained under analogous circumstances. In determining the effective dose, a number of factors are considered including, but not limited to: the species of patient; its size, age, and general health; the specific disease involved; the degree of or involvement of the severity of the disease; the response of the individual patient; the particular compound administered; the mode of administration; the bioavailability characteristics of the preparation administered; the dose regimen selected; and the use of concomitant medication.

An effective enkephalinase inhibitory amount of a compound of Formula (I) or (II) will generally vary from about 0.01 milligram per kilogram of body weight per day (mg/kg/day) to about 20 mg/kg/day. A daily dose of from about 0.1 mg/kg to about 10 mg/kg is preferred.

In addition, the present invention further provides a method of inhibiting ACE in a patient in need thereof comprising administering to said patient an effective ACE inhibitory amount of a compound of Formula (I) or (II). A patient is in need of treatment to inhibit ACE when the patient is suffering from hypertension, chronic congestive heart failure, hyperaldosteronemia or cognitive disorders. Inhibition of ACE reduces levels of angiotensin II and thus inhibits the vasopressor, hypertensive and hyperaldosteronemic effects caused thereby. An effective ACE inhibitory amount of a compound of Formula (I) or (II) is that amount which is effective in inhibiting ACE in a patient in need thereof which results, for example, in a hypotensive effect. An effective ACE inhibitory amount and an effective ACE inhibitory dose are the same as that described above for an effective enkephalinase inhibitory amount and dose.

In addition, the present invention further provides a method for treating a patient suffering from smooth cell proliferation. An effective smooth cell proliferation inhibitory amount of a compound Formula (I) or (II) is that amount which is effective in inhibiting smooth cell proliferation in a patient in need thereof which results, for example, in a reduced myointimal thickening after vascular injury. An effective smooth cell proliferation inhibitory amount and an effective smooth cell proliferation inhibitory dose are the same as that described above for an effective enkephalinase inhibitory amount and dose.

In effecting treatment of a patient, compounds of Formula (I) or (II) can be administered in any form or mode which makes the compound bioavailable in effective amounts, including oral and parenteral routes. For example, the compound can be administered orally, subcutaneously, intramuscularly, intravenously, transdermally, intranasally, rectally, and the like. Oral administration is generally preferred. One skilled in the art of preparing Formulations can readily select the proper form and mode of administration depending upon the disease state to be treated, the stage of the disease, and other relevant circumstances.

Compounds of Formula (I) or (II) can be administered in the form of pharmaceutical compositions or medicaments which are made by combining the compounds of Formula (I) or (II) with pharmaceutically acceptable carriers or excipients, the proportion and nature of which are determined by the chosen route of administration, and standard pharmaceutical practice.

In another embodiment, the present invention provides compositions comprising a compound of Formula (I) or (II) in admixture or otherwise in associated with one or more inert carriers. These compositions are useful, for example, as assay standards, as convenient means of making bulk shipments, or as pharmaceutical compositions. An assayable amount of a compound of Formula (I) or (II) is an amount which is readily measurable by standard assay procedures and techniques as are well known and appreciated by those skilled in the art. Assayable amounts of a compound of Formula (I) or (II) will generally vary from about 0.001% to about 75% of the composition by weight. Inert carriers can be any material which does not degrade or otherwise covalently react with a compound of Formulas (I) or (II). Examples of suitable inert carriers are water; aqueous buffers, such as those which are generally useful in High Performance Liquid Chromatography (HPLC) analysis; organic solvents, such as acetonitrile, ethyl acetate, hexane and the like; and pharmaceutically acceptable carriers or excipients.

More particularly, the present invention provides pharmaceutical compositions comprising an effective amount of a compound of Formula (I) or (II) in admixture or otherwise in association with one or more pharmaceutically acceptable carriers or excipients.

The pharmaceutical compositions or medicaments are prepared in a manner well known in the pharmaceutical art. The carrier or excipient may be a solid, semi-solid, or liquid material which can serve as a vehicle or medium for the active ingredient. Suitable carriers or excipients are well known in the art. The pharmaceutical composition may be adapted for oral or parenteral use and may be administered to the patient in the form of tablets, capsules, suppositories, solution, suspensions, or the like.

The pharmaceutical compositions may be administered orally, for example, with an inert diluent or with an edible carrier. They may be enclosed in gelatin capsules or compressed into tablets. For the purpose of oral therapeutic administration, the compounds of Formula (I) or (II) may be incorporated with excipients and used in the form of tablets, troches, capsules, elixirs, suspensions, syrups, wafers, chewing gums and the like. These preparations should contain at least 4% of the compound of Formula (I) or (II), the active ingredient, but may be varied depending upon the particular form and may conveniently be between 4% to about 70% of the weight of the unit. The amount of the active ingredient present in compositions is such that a unit dosage form suitable for administration will be obtained.

The tablets, pills, capsules, troches and the like may also contain one or more of the following adjuvants: binders, such as microcrystalline cellulose, gum tragacanth or gelatin; excipients, such as starch or lactose, disintegrating agents such as alginic acid, Primogel, corn starch and the like; lubricants, such as magnesium stearate or Sterotex; glidants, such as colloidal silicon dioxide; and sweetening agents, such as sucrose or saccharin may be added or flavoring agents, such as peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the active ingredient, sucrose as a sweetening agent and certain preservatives, dyes and colorings and flavors. Materials used in preparing these various compositions should be pharmaceutically pure and non-toxic in the amounts used.

For the purpose of parenteral administration, the compounds of Formula (I) or (II) may be incorporated into a solution or suspension. These preparations should contain at least 0.1% of a compound of the invention, but may be varied to be between 0.1 and about 50% of the weight thereof. The amount of the active ingredient present in such compositions is such that a suitable dosage will be obtained.

The solutions or suspensions may also include one or more of the following adjuvants; sterile diluents such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of toxicity such as sodium chloride or dextrose. The parenteral preparation can be enclosed in ampules, disposable syringes or multiple dose vials made of glass or plastic.

As with any group of structurally related compounds which possess a particular generic utility, certain groups and configurations are preferred for compounds of Formula (I) or (II) in their end-use application.

The compounds of Formula (I) or (II) wherein $B_1$ is hydrogen or alkoxy are preferred. The compounds of Formula (I) or (II) wherein $B_2$ is hydrogen or alkoxy are preferred. In addition, compounds of Formula (II) wherein Z is —O— are preferred.

It is, of course, understood that the compounds of Formula (I) or (II) may exist in a variety of isomeric configurations including structural as well as stereo isomers. It is further understood that the present invention encompasses those compounds of Formula (I) or (II) in each of their various structural and stereo isomeric configurations as individual isomers and as mixtures of isomers.

The following specific compounds of Formula (I) and (II) are particularly preferred in the end-use application of the compounds of the present invention:

[4S-[4α, 7α(R*), 12bβ]]-7-[(1-oxo-2(S)-thio-3-phenylpropyl)amino]- 1,2,3,4,6,7,8,12b-octahydro-6-oxo-pyrido[2,1-a][2]benzazepine-4-carboxylic acid;

[4S-[4α, 7α(R*), 12bβ]]-7-[(1-oxo-2(R)-thio-3-phenylpropyl)amino]- 1,2,3,4,6,7,8,12b-octahydro-6-oxo-pyrido[2,1-a][2]benzazepine-4-carboxylic acid;

[4S-[4α, 7α(R*), 12bβ]]-7-[(1-oxo-2-thio-ethyl)amino]-1,2,3,4,6,7,8,12b-octahydro-6-oxo-pyrido[2,1-a][2]benzazepine-4-carboxylic acid;

[4S-[4α, 7α(R*), 12bβ]]-7-[(1-oxo-2(R)-thio-2-phenylethyl)amino]- 1,2,3,4,6,7,8,12b-octahydro-6-oxo-pyrido[2,1-a][2]benzazepine-4-carboxylic acid;

[4S-[4α, 7α(R*), 12bβ]]-7-[(1-oxo-2(S)-thio-2-phenylethyl)amino]- 1,2,3,4,6,7,8,12b-octahydro-6-oxo-pyrido[2,1-a][2]benzazepine-4-carboxylic acid;

[6α(R*), 11bβ]-6-[(S)-(1-oxo-2(S)-thio-3-phenylpropyl)amino]- 1,2,3,5,6,7,11b-heptahydro-5-oxo-pyrrolo[2,1-a][2]benzazepine-3(S)-carboxylic acid;

[6α(R*), 11bβ]-6-[(S)-(1-oxo-2(R)-thio-3-phenylpropyl)amino]- 1,2,3,5,6,7,11b-heptahydro-5-oxo-pyrrolo[2,1-a][2]benzazepine-3(S)-carboxylic acid;

[4S-[4α, 7α(R*), 12bβ]]-7-[(1-oxo-2(S)-acetylthio-3-phenylpropyl)amino]- 1,2,3,4,6,7,8,12b-octahydro-6-oxo-pyrido[2,1-a][2]benzazepine-4-carboxylic acid;

[4S-[4α, 7α(R*), 12bβ]]-7-[(1-oxo-2(R)-acetylthio-3-phenylpropyl)amino]- 1,2,3,4,6,7,8,12b-octahydro-6-oxo-pyrido[2,1-a][2]benzazepine-4-carboxylic acid;

[4S-[4α, 7α(R*), 12bβ]]-7-[(1-oxo-2-acetylthio-ethyl)amino]- 1,2,3,4,6,7,8,12b-octahydro-6-oxo-pyrido[2,1-a][2]benzazepine-4-carboxylic acid;

[4S-[4α, 7α(R*), 12bβ]]-7-[(1-oxo-2(R)-acetylthio-2-phenylethyl)amino]- 1,2,3,4,6,7,8,12b-octahydro-6-oxo-pyrido[2,1-a][2]benzazepine-4-carboxylic acid;

[4S-[4α, 7α(R*), 12bβ]]-7-[(1-oxo-2(S)-acetylthio-2-phenylethyl)amino]- 1,2,3,4,6,7,8,12b-octahydro-6-oxo-pyrido[2,1-a][2]benzazepine-4-carboxylic acid;

[6α(R*), 11bβ]-6-[(S)-(1-oxo-2(S)-acetylthio-3-phenylpropyl)amino]- 1,2,3,5,6,7,11b-heptahydro-5-oxo-pyrrolo[2,1-a][2]benzazepine-3(S)-carboxylic acid;

[6α(R*), 11bβ]-6-[(S)-(1-oxo-2(R)-acetylthio-3-phenylpropyl)amino]- 1,2,3,5,6,7,11b-heptahydro-5-oxo-pyrrolo[2,1-a][2]benzazepine-3(S)-carboxylic acid;

[4S-[4α, 7α(R*), 12bβ]]-7-[(1-oxo-2(S)-acetylthio-3-phenylpropyl)amino]- 1,2,3,4,6,7,8,12b-octahydro-6-oxo-pyrido[2,1-a][2]benzazepine-4-carboxylic acid, pivaloyloxymethyl ester;

[4S-[4α, 7α(R*), 12bβ]]-7-[(1-oxo-2(R)-acetylthio-3-phenylpropyl)amino]- 1,2,3,4,6,7,8,12b-octahydro-6-oxo-pyrido[2,1-a][2]benzazepine-4-carboxylic acid, pivaloyloxymethyl ester;

[4S-[4α, 7α(R*), 12bβ]]-7-[(1-oxo-2-acetylthio-ethyl)amino]- 1,2,3,4,6,7,8,12b-octahydro-6-oxo-pyrido[2,1-a][2]benzazepine-4-carboxylic acid, pivaloyloxymethyl ester;

[4S-[4α, 7α(R*), 12bβ]]-7-[(1-oxo-2(R)-acetylthio-2-phenylethyl)amino]- 1,2,3,4,6,7,8,12b-octahydro-6-oxo-pyrido[2,1-a][2]benzazepine-4-carboxylic acid, pivaloyloxymethyl ester;

[4S-[4α, 7α(R*), 12bβ]]-7-[(1-oxo-2(S)-acetylthio-2-phenylethyl)amino]- 1,2,3,4,6,7,8,12b-octahydro-6-oxo-pyrido[2,1-a][2]benzazepine-4-carboxylic acid, pivaloyloxymethyl ester;

[6α(R*), 11bβ]-6-[(S)-(1-oxo-2(S)-acetylthio-3-phenylpropyl)amino]- 1,2,3,5,6,7,11b-heptahydro-5-oxo-pyrrolo[2,1-a][2]benzazepine-3(S)-carboxylic acid, pivaloyloxymethyl ester;

[6α(R*), 11bβ]-6-[(S)-(1-oxo-2(R)-acetylthio-3-phenylpropyl)amino]- 1,2,3,5,6,7,11b-heptahydro-5-oxo-pyrrolo[2,1-a][2]benzazepine-3(S)-carboxylic acid, pivaloyloxymethyl ester;

[4S-[4α, 7α(R*), 12bβ]]-7-[(1-Oxo-2(S)-thio-3-phenylpropyl)amino]- 1,2,3,4,6,7,8,12b-hexahydro-6-oxo-1H-[1,4]-oxazino[3,4-a][2]benzazepine-4-carboxylic acid;

[4S-[4α, 7α(R*), 12bβ]]-7-[(1-Oxo-2(S)-acetylthio-3-phenylpropyl)amino]- 1,2,3,4,6,7,8,12b-hexahydro-6-oxo-1H-[1,4]-oxazino[3,4-a][2]benzazepine-4-carboxylic acid;

[4S-[4α, 7α(R*), 12bβ]]-7-[(1-Oxo-2(S)-acetylthio-3-phenylpropyl)amino]- 1,2,3,4,6,7,8,12b-hexahydro-6-oxo-1H-[1,4]-oxazino[3,4-a][2]benzazepine-4-carboxylic acid, pivaloyloxymethyl ester;

[4S-[4α, 7α(R*), 12bβ]]-7-[(1-Oxo-2(S)-thio-3-phenylpropyl)amino]- 1,2,3,4,6,7,8,12b-hexahydro-6-oxo-1H-[1,4]-thiazino[3,4-a][2]benzazepine-4-carboxylic acid;

[4S-[4α, 7α(R*), 12bβ]]-7-[(1-Oxo-2(S)-acetylthio-3-phenylpropyl)amino]- 1,2,3,4,6,7,8,12b-hexahydro-6-oxo-1H-[1,4]-thiazino[3,4-a][2]benzazepine-4-carboxylic acid;

[4S-[4α, 7α(R*), 12bβ]]-7-[(1-Oxo-2(S)-acetylthio-3-phenylpropyl)amino]- 1,2,3,4,6,7,8,12b-hexahydro-6-oxo-1H-[1,4]-thiazino[3,4-a][2]benzazepine-4-carboxylic acid, pivaloyloxymethyl ester;

[4S-[4α, 7α(R*), 12bβ]]-7-[(1-Oxo-2(S)-thio-3-phenylpropyl)amino]- 1,2,3,4,6,7,8,12b-hexahydro-6-oxo-1H-[1,4]-azazino[3,4-a][2]benzazepine-4-carboxylic acid;

[4S-[4α, 7α(R*), 12bβ]]-7-[(1-Oxo-2(S)-acetylthio-3-phenylpropyl)amino]- 1,2,3,4,6,7,8,12b-hexahydro-6-oxo-1H-[1,4]-azazino[3,4-a][2]benzazepine-4-carboxylic acid;

[4S-[4α, 7α(R*), 12bβ]]-7-[(1-Oxo-2(S)-acetylthio-3-phenylpropyl)amino]- 1,2,3,4,6,7,8,12b-hexahydro-6-oxo-1H-[1,4]-azazino[3,4-a][2]benzazepine-4-carboxylic acid, pivaloyloxymethyl ester;

[4S-[4α, 7α(R*), 12bβ]]-7-[(1-Oxo-2(S)-thio-3-phenylpropyl)amino]- 1,2,3,4,6,7,8,12b-hexahydro-6-oxo-1H-[1,4]-$N^4$-benzoyl-azazino[3,4-a][2]benzazepine-4-carboxylic acid;

[4S-[4α, 7α(R*), 12bβ]]-7-[(1-Oxo-2(S)-acetylthio-3-phenylpropyl)amino]- 1,2,3,4,6,7,8,12b-hexahydro-6-oxo-1H-[1,4]-$N^4$-benzoyl-azazino[3,4-a][2]benzazepine-4-carboxylic acid;

[4S-[4α, 7α(R*), 12bβ]]-7-[(1-Oxo-2(S)-acetylthio-3-phenylpropyl)amino]- 1,2,3,4,6,7,8,12b-hexahydro-6-oxo-1H-[1,4]-$N^4$-benzoyl-azazino[3,4-a][2]benzazepine-4-carboxylic acid, pivaloyloxymethyl ester;

[4S-[4α, 7α(R*), 12bβ]]-7-[(1-Oxo-2(S)-thio-3-phenylpropyl)amino]- 1,2,3,4,6,7,8,12b-hexahydro-6-oxo-1H-[1,4]-$N^4$-benzoyl-azazino[3,4-a][2]benzazepine-4-carboxylic acid;

[4S-[4α, 7α(R*), 12bβ]]-7-[(1-Oxo-2(S)-acetylthio-3-phenylpropyl)amino]- 1,2,3,4,6,7,8,12b-hexahydro-6-oxo-1H-[1,4]-$N^4$-benzoyl-azazino[3,4-a][2]benzazepine-4-carboxylic acid;

[4S-[4α, 7α(R*), 12bβ]]-7-[(1-Oxo-2(S)-acetylthio-3-phenylpropyl)amino]- 1,2,3,4,6,7,8,12b-hexahydro-6-oxo-1H-[1,4]-$N^4$-benzoyl-azazino[3,4-a][2]benzazepine-4-carboxylic acid, pivaloyloxymethyl ester;

[4S-[4α, 7α(R*), 12bβ]]-7-[(1-Oxo-2(R)-thio-3-( 3,4-methylenedioxyphenyl)propyl)amino]-1,2,3,4,6,7,8,12b-octahydro- 6-oxopyrido[2,1-a][2]benzazepine-4-carboxylic acid;

[4S-[4α, 7α(R*), 12bβ]]-7-[(1-Oxo-2(S)-thio-3-( 3,4-methylenedioxyphenyl)propyl)amino]-1,2,3,4,6,7,8,12b-octahydro- 6-oxopyrido[2,1-a][2]benzazepine-4-carboxylic acid; and

[4S-[4α, 7α(R*), 12bβ]]-7-[(1-Oxo-2-thio-3-( 3,4-methylenedioxyphenyl)propyl)amino]-1,2,3,4,6,7,8,12b-octahydro- 6-oxopyrido[2,1-a][2]benzazepine-4-carboxylic acid.

The following studies illustrate the utility of the compounds of the present invention as enkephalinase inhibitors and as ACE inhibitors.

Enkephalinase is partially purified from rat kidney. The enzyme is extracted from the microvilli fraction by using Triton X-100 according to the method of Malfroy and Schwartz [*J. Biol. Chem.* 259, 14365–14370 (1984)] or by using a proteolytic treatment according to the method of Almenoff and Orlowski [*Biochem.* 22, 590–599 (1983)]. The enzyme is further purified by anion exchange chromatography (Mono Q™ column, Pharmacia) using a Pharmacia FPLC system. The enzyme activity may be measured by the fluorometric methods of Florentin et al. [*Anal. Biochem.* 141, 62–69 (1984)] or of Almenoff and Orlowski [*J. Neurochemistry* 42, 151–157 (1984)]. The enzyme is assayed in 50 nM HEPES buffer (pH 7.4) in a 3.0 mL reaction volume containing 12 μM of the substrate dansyl-D-AlaGly(p-nitro-)PheGly $K_m$=40 μM) at 25° C. The substrate (and inhibitor) is added from a concentrated stock solution in DMSO (up to 0.1 mL DMSO final volume). The enzyme in a small volume (approximately 0.1 μg of FPLC purified protein) is added to initiate the reaction and the rate of fluorescence increase is recorded continuously using a fluorometer (excitation at 339 nm, emission at 562 nm).

The enzymatic activity of ACE is monitored using the spectrophotometric substrate described by Holmquist et al. [*Anal. Biochem.* 95, 540–548 (1979)] and the buffer system described by Ryan [*Methods of Enzymatic Analysis*, 3rd ed., H. U. Bergmeyer, editor; vol. V, Verlag Chemie, Weinhein, 1983, pp. 20–34].

The results of the analysis of enzymatic activity as described in Table 1 indicate that the compounds of the present invention are inhibitors of enkephalinase as well as inhibitors of ACE.

TABLE 1

$K_i$'s of Compounds of Formulas (I) and (II) as Inhibitors of Enkephalinase and of ACE

| Compound of Formula (1) | Enkephalinase, $K_i$ (nM) | ACE, $K_i$ (nM) |
|---|---|---|
| 100,173 | <1 | 0.74 |
| 101,628 | <1 | 6.7 |
| 27,855 | 8 | 5 |
| 101,804 | 1 | 2.1 |
| 100,919 | <1 | 1 |
| 101,519 | <1 | <7 |
| 102,179 | <1 | <7 |

100,173 = [4S-[4a, 7a(R*), 12bβ]]-7-[(1-oxo-2(S)-thio-3-phenylpropyl)amino]-1,2,3,4,6,7,8,12b-octahydro-6-oxo-pyrido[2,1-a][2]benzazepine-4-carboxylic acid
100,628 = [4S-[4a, 7a(R*), 12bβ]]-7-[(1-oxo-2(R)-thio-3-phenylpropyl)amino]-1,2,3,4,6,7,8,12b-octahydro-6-oxo-pyrido[2,1-a][2]benzazepine-4-carboxylic acid
27,855 = [4S-[4a, 7a(R*), 12bβ]]-7-[(1-oxo-2-thio-ethyl)amino]-1,2,3,4,6,7,8,12b-octahydro-6-oxo-pyrido[2,1-a][2]benzazepine-4-carboxylic acid
101,804 = [4S-[4a, 7a(R*), 12bβ]]-7-[(1-oxo-2-thio-2-phenylethyl)amino]-1,2,3,4,6,7,8,12b-octahydro-6-oxo-pyrido[2,1-a][2]benzazepine-4-carboxylic acid
100,919 = [6a(R*), 11bβ]-6-[(S)-(1-oxo-2(R)-thio-3-phenylpropyl)amino]-1,2,3,5,6,7,11b-heptahydro-5-oxo-pyrrolo[2,1-a][2]benzazepine-3(S)-carboxylic acid
101,519 = [4S-[4a, 7a(R*), 12bβ]]-7-[(1-Oxo-2(S)-thio-3-phenylpropyl)amino]-1,2,3,4,6,7,8,12b-hexahydro-6-oxo-1H-[1,4]-oxazino[3,4-a][2]benzazepine-4-carboxylic acid
102,179 = [4S-[4a, 7a(R*), 12bβ]]-7-[(1-Oxo-2(S)-acetylthio-3-phenylpropyl)amino]-1,2,3,4,6,7,8,12b-hexahydro-6-oxo-1H-[1,4]-oxazino[3,4-a][2]benzazepine-4-carboxylic acid

What is claimed is:

1. A method of inhibiting enkephalinase in a patient in need thereof comprising administering to said patient an effective enkephalinase inhibitory amount of a compound of the Formula

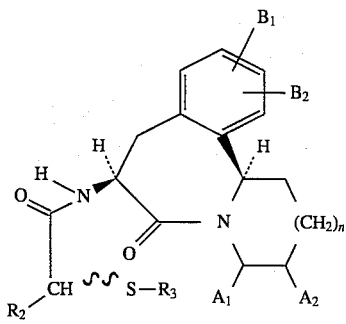

wherein

A₁ and A₂ are each independently hydrogen or —COOR₄ wherein R₄ is hydrogen; —CH₂O—C(O)C(CH₃)₃; a C₁–C₄ alkyl; an Ar—Y— group wherein Ar is aryl and Y is a C₀–C₄ alkyl; or diphenylmethyl; with the proviso that where A₁ is hydrogen, A₂ is —COOR₄, and where A₁ is —COOR₄, A₂ is hydrogen;

B₁ and B₂ are each independently hydrogen; hydroxy; —OR₅ wherein R₅ is a C₁–C₄ alkyl or an Ar—Y— group; or, where B₁ and B₂ are attached to adjacent carbon atoms, B₁ and B₂ can be taken together with said adjacent carbons to form a benzene ring or methylenedioxy;

R₂ is hydrogen, C₁–C₈ alkyl, —CH₂OCH₂CH₂OCH₃ or an Ar—Y— group;

R₃ is hydrogen, acetyl, —CH₂O—C(O)C(CH₃)₃ or benzoyl; and n is an integer 0 or 1.

2. A method of inhibiting enkephalinase in a patient in need thereof comprising administering to said patient an effective enkephalinase inhibitory amount of a compound of the Formula

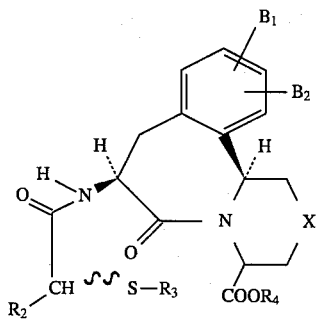

wherein

B₁ and B₂ are each independently hydrogen; hydroxy; —OR₅ wherein R₅ is a C₁–C₄ alkyl or an Ar—Y— group wherein Ar is aryl and Y is a C₀–C₄ alkyl; or, where B₁ and B₂ are attached to adjacent carbon atoms, B₁ and B₂ can be taken together with said adjacent carbons to form a benzene ring or methylenedioxy;

R₂ is hydrogen, C₁–C₈ alkyl, —CH₂OCH₂CH₂OCH₃ or an Ar—Y— group;

R₃ is hydrogen, acetyl, —CH₂O—C(O)C(CH₃)₃ or benzoyl;

R₄ is hydrogen, a C₁–C₄ alkyl or an Ar—Y— group, —CH₂O—C(O)C(CH₃)₃ or diphenylmethyl; and X is —O—, —S—,

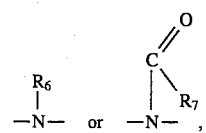

wherein R₆ is hydrogen, a C₁–C₄ alkyl or an Ar—Y— group and R₇ is —CF₃, a C₁–C₁₀ alkyl or an Ar—Y— group.

3. A method according to claim 1 or 2 wherein the patient is in need of an endorphin- or enkephalin-mediated analgesic effect.

4. A method according to claim 1 or 2 wherein the patient is in need of an ANP-mediated hypotensive effect.

5. A method according to claim 1 or 2 wherein the patient is in need of an ANP-mediated diuretic effect.

6. A method according to claim 1 or 2 wherein the patient is suffering from congestive heart failure.

7. A method according to claim 1 or 2 wherein the patient is suffering from irritable bowel syndrome.

8. A method of inhibiting ACE in a patient in need thereof comprising administering to said patient an effective ACE inhibitory amount of a compound of the Formula

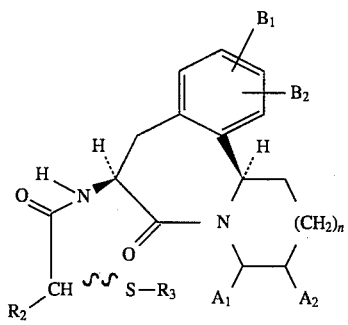

wherein

A₁ and A₂ are each independently hydrogen or —COOR₄ wherein R₄ is hydrogen; —CH₂O—C(O)C(CH₃)₃; a C₁–C₄ alkyl; an Ar—Y— group wherein Ar is aryl and Y is a C₀–C₄ alkyl; or diphenylmethyl; with the proviso that where A₁ is hydrogen, A₂ is —COOR₄, and where A₁ is —COOR₄, A₂ is hydrogen;

B₁ and B₂ are each independently hydrogen; hydroxy; —OR₅ wherein R₅ is a C₁–C₄ alkyl or an Ar—Y— group; or, where B₁ and B₂ are attached to adjacent carbon atoms, B₁ and B₂ can be taken together with said adjacent carbons to form a benzene ring or methylenedioxy;

R₂ is hydrogen, C₁–C₈ alkyl, —CH₂OCH₂CH₂OCH₃ or an Ar—Y— group;

R₃ is hydrogen, acetyl, —CH₂O—C(O)C(CH₃)₃ or benzoyl; and n is an integer 0 or 1.

9. A method of inhibiting ACE in a patient in need thereof comprising administering to said patient an effective AC inhibitory amount of a compound of the Formula

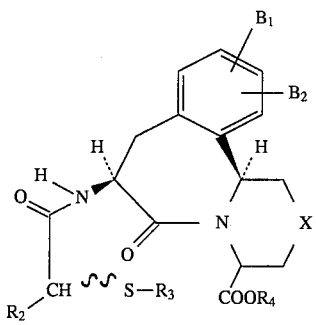

wherein
- $B_1$ and $B_2$ are each independently hydrogen; hydroxy; —$OR_5$ wherein $R_5$ is a $C_1$–$C_4$ alkyl or an Ar—Y— group wherein Ar is aryl and Y is a $C_0$–$C_4$ alkyl; or, where $B_1$ and $B_2$ are attached to adjacent carbon atoms, $B_1$ and $B_2$ can be taken together with said adjacent carbons to form a benzene ring or methylenedioxy;
- $R_2$ is hydrogen, $C_1$–$C_8$ alkyl, —$CH_2OCH_2CH_2OCH_3$ or an Ar—Y— group;
- $R_3$ is hydrogen, acetyl, —$CH_2O$—$C(O)C(CH_3)_3$ or benzoyl;
- $R_4$ is hydrogen, a $C_1$–$C_4$ alkyl or an Ar—Y— group, —$CH_2O$—$C(O)C(CH_3)_3$ or diphenylmethyl; and
- X is —O—, —S—,

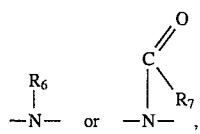

wherein $R_6$ is hydrogen, a $C_1$–$C_4$ alkyl or an Ar—Y— group and $R_7$ is —$CF_3$, a $C_1$–$C_{10}$ alkyl or an Ar—Y— group.

10. A method according to claim 8 or 9 wherein the patient is in need of a hypotensive effect.

11. A method according to claim 8 or 9 wherein the patient is in need of a cognition enhancing effect.

12. A method according to claim 8 or 9 wherein the patient is suffering from congestive heart failure.

13. A method of inhibiting smooth cell proliferation in a patient in need thereof comprising administering to said patient an effective smooth cell proliferation inhibitory amount of a compound of the Formula

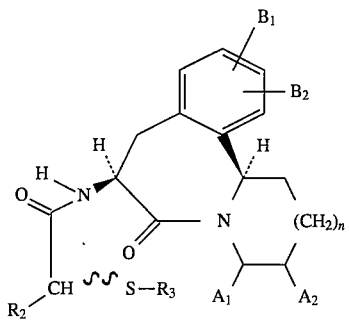

wherein
- $A_1$ and $A_2$ are each independently hydrogen or —$COOR_4$ wherein $R_4$ is hydrogen; —$CH_2O$—$C(O)C(CH_3)_3$; a $C_1$–$C_4$ alkyl; an Ar—Y— group wherein Ar is aryl and Y is a $C_0$–$C_4$ alkyl; or diphenylmethyl; with the proviso that where $A_1$ is hydrogen, $A_2$ is —$COOR_4$, and where $A_1$ is —$COOR_4$, $A_2$ is hydrogen;
- $B_1$ and $B_2$ are each independently hydrogen; hydroxy; —$OR_5$ wherein $R_5$ is a $C_1$–$C_4$ alkyl or an Ar—Y— group; or, where $B_1$ and $B_2$ are attached to adjacent carbon atoms, $B_1$ and $B_2$ can be taken together with said adjacent carbons to form a benzene ring or methylenedioxy;
- $R_2$ is hydrogen, $C_1$–$C_8$ alkyl, —$CH_2OCH_2CH_2OCH_3$ or an Ar—Y— group;
- $R_3$ is hydrogen, acetyl, —$CH_2O$—$C(O)C(CH_3)_3$ or benzoyl; and
- n is an integer 0 or 1.

* * * * *

UNITED STATES PATENT AND TRADEMARK OFFICE
CERTIFICATE OF CORRECTION

PATENT NO. : 5,527,795

DATED : June 18, 1996

INVENTOR(S) : Flynn et al.

Page 1 of 2

It is certified that error appears in the above-indentified patent and that said Letters Patent is hereby corrected as shown below:

Column 5, step g of the patent; the number --9-- is missing from figure.

Column 9, line 38 of the patent reads "structure of 11a" and should read -- structure 11a --. Column 10, Line 40 of the patent reads "with the appropriate with" and should read -- with the appropriate --.

Column 10, line 49 of the patent reads "well know" and should read -- well known --. Column 10, line 51 of the reads "with the appropriate with" and should read -- with the appropriate --.

Column 13, line 27 of the patent reads "fraction 9-20" and should read -- fractions 9-20 --. Column 13, line 49 of the patent reads "the 1/3" and should read -- then 1/3 -- .

Column 15, line 37 of the patent reads "[1,2-a]" and should read -- [2,1-a] -- .

Column 15, line 57 of the patent reads "[(1oxo" and should read -- [(1-oxo --.

Column 15, line 66 of the patent reads "an 1N" and should read -- a 1N --

Column 17, line 10 of the patent reads "1oxo" and should read -- 1-oxo -- .

Column 17, line 51 of the patent reads "(85%)" and should read -- (82%) -- .

Column 32, line 51 of the patent reads "-3-yl" and should read -- -2-yl --.

Colume 33, line 2 of the patent reads "diateromeric" and should read -- diasteromeric --.

Column 33, line 21 of the patent reads "trifluoromethane sulfonic" and should read -- trifluoromethane-sulfonic -- .

Column 35, line 8 of the patent reads "Ad" and should read -- Add -- .

Column 35, line 56 of the patent reads "step q:" and should read -- step g: --.

Coluum 37, line 62 of the patent reads "41 g" and should read -- 41 mg -- .

Column 43, line 11 of the patent reads "-6oxo" and should read -- -6-oxo -- .Column 50, line 8 of the patent reads "Structure 4" and should read -- Structrue 44-- . Column 50, line 26 of the patent reads "enamide" and should read -- enamine --.

Column 50, line 33 of the patent reads "range from" and should read -- range of from -- . Column 55, line 45 of the patent reads "17 hour" and should read -- 17 hours --.

Column 56, line 42 of the patent reads "(15 mL)" and should read -- (5 mL) -- .

Column 56, line 51 of the patent reads " oxazine" and should read -- oxaxine --.

Column 57, line 15 of the patent reads " oxazine" and should read -- oxaxine -- .

Column 63, line 66 of the patent reads "(13.4g" and should read -- (13.5g -- .

Column 65, line 54 of the patent reads "-6-[(1-oxo" and should read -- -6-[(S)-(1-oxo --.Column 68, line 19 of the patent reads "aci/95%" and should read -- acid/95% --.

UNITED STATES PATENT AND TRADEMARK OFFICE
CERTIFICATE OF CORRECTION

PATENT NO. : 5,527,795

DATED : June 18, 1996

INVENTOR(S) : Flynn et al

It is certified that error appears in the above-indentified patent and that said Letters Patent is hereby corrected as shown below:

Column 68, line 42 of the patent reads "slat" and should read -- salt --.
Column 68, line 66 of the patent reads "2 hour" and should read -- 2 hours --.

Column 73, line 50 of the patent reads "(I)" and should read -- (1) --.
Column 78, line 65 of the patent reads "AC" and should read -- ACE --.
Cover page, [75] Inventors, the patent reads "Timothy P. Burkholder" and this name should be deleted.

Signed and Sealed this

Twenty-eighth Day of October, 1997

*Attest:*

BRUCE LEHMAN

*Attesting Officer*   Commissioner of Patents and Trademarks